United States Patent
Iliff

(10) Patent No.: US 8,066,636 B2
(45) Date of Patent: Nov. 29, 2011

(54) DISEASE MANAGEMENT SYSTEM AND METHOD INCLUDING PAIN CODE

(75) Inventor: Edwin C. Iliff, La Jolla, CA (US)

(73) Assignee: Clinical Decision Support, LLC, Nashville, TN (US)

( * ) Notice: Subject to any disclaimer, the term of this patent is extended or adjusted under 35 U.S.C. 154(b) by 571 days.

(21) Appl. No.: 11/933,077

(22) Filed: Oct. 31, 2007

(65) Prior Publication Data

US 2008/0051639 A1 Feb. 28, 2008

Related U.S. Application Data

(62) Division of application No. 10/261,919, filed on Oct. 1, 2002, now Pat. No. 7,297,108, which is a division of application No. 09/818,187, filed on Mar. 26, 2001, now abandoned, which is a division of application No. 09/042,075, filed on Mar. 13, 1998, now Pat. No. 6,234,964.

(60) Provisional application No. 60/040,522, filed on Mar. 13, 1997.

(51) Int. Cl.
*A61B 5/00* (2006.01)

(52) U.S. Cl. .................................. 600/300; 128/920

(58) Field of Classification Search .................. 600/300, 600/301; 128/903–905, 920
See application file for complete search history.

(56) References Cited

U.S. PATENT DOCUMENTS

| | | | |
|---|---|---|---|
| 3,970,996 A | 7/1976 | Yasaka et al. |
| 4,051,522 A | 9/1977 | Healy et al. |
| 4,220,160 A | 9/1980 | Kimball et al. |
| 4,290,114 A | 9/1981 | Sinay |
| 4,315,309 A | 2/1982 | Coli |
| 4,337,377 A | 6/1982 | Van Riper et al. |
| 4,428,381 A | 1/1984 | Hepp |
| 4,458,693 A | 7/1984 | Badzinski et al. |
| 4,465,077 A | 8/1984 | Schneider |
| 4,531,527 A | 7/1985 | Reinhold, Jr. et al. |

(Continued)

FOREIGN PATENT DOCUMENTS

CN 1291749 A 4/2001

(Continued)

OTHER PUBLICATIONS

International Statistical Classification of Diseases and Related Health Problems. Wikipedia, Updated Jan. 31, 2011.*

(Continued)

*Primary Examiner* — Henry M Johnson, III
*Assistant Examiner* — Kai Rajan
(74) *Attorney, Agent, or Firm* — Suiter Swantz pc llo

(57) ABSTRACT

A system and method for allowing a patient to access an automated process for managing a specified health problem called a disease. The system performs disease management in a fully automated manner, using periodic interactive dialogs with the patient to obtain health state measurements from the patient, to evaluate and assess the progress of the patient's disease, to review and adjust therapy to optimal levels, and to give the patient medical advice for administering treatment and handling symptom flare-ups and acute episodes of the disease. The medical records are updated, the progression of the disease is stored and tracked, and the patient's preferences for treatment are stored and then used to offer medical advice based on the current state of the disease. A prestored general disease trend curve is compared against a patient specific disease trend curve, and the system makes an automated response such as adjusting therapy.

24 Claims, 31 Drawing Sheets

U.S. PATENT DOCUMENTS

| | | |
|---|---|---|
| 4,606,352 A | 8/1986 | Geddes et al. |
| 4,712,562 A | 12/1987 | Ohayon et al. |
| 4,731,726 A | 3/1988 | Allen, III |
| 4,733,354 A | 3/1988 | Potter et al. |
| 4,770,189 A | 9/1988 | Shyu |
| 4,803,625 A | 2/1989 | Fu et al. |
| 4,825,869 A | 5/1989 | Sasmor et al. |
| 4,838,275 A | 6/1989 | Lee |
| 4,839,822 A | 6/1989 | Dormond et al. |
| 4,858,121 A | 8/1989 | Barber et al. |
| 4,868,763 A | 9/1989 | Masui et al. |
| 4,933,873 A | 6/1990 | Kaufman et al. |
| 4,945,476 A | 7/1990 | Bodick et al. |
| 4,962,491 A | 10/1990 | Schaeffer |
| 4,974,607 A | 12/1990 | Miwa |
| 4,975,840 A | 12/1990 | DeTore et al. |
| 5,012,411 A | 4/1991 | Policastro et al. |
| 5,012,815 A | 5/1991 | Bennett et al. |
| 5,023,785 A | 6/1991 | Adrion et al. |
| 5,030,948 A | 7/1991 | Rush |
| 5,054,493 A | 10/1991 | Cohn et al. |
| 5,084,819 A | 1/1992 | Dewey et al. |
| 5,099,424 A | 3/1992 | Schneiderman |
| 5,113,869 A | 5/1992 | Nappholz et al. |
| 5,193,541 A | 3/1993 | Hatsuwi |
| 5,196,682 A | 3/1993 | Englehardt |
| 5,228,449 A | 7/1993 | Christ et al. |
| 5,235,510 A | 8/1993 | Yamada et al. |
| 5,241,621 A | 8/1993 | Smart |
| 5,255,187 A | 10/1993 | Sorensen |
| 5,257,627 A | 11/1993 | Rapoport |
| 5,263,123 A | 11/1993 | Hayashi |
| 5,265,613 A | 11/1993 | Feldman et al. |
| 5,299,121 A | 3/1994 | Brill et al. |
| 5,307,263 A | 4/1994 | Brown |
| 5,337,752 A | 8/1994 | Reeves |
| 5,347,632 A | 9/1994 | Filepp et al. |
| 5,357,427 A | 10/1994 | Langen et al. |
| 5,377,258 A | 12/1994 | Bro |
| 5,390,238 A | 2/1995 | Kirk et al. |
| 5,404,292 A | 4/1995 | Hendrickson |
| 5,415,167 A | 5/1995 | Wilk |
| 5,418,888 A | 5/1995 | Alden |
| 5,421,343 A | 6/1995 | Feng |
| 5,435,324 A | 7/1995 | Brill |
| 5,437,278 A | 8/1995 | Wilk |
| 5,441,047 A | 8/1995 | David et al. |
| 5,442,728 A | 8/1995 | Kaufman et al. |
| 5,463,548 A | 10/1995 | Asada et al. |
| 5,471,382 A | 11/1995 | Tallman et al. |
| 5,473,537 A | 12/1995 | Glazer et al. |
| 5,481,647 A | 1/1996 | Brody et al. |
| 5,486,999 A | 1/1996 | Mebane |
| 5,517,405 A | 5/1996 | McAndrew et al. |
| 5,519,433 A | 5/1996 | Lappington et al. |
| 5,533,522 A | 7/1996 | Feng |
| 5,541,977 A | 7/1996 | Hodges et al. |
| 5,544,649 A | 8/1996 | David et al. |
| 5,553,609 A | 9/1996 | Chen et al. |
| 5,555,169 A | 9/1996 | Namba et al. |
| 5,572,421 A | 11/1996 | Altman et al. |
| 5,583,758 A | 12/1996 | McIlroy et al. |
| 5,594,638 A | 1/1997 | Iliff |
| 5,596,994 A | 1/1997 | Bro |
| 5,601,435 A | 2/1997 | Quy |
| 5,619,991 A | 4/1997 | Sloane |
| 5,622,171 A | 4/1997 | Asada et al. |
| 5,633,910 A | 5/1997 | Cohen |
| 5,642,731 A * | 7/1997 | Kehr ............................ 600/300 |
| 5,642,936 A | 7/1997 | Evans |
| 5,659,793 A | 8/1997 | Escobar et al. |
| 5,660,176 A | 8/1997 | Iliff |
| 5,672,154 A | 9/1997 | Sillén et al. |
| 5,675,760 A | 10/1997 | Houwen et al. |
| 5,678,562 A | 10/1997 | Sellers |
| 5,692,220 A | 11/1997 | Diamond et al. |
| 5,692,501 A | 12/1997 | Minturn |
| 5,694,939 A | 12/1997 | Cowings |
| 5,703,786 A | 12/1997 | Conkright |
| 5,711,297 A | 1/1998 | Iliff |
| 5,720,502 A * | 2/1998 | Cain ............................ 283/115 |
| 5,722,418 A | 3/1998 | Bro |
| 5,724,968 A | 3/1998 | Iliff |
| 5,724,983 A | 3/1998 | Selker et al. |
| 5,732,397 A | 3/1998 | DeTore et al. |
| 5,746,204 A | 5/1998 | Schauss |
| 5,769,074 A | 6/1998 | Barnhill et al. |
| 5,772,585 A * | 6/1998 | Lavin et al. ................... 600/300 |
| 5,778,882 A * | 7/1998 | Raymond et al. ............. 600/513 |
| 5,788,640 A | 8/1998 | Peters |
| 5,794,208 A | 8/1998 | Goltra |
| 5,800,347 A | 9/1998 | Skates et al. |
| 5,802,495 A | 9/1998 | Goltra |
| 5,809,476 A * | 9/1998 | Ryan ................................ 705/2 |
| 5,812,984 A | 9/1998 | Goltra |
| 5,822,715 A | 10/1998 | Worthington et al. |
| 5,823,949 A | 10/1998 | Goltra |
| 5,828,943 A | 10/1998 | Brown |
| 5,832,448 A | 11/1998 | Brown |
| 5,835,900 A | 11/1998 | Fagg, III et al. |
| 5,839,430 A | 11/1998 | Cama |
| 5,862,304 A | 1/1999 | Ravdin et al. |
| 5,868,669 A | 2/1999 | Iliff |
| 5,879,163 A | 3/1999 | Brown et al. |
| 5,887,133 A | 3/1999 | Brown et al. |
| 5,897,493 A | 4/1999 | Brown |
| 5,899,855 A | 5/1999 | Brown |
| 5,908,383 A | 6/1999 | Brynjestad |
| 5,909,679 A | 6/1999 | Hall |
| 5,910,107 A | 6/1999 | Iliff |
| 5,911,132 A | 6/1999 | Sloane |
| 5,918,603 A | 7/1999 | Brown |
| 5,933,136 A | 8/1999 | Brown |
| 5,935,060 A | 8/1999 | Iliff |
| 5,940,801 A | 8/1999 | Brown |
| 5,951,300 A | 9/1999 | Brown |
| 5,953,704 A | 9/1999 | McIlroy et al. |
| 5,956,501 A | 9/1999 | Brown |
| 5,960,403 A | 9/1999 | Brown |
| 5,974,389 A | 10/1999 | Clark et al. |
| 5,976,082 A | 11/1999 | Wong et al. |
| 5,987,519 A | 11/1999 | Peifer |
| 5,997,476 A | 12/1999 | Brown |
| 6,001,060 A | 12/1999 | Churchill et al. |
| 6,022,315 A | 2/2000 | Iliff |
| 6,032,119 A | 2/2000 | Brown et al. |
| 6,032,678 A | 3/2000 | Rottem |
| 6,071,236 A | 6/2000 | Iliff |
| 6,081,786 A | 6/2000 | Barry et al. |
| 6,101,478 A | 8/2000 | Brown |
| 6,106,459 A | 8/2000 | Clawson |
| 6,113,540 A | 9/2000 | Iliff |
| 6,117,073 A | 9/2000 | Jones et al. |
| 6,144,837 A | 11/2000 | Quy |
| 6,149,585 A | 11/2000 | Gray |
| 6,151,586 A | 11/2000 | Brown |
| 6,161,095 A | 12/2000 | Brown |
| 6,167,362 A | 12/2000 | Brown |
| 6,168,563 B1 | 1/2001 | Brown |
| 6,177,940 B1 | 1/2001 | Bond et al. |
| 6,186,145 B1 | 2/2001 | Brown |
| 6,189,029 B1 | 2/2001 | Fuerst |
| 6,196,970 B1 | 3/2001 | Brown |
| 6,206,829 B1 | 3/2001 | Iliff |
| 6,230,142 B1 | 5/2001 | Benigno et al. |
| 6,233,539 B1 | 5/2001 | Brown |
| 6,234,964 B1 | 5/2001 | Iliff |
| 6,240,393 B1 | 5/2001 | Brown |
| 6,246,975 B1 | 6/2001 | Rivonelli et al. |
| 6,246,992 B1 | 6/2001 | Brown |
| 6,247,002 B1 | 6/2001 | Steels |
| 6,248,063 B1 | 6/2001 | Barnhill et al. |
| 6,248,065 B1 | 6/2001 | Brown |
| 6,260,022 B1 | 7/2001 | Brown |
| 6,270,455 B1 | 8/2001 | Brown |
| 6,270,456 B1 | 8/2001 | Iliff |
| 6,330,426 B2 | 12/2001 | Brown et al. |

| | | |
|---|---|---|
| 6,334,778 B1 | 1/2002 | Brown |
| 6,368,273 B1 | 4/2002 | Brown |
| 6,375,469 B1 | 4/2002 | Brown |
| 6,379,301 B1 | 4/2002 | Worthington et al. |
| 6,381,577 B1 | 4/2002 | Brown |
| 6,468,210 B1 | 10/2002 | Iliff |
| 6,475,143 B2 | 11/2002 | Iliff |
| 6,482,156 B2 | 11/2002 | Iliff |
| 6,524,241 B2 | 2/2003 | Iliff |
| 6,527,713 B2 | 3/2003 | Iliff |
| 6,569,093 B2 | 5/2003 | Iliff |
| 6,597,392 B1 | 7/2003 | Jenkins et al. |
| 6,598,035 B2 | 7/2003 | Branson et al. |
| 6,601,055 B1 | 7/2003 | Roberts |
| 6,641,532 B2 | 11/2003 | Iliff |
| 6,687,685 B1 | 2/2004 | Sadeghi et al. |
| 6,725,209 B1 | 4/2004 | Iliff |
| 6,730,027 B2 | 5/2004 | Iliff |
| 6,746,399 B2 | 6/2004 | Iliff |
| 6,748,353 B1 | 6/2004 | Iliff |
| 6,764,447 B2 | 7/2004 | Iliff |
| 6,767,325 B2 | 7/2004 | Iliff |
| 6,770,029 B2 | 8/2004 | Iliff |
| 6,817,980 B2 | 11/2004 | Iliff |
| 6,849,045 B2 | 2/2005 | Iliff |
| 6,900,807 B1 | 5/2005 | Liongosari et al. |
| 6,903,657 B2 | 6/2005 | Kwoen |
| 6,968,375 B1 | 11/2005 | Brown |
| 7,076,437 B1 | 7/2006 | Levy |
| 7,167,818 B2 | 1/2007 | Brown |
| 7,223,235 B2 | 5/2007 | Brown |
| 7,223,236 B2 | 5/2007 | Brown |
| 7,252,636 B2 | 8/2007 | Brown |
| 7,258,666 B2 | 8/2007 | Brown |
| 7,259,681 B2 | 8/2007 | Kwoen |
| 7,264,591 B2 | 9/2007 | Brown |
| 7,297,108 B2 | 11/2007 | Iliff |
| 7,297,109 B2 | 11/2007 | Brown |
| 7,297,111 B2 | 11/2007 | Iliff |
| 7,300,402 B2 | 11/2007 | Iliff |
| 7,305,348 B1 | 12/2007 | Brown |
| 7,306,560 B2 | 12/2007 | Iliff |
| 7,310,668 B2 | 12/2007 | Brown |
| 7,320,030 B2 | 1/2008 | Brown |
| 7,344,496 B2 | 3/2008 | Iliff |
| 7,392,167 B2 | 6/2008 | Brown |
| 7,399,276 B1 | 7/2008 | Brown et al. |
| 7,516,192 B2 | 4/2009 | Brown |
| 7,769,600 B2 | 8/2010 | Iliff |
| 7,780,595 B2 | 8/2010 | Iliff |
| 2001/0012913 A1 | 8/2001 | Iliff |
| 2001/0039503 A1 | 11/2001 | Chan et al. |
| 2001/0053875 A1 | 12/2001 | Iliff |
| 2002/0029157 A1 | 3/2002 | Marchosky |
| 2002/0068857 A1 | 6/2002 | Iliff |
| 2002/0148477 A1 | 10/2002 | Kwoen |
| 2002/0186818 A1 | 12/2002 | Arnaud et al. |
| 2003/0036686 A1 | 2/2003 | Iliff |
| 2003/0069753 A1 | 4/2003 | Brown |
| 2003/0153819 A1 | 8/2003 | Iliff |
| 2003/0163299 A1 | 8/2003 | Iliff |
| 2003/0181790 A1 | 9/2003 | David et al. |
| 2004/0017475 A1 | 1/2004 | Akers et al. |
| 2004/0019259 A1 | 1/2004 | Brown |
| 2004/0059200 A1 | 3/2004 | Iliff |
| 2004/0107116 A1 | 6/2004 | Brown |
| 2004/0116780 A1 | 6/2004 | Brown |
| 2004/0117207 A1 | 6/2004 | Brown |
| 2004/0117208 A1 | 6/2004 | Brown |
| 2004/0117209 A1 | 6/2004 | Brown |
| 2004/0117210 A1 | 6/2004 | Brown |
| 2004/0193377 A1 | 9/2004 | Brown |
| 2004/0199332 A1 | 10/2004 | Iliff |
| 2004/0199409 A1 | 10/2004 | Brown |
| 2004/0219500 A1 | 11/2004 | Brown |
| 2004/0249778 A1 | 12/2004 | Iliff |
| 2005/0010088 A1 | 1/2005 | Iliff |
| 2005/0010444 A1 | 1/2005 | Iliff |
| 2005/0027562 A1 | 2/2005 | Brown |
| 2005/0060194 A1 | 3/2005 | Brown |
| 2005/0080652 A1 | 4/2005 | Brown |
| 2005/0086083 A1 | 4/2005 | Brown |
| 2005/0177391 A1 | 8/2005 | Shimizu et al. |
| 2005/0228883 A1 | 10/2005 | Brown |
| 2005/0234306 A1 | 10/2005 | Schulte et al. |
| 2005/0256739 A1 | 11/2005 | Brown |
| 2005/0273359 A1 | 12/2005 | Young |
| 2005/0273509 A1 | 12/2005 | Brown |
| 2006/0004611 A1 | 1/2006 | Brown |
| 2006/0010014 A1 | 1/2006 | Brown |
| 2006/0089969 A1 | 4/2006 | Brown |
| 2006/0100910 A1 | 5/2006 | Brown |
| 2006/0135859 A1 | 6/2006 | Iliff |
| 2006/0178914 A1 | 8/2006 | Brown |
| 2006/0189853 A1 | 8/2006 | Brown |
| 2006/0234202 A1 | 10/2006 | Brown |
| 2006/0235722 A1 | 10/2006 | Brown |
| 2006/0241975 A1 | 10/2006 | Brown |
| 2006/0247951 A1 | 11/2006 | Brown |
| 2006/0247979 A1 | 11/2006 | Brown |
| 2006/0252089 A1 | 11/2006 | Brown |
| 2006/0253303 A1 | 11/2006 | Brown |
| 2006/0253574 A1 | 11/2006 | Brown |
| 2006/0253576 A1 | 11/2006 | Brown |
| 2006/0271404 A1 | 11/2006 | Brown |
| 2006/0285736 A1 | 12/2006 | Brown |
| 2006/0287889 A1 | 12/2006 | Brown |
| 2006/0287931 A1 | 12/2006 | Brown |
| 2006/0294233 A1 | 12/2006 | Brown |
| 2007/0016445 A1 | 1/2007 | Brown |
| 2007/0016446 A1 | 1/2007 | Brown |
| 2007/0016447 A1 | 1/2007 | Brown |
| 2007/0016448 A1 | 1/2007 | Brown |
| 2007/0021984 A1 | 1/2007 | Brown |
| 2007/0048691 A1 | 3/2007 | Brown |
| 2007/0055486 A1 | 3/2007 | Brown |
| 2007/0061167 A1 | 3/2007 | Brown |
| 2007/0067251 A1 | 3/2007 | Brown |
| 2007/0078681 A1 | 4/2007 | Brown |
| 2007/0094049 A1 | 4/2007 | Brown |
| 2007/0100665 A1 | 5/2007 | Brown |
| 2007/0100934 A1 | 5/2007 | Brown |
| 2007/0111176 A1 | 5/2007 | Brown |
| 2007/0118403 A1 | 5/2007 | Brown |
| 2007/0118404 A1 | 5/2007 | Brown |
| 2007/0124179 A1 | 5/2007 | Brown |
| 2007/0168226 A1 | 7/2007 | Brown |
| 2007/0168242 A1 | 7/2007 | Brown |
| 2007/0212671 A1 | 9/2007 | Brown |
| 2007/0213608 A1 | 9/2007 | Brown |
| 2007/0299321 A1 | 12/2007 | Brown |
| 2008/0004915 A1 | 1/2008 | Brown |
| 2008/0045811 A1 | 2/2008 | Iliff |
| 2008/0046268 A1 | 2/2008 | Brown |
| 2008/0051638 A1 | 2/2008 | Iliff |
| 2008/0051640 A1 | 2/2008 | Iliff |
| 2008/0051641 A1 | 2/2008 | Iliff |
| 2008/0052116 A1 | 2/2008 | Iliff |
| 2008/0052118 A1 | 2/2008 | Iliff |
| 2008/0052119 A1 | 2/2008 | Iliff |
| 2008/0052120 A1 | 2/2008 | Iliff |
| 2008/0052121 A1 | 2/2008 | Iliff |
| 2008/0052122 A1 | 2/2008 | Iliff |
| 2008/0052123 A1 | 2/2008 | Iliff |
| 2008/0052130 A1 | 2/2008 | Iliff |
| 2008/0052132 A1 | 2/2008 | Iliff |
| 2008/0052318 A1 | 2/2008 | Iliff |
| 2008/0059227 A1 | 3/2008 | Clapp |
| 2008/0059232 A1 | 3/2008 | Iliff |
| 2008/0059247 A1 | 3/2008 | Iliff |
| 2008/0072147 A1 | 3/2008 | Brown |
| 2008/0097180 A1 | 4/2008 | Brown |
| 2008/0097181 A1 | 4/2008 | Brown |
| 2008/0103377 A1 | 5/2008 | Brown |
| 2008/0108888 A1 | 5/2008 | Brown |
| 2008/0109172 A1 | 5/2008 | Brown |
| 2008/0162393 A1 | 7/2008 | Iliff |

| | | | |
|---|---|---|---|
| 2008/0262557 | A1 | 10/2008 | Brown |
| 2008/0269571 | A1 | 10/2008 | Brown et al. |
| 2009/0007924 | A1 | 1/2009 | Iliff |

FOREIGN PATENT DOCUMENTS

| | | |
|---|---|---|
| CN | 1477581 A | 2/2004 |
| DE | 4430184 C2 | 3/1995 |
| DE | 4430164 A1 | 2/1996 |
| EP | 0320749 A2 | 6/1989 |
| EP | 0 447 710 A1 | 9/1991 |
| EP | 0 531 889 A2 | 3/1993 |
| EP | 0 643 360 A2 | 3/1996 |
| EP | 0 720 336 A2 | 7/1996 |
| JP | 03191952 | 8/1991 |
| JP | 3202047 | 9/1991 |
| JP | 04015035 | 1/1992 |
| JP | 04015035 A | 1/1992 |
| JP | 4056561 | 2/1992 |
| JP | 06083847 | 3/1994 |
| JP | 06274472 | 9/1994 |
| JP | 08117210 A | 5/1996 |
| JP | 08140944 | 6/1996 |
| JP | 08164127 A | 6/1996 |
| JP | 08275927 | 10/1996 |
| WO | WO 93/23819 | 11/1993 |
| WO | WO 94/00817 | 1/1994 |
| WO | WO 94/06088 | 3/1994 |
| WO | WO 95/06296 | 3/1995 |
| WO | WO 95/06298 | 3/1995 |
| WO | WO 95/19604 | 7/1995 |
| WO | WO 96/22577 | 7/1996 |
| WO | WO 97/05553 | 2/1997 |
| WO | WO 98/002836 | 1/1998 |
| WO | WO 99/52025 | 10/1999 |
| WO | WO 00/32088 A1 | 6/2000 |
| WO | WO 01/61616 A2 | 8/2001 |
| WO | WO 01/85021 | 11/2001 |
| WO | WO 02/039250 A2 | 5/2002 |
| WO | WO 02/42876 A2 | 5/2002 |
| WO | WO 03/040879 A2 | 5/2003 |
| WO | WO 03/040964 A2 | 5/2003 |
| WO | WO 03/040965 A2 | 5/2003 |
| WO | WO 03/040989 A2 | 5/2003 |
| WO | WO 03/040990 A2 | 5/2003 |

OTHER PUBLICATIONS

List of ICD9 Codes 780-799. Wikipedia, Updated Dec. 28, 2010.*
Alexander G., Health Risk Appraisal, Intern Electro J Health Edu., 2000, 3(Special): 122-137.
Fielding J., Appraising the Health of Health Risk Appraisal, Am J Pub Health, Apr. 1982, 72(4): 337-340.
Goetz et al., Health Risk Appraisal: The Estimation of Risk, Health Promotion at the Worksite, Mar.-Apr. 1980, 95(2): 119-126.
Ellis et al., Health Education using Microcomputers II: One year in the Clinic; Preventive Medicine, 1982, 11: 212-224.
Ellis et al., Health Education using Microcomputers: Initial Acceptability, Preventive Medicine, Jan. 1981, 10(1): 77-84.
Exhibit A, Part 1 to Second Revised Joint Claim Construction Statement, *Healthways, Inc.* v. *Alere, LLC*, U.S. District Court for the Northern District of Illinois, Case No. 08CV06337, Nov. 6, 2009, 15 pages.
Exhibit A, Part 2 to Second Revised Joint Claim Construction Statement, *Healthways, Inc.* v. *Alere, LLC*, U.S. District Court for the Northern District of Illinois, Case No. 08CV06337, Nov. 6, 2009, 15 pages.
Exhibit A, Part 3 to Second Revised Joint Claim Construction Statement, *Healthways, Inc.* v. *Alere, LLC*, U.S. District Court for the Northern District of Illinois, Case No. 08CV06337, Nov. 6, 2009, 17 pages.
Exhibit B to Second Revised Joint Claim Construction Statement, *Healthways, Inc.* v. *Alere, LLC*, U.S. District Court for the Northern District of Illinois, Case No. 08CV06337, Nov. 6, 2009, 24 pages.
Exhibit C to Second Revised Joint Claim Construction Statement, *Healthways, Inc.* v. *Alere, LLC*, U.S. District Court for the Northern District of Illinois, Case No. 08CV06337, Nov. 6, 2009, 8 pages.
Exhibit D to Second Revised Joint Claim Construction Statement, *Healthways, Inc.* v. *Alere, LLC*, U.S. District Court for the Northern District of Illinois, Case No. 08CV06337, Nov. 6, 2009, 8 pages.
Exhibit E to Second Revised Joint Claim Construction Statement, *Healthways, Inc.* v. *Alere, LLC*, U.S. District Court for the Northern District of Illinois, Case No. 08CV06337, Nov. 6, 2009, 8 pages.
Exhibit F to Second Revised Joint Claim Construction Statement, *Healthways, Inc.* v. *Alere, LLC*, U.S. District Court for the Northern District of Illinois, Case No. 08CV06337, Nov. 6, 2009, 7 pages.
Exhibit G to Second Revised Joint Claim Construction Statement, *Healthways, Inc.* v. *Alere, LLC*, U.S. District Court for the Northern District of Illinois, Case No. 08CV06337, Nov. 6, 2009, 7 pages.
Exhibit H to Second Revised Joint Claim Construction Statement, *Healthways, Inc.* v. *Alere, LLC*, U.S. District Court for the Northern District of Illinois, Case No. 08CV06337, Nov. 6, 2009, 9 pages.
Exhibit I to Second Revised Joint Claim Construction Statement, *Healthways, Inc.* v. *Alere, LLC*, U.S. District Court for the Northern District of Illinois, Case No. 08CV06337, Nov. 6, 2009, 9 pages.
Exhibit J to Second Revised Joint Claim Construction Statement, *Healthways, Inc.* v. *Alere, LLC*, U.S. District Court for the Northern District of Illinois, Case No. 08CV06337, Nov. 6, 2009, 9 pages.
Exhibit K to Second Revised Joint Claim Construction Statement, *Healthways, Inc.* v. *Alere, LLC*, U.S. District Court for the Northern District of Illinois, Case No. 08CV06337, Nov. 6, 2009, 6 pages.
Exhibit L to Second Revised Joint Claim Construction Statement, *Healthways, Inc.* v. *Alere, LLC*, U.S. District Court for the Northern District of Illinois, Case No. 08CV06337, Nov. 6, 2009, 5 pages.
Healthways, Inc.'s Third Supplemental Response to Defendant and Counterclaimant Alere, LLC's First Set of Interrogatories and Exhibit E, *Healthways, Inc.* v. *Alere, LLC*, U.S. District Court for the Northern District of Illinois, Case No. 08CV06337, Oct. 28, 2009, 14 pages.
Reply Memorandum in Support of Plaintiffs' Partial Motion for Judgment on the Pleadings Pursuant to Rule 12(C) and Rule 9(8), *Healthways, Inc.* v. *Alere, LLC*, U.S. District Court for the Northern District of Illinois, Case No. 08CV06337, Oct. 23, 2009, 9 pages.
Second Revised Joint Claim Construction Statement, *Healthways, Inc.* v. *Alere, LLC*, U.S. District Court for the Northern District of Illinois, Case No. 08CV06337, Nov. 6, 2009, 63 pages.
Replacement Statement and Explanation dated Nov. 21, 2009 from Request for Ex Parte Reexamination of U.S. Patent No. 6,116,540; U.S. Appl. No. 90/009,594, filed Nov. 21, 2009.
Australian Office Action dated Nov. 10, 2008 for Australian Patent Application No. 2007201421, filed Mar. 13, 1998.
European Office Action dated Jan. 18, 2010 for European Patent Application No. 98911601.7, filed Mar. 13, 1998.
Japanese Decision on Appeal dated Jul. 7, 2009 for Japanese Patent Application No. 539802/98, filed Mar. 13, 1998.
Japanese Office Action dated Sep. 3, 2009 for Japanese Patent Application No. 2008-097100, filed Mar. 13, 1998.
Gardner, Integrated Computer Systems for Monitoring of the Critically Ill, Proceedings of 1st Annual Symposium on Computer Application in Medical Care, Washington, D.C., IEEE Computer Society, 1977, pp. 301-302.
Koska, Mary T., Primary Care: Hospitals Begin to Target Community Needs, Hospitals, Apr. 5, 1990, 64(7): 24-28.
Plaintiff's Opening Brief on Claim Construction, *Healthways, Inc.* v. *Alere, LLC*, U.S. District Court for the Northern District of Illinois, Case No. 08CV06337, Apr. 20, 2010, 33 pages.
Exhibit 12 to Plaintiffs Opening Brief on Claim Construction, *Healthways, Inc.* v. *Alere, LLC*, U.S. District Court for the Northern District of Illinois, Case No. 08CV06337, Apr. 20, 2010, 14 pages.
Exhibit 13 to Plaintiffs Opening Brief on Claim Construction, *Healthways, Inc.* v. *Alere, LLC*, U.S. District Court for the Northern District of Illinois, Case No. 08CV06337, Apr. 20, 2010, 12 pages.
Exhibit 14 to Plaintiffs Opening Brief on Claim Construction, *Healthways, Inc.* v. *Alere, LLC*, U.S. District Court for the Northern District of Illinois, Case No. 08CV06337, Apr. 20, 2010, 6 pages.
Chinese Office Action dated Feb. 26, 2010 in Chinese Patent Application No. 200410057537.8, filed Mar. 13, 1998.
Chinese Office Action dated Jul. 10, 2009 in Chinese Patent Application No. 200410057537.8, filed Mar. 13, 1998.
Ball et al. Eds. Computers in Health Care: Aspects of the Computer-based Patient Record, Springer Verlag, 1992, pp. 1-336.

Barr et al., (Eds.) The Handbook of Artificial Intelligence, HeurisTech Press, 1982, vol. II, Chapter VIII, pp. 175-222.

Bischoff, A Knowledge Based System for Assisting in Differential Diagnosis of Chemically Dependent/Mentally Ill Patients, Computers in Human Services, 1992, vol. 8, Nos. 3/4, pp. 143-151.

Bortolan et al., The role of patient history in a decision support system, IEEE, Computers in Cardiology, Sep. 1990, Proceedings, pp. 357-360.

Brown et al., Information Infrastructure Task Force, The National Information Infrastructure: Agenda for Action, Sep. 15, 1993, pp. 26.

Christine, The Future of Health Care Technologies, HighBeam Research, Risk Management, Nov. 1, 1992, 1-3.

Common Carrier Week 8, Home Education and Health Benefits said to be underestimated, Warren Publishing Inc., Jan. 20, 1992, 9(3): 1-3.

Creative Strategies International (CSI), The Emerging Self-Help Healthcare Market—Microcomputer Applications, 1984, pp. 130.

Evans, C. Edward, A Computer in the Waiting Room: Who Needs the Doctor?, Can Fam Phys., Apr. 1984, 30: 869-876.

Federal Register, National Telecommunications and Information Administration, DOC—Administration Policy Statement, Notices, Sep. 21, 1993, Fed. Reg., 58(181): 49025-49036.

First Opinion Corporation, Canadian Trademark Application File History TMA447,669, registered Sep. 15, 1995 for the Trademark/Servicemark: First Opinion, pp. 51.

Haug et al., Decision Support in Medicine: Examples from the HELP System, Computers and Biomedical Research, 1994, 27: 396-418.

Henderson, A Trainable Pattern Classifier for Medical Questionnaires, Annals of Biomed Engin., Jan. 27, 1972, 1: 115-133.

Johnson et al., Psychological Systems Questionnaire: An Objective Personality Test designed for on-line computer Presentation, Scoring, and Interpretation, Behav Res Meth Instrument., 1979, 11(2): 257-260.

Lunin, Lois F., On Speaking Terms With the Computer, Information Today, Feb. 1992, 9(2): 19-20.

Malcolm et al., Computer-Assisted Diagnosis of Alcoholism, Computers in Human Services, 1989, 5(3/4): 163-170.

McNish, David A., EMED Electronic Medical Database, DMC Software Packaging and Manual, DMC Software Company., 1987, 7 pages.

Miller et al., The Computerized Carroll Rating Scale, Indiana University School of Medicine, 1985, pp. 344-347.

Partin, A Preliminary Conceptual Framework for the Design, Development, and Use of Client-Oriented Information Systems in Health, J Med Sys. 1987, 11(2/3): 205-217.

Patel et al., A Computer-based, Automated, Telephonic System to Monitor Patient Progress in the Home Setting, J Med Sys., 1992. 16(2/3): 101-112.

Shneiderman, Ben, Touch Screens now offer Compelling Uses, IEEE Software, 1991, pp. 93-94.

Shortliffe et al., A Model of Inexact Reasoning in Medicine, 1975, (shortened/editied version) Mathematical Biosciences, 11: 233-262.

Stead et al., Computer-Assisted Interview of Patients with Functional Headache, Arch Intern Med., 1972, 129: 950-955.

Szolovits et al., Guardian Angel: Patient-Centered Health Information Systems, May 1994, MIT Laboratory for Computer Science, TR-604, pp. 40.

The National Information Infrastructure: Agenda for Action, U.S. Government Paper, 1993, pp. 42.

Walmsley et al., Normal "Anion Gap" (Hyperchloremic) Acidosis, Case Reports, Clin Chem., 1985, 31(2): 309-313.

Weinstock, Edward, An Apple a Day . . . ™, Computer Program Manual, Avant-Garde Publishing Corporation, 1984, pp. 47.

Weiss et al., Glaucoma Consultation by Computer, Comput Biol Med.., Pergamon Press, 1978, 8: 25-40.

Memorandum in Support of Defendant and Counterclaimant Alere, LLC's Motion to Compel Plaintiff Healthways, Inc.'s Response to Interrogatory No. 2, or Preclude Healthway's Future Disclosure of or Reliance on Any Commercial Embodiments, *Healthways, Inc.* v. *Alere, LLC*, U.S. District Court for the Northern District of Illinois, Case No. 08CV06337, Mar. 27, 2009, 20 pages.

Alere LLC's Opposition to Plaintiffs' Partial Motion for Judgment on the Pleadings Pursuant to Rule 12(c) and Rule 9(b), *Healthways, Inc.* v. *Alere, LLC*, U.S. District Court for the Northern District of Illinois, Case No. 08CV06337, Sep. 24, 2009, 20 pages.

Declaration of Goutam Patnaik in Support of Defendant and Counterclaimant Alere, LLC's Motion to Compel Plaintiff Healthways, Inc.'s Response to Interrogatory No. 2, or Preclude Healthway's Future Disclosure of or Reliance on Any Commercial Embodiments, *Healthways, Inc.* v. *Alere, LLC*, U.S. District Court for the Northern District of Illinois, Case No. 08CV06337, Mar. 27, 2009, 4 pages.

Defendant-Counterclaimint Alere LLC's Agreed Motion for Leave to Replace its Opposition to Plaintiffs' Partial Motion for Judgment on the Pleadings Pursuant to Rule 12(c) and Rule 9(b) and Exhibit 3 to its Opposition with Redacted Versions, *Healthways, Inc.* v. *Alere, LLC*, U.S. District Court for the Northern District of Illinois, Case No. 08CV06337, Sep. 30, 2009, 3 pages.

Defendant-Counterclaimant Alere, LLC's Alternative Motion for Leave to File First Amended Answer and Counterclaims, *Healthways, Inc.* v. *Alere, LLC*, U.S. District Court for the Northern District of Illinois, Case No. 08CV06337, Sep. 24, 2009, 3 pages.

Defendant-Counterclaimant Alere, LLC's Memorandum in Support of its Alternative Motion for Leave to File First Amended Answer and Counterclaims, *Healthways, Inc.* v. *Alere, LLC*, U.S. District Court for the Northern District of Illinois, Case No. 08CV06337, Sep. 24, 2009, 17 pages.

Defendant-Counterclaimant Alere, LLC's Unopposed Motion for Leave to Replace its Memorandum in Support of its Alternative Motion for Leave to File First Amended Answer and Counterclaims and First Amended Answer and Counterclaims with Redacted Versions, *Healthways, Inc.* v. *Alere, LLC*, U.S. District Court for the Northern District of Illinois, Case No. 08CV06337, Sep. 30, 2009, 3 pages.

Exhibit 1 to Declaration of Goutam Patnaik in Support of Defendant and Counterclaimant Alere, LLC's Motion to Compel Plaintiff Healthways, Inc.'s Response to Interrogatory No. 2, or Preclude Healthway's Future Disclosure of or Reliance on Any Commercial Embodiments, *Healthways, Inc.* v. *Alere, LLC*, U.S. District Court for the Northern District of Illinois, Case No. 08CV06337, Mar. 27, 2009, 2 pages.

Exhibit 1 to Defendant-Counterclaimant Alere, LLC's First Amended Answer and Counterclaims, *Healthways, Inc.* v. *Alere, LLC*, U.S. District Court for the Northern District of Illinois, Case No. 08CV06337, Sep. 24, 2009, 2 pages.

Exhibit 10 to Alere LLC's Opposition to Plaintiffs' Partial Motion for Judgment on the Pleadings Pursuant to Rule 12(c) and Rule 9(b), *Healthways, Inc.* v. *Alere, LLC*, U.S. District Court for the Northern District of Illinois, Case No. 08CV06337, Sep. 24, 2009, 5 pages.

Exhibit 2 to Alere LLC's Opposition to Plaintiffs' Partial Motion for Judgment on the Pleadings Pursuant to Rule 12(c) and Rule 9(b), *Healthways, Inc.* v. *Alere, LLC*, U.S. District Court for the Northern District of Illinois, Case No. 08CV06337, Sep. 24, 2009, 4 pages.

Exhibit 2 to Defendant-Counterclaimant Alere, LLC's First Amended Answer and Counterclaims, *Healthways, Inc.* v. *Alere, LLC*, U.S. District Court for the Northern District of Illinois, Case No. 08CV06337, Sep. 24, 2009, 5 pages.

Exhibit 3 to Alere LLC's Opposition to Plaintiffs' Partial Motion for Judgment on the Pleadings Pursuant to Rule 12(c) and Rule 9(b), Alere LLC's First Supplemental Objections and Responses to Plaintiffs' Second Set of Interrogatories (No. 9-10), *Healthways, Inc.* v. *Alere, LLC*, U.S. District Court for the Northern District of Illinois, Case No. 08CV06337, Sep. 24, 2009, 62 pages.

Exhibit 3 to Declaration of Goutam Patnaik in Support of Defendant and Counterclaimant Alere, LLC's Motion to Compel Plaintiff Healthways, Inc.'s Response to Interrogatory No. 2, or Preclude Healthway's Future Disclosure of or Reliance on Any Commercial Embodiments, *Healthways, Inc.* v. *Alere, LLC*, U.S. District Court for the Northern District of Illinois, Case No. 08CV06337, Mar. 27, 2009, 3 pages.

Exhibit 3 to Defendant-Counterclaimant Alere, LLC's First Amended Answer and Counterclaims, *Healthways, Inc.* v. *Alere, LLC*, U.S. District Court for the Northern District of Illinois, Case No. 08CV06337, Sep. 24, 2009, 6 pages.

Exhibit 4 to Declaration of Goutam Patnaik in Support of Defendant and Counterclaimant Alere, LLC's Motion to Compel Plaintiff Healthways, Inc.'s Response to Interrogatory No. 2, or Preclude Healthway's Future Disclosure of or Reliance on Any Commercial Embodiments, *Healthways, Inc.* v. *Alere, LLC*, U.S. District Court for the Northern District of Illinois, Case No. 08CV06337, Mar. 27, 2009, 9 pages.

Exhibit 4 to Defendant-Counterclaimant Alere, LLC's First Amended Answer and Counterclaims, *Healthways, Inc.* v. *Alere, LLC*, U.S. District Court for the Northern District of Illinois, Case No. 08CV06337, Sep. 24, 2009, 2 pages.

Exhibit 5 to Declaration of Goutam Patnaik in Support of Defendant and Counterclaimant Alere, LLC's Motion to Compel Plaintiff Healthways, Inc.'s Response to Interrogatory No. 2, or Preclude Healthway's Future Disclosure of or Reliance on Any Commercial Embodiments, *Healthways, Inc.* v. *Alere, LLC*, U.S. District Court for the Northern District of Illinois, Case No. 08CV06337, Mar. 27, 2009, 3 pages.

Exhibit 5 to Defendant-Counterclaimant Alere, LLC's First Amended Answer and Counterclaims, *Healthways, Inc.* v. *Alere, LLC*, U.S. District Court for the Northern District of Illinois, Case No. 08CV06337, Sep. 24, 2009, 3 pages.

Exhibit 8 to Alere LLC's Opposition to Plaintiffs' Partial Motion for Judgment on the Pleadings Pursuant to Rule 12(c) and Rule 9(b), *Healthways, Inc.* v. *Alere, LLC*, U.S. District Court for the Northern District of Illinois, Case No. 08CV06337, Sep. 24, 2009, 3 pages.

Exhibit 9 to Alere LLC's Opposition to Plaintiffs' Partial Motion for Judgment on the Pleadings Pursuant to Rule 12(c) and Rule 9(b), *Healthways, Inc.* v. *Alere, LLC*, U.S. District Court for the Northern District of Illinois, Case No. 08CV06337, Sep. 24, 2009, 8 pages.

Exhibit A to Defendant-Counterclaimaint Alere LLC's Agreed Motion for Leave to Replace its Opposition to Plaintiffs' Partial Motion for Judgment on the Pleadings Pursuant to Rule 12(c) and Rule 9(b) and Exhibit 3 to its Opposition with Redacted Versions, Alere LLC's Opposition to Plaintiffs' Partial Motion for Judgment on the Pleadings Pursuant to Rule 12(c) and Rule 9(b), Redacted, *Healthways, Inc.* v. *Alere, LLC*, U.S. District Court for the Northern District of Illinois, Case No. 08CV06337, Sep. 24, 2009, 21 pages.

Exhibit A to Defendant-Counterclaimant Alere, LLC's Alternative Motion for Leave to File First Amended Answer and Counterclaims, Defendant-Counterclaimant Alere, LLC's First Amended Answer and Counterclaims, *Healthways, Inc.* v. *Alere, LLC*, U.S. District Court for the Northern District of Illinois, Case No. 08CV06337, Sep. 24, 2009, 126 pages.

Exhibit A to Defendant-Counterclaimant Alere, LLC's Unopposed Motion for Leave to Replace its Memorandum in Support of its Alternative Motion for Leave to File First Amended Answer and Counterclaims and First Amended Answer and Counterclaims with Redacted Versions, Defendant-Counterclaimant Counterclaimant Alere, LLC's Memorandum in Support of its Alternative Motion for Leave to File First Amended Answer and Counterclaims, Redacted, *Healthways, Inc.* v. *Alere, LLC*, U.S. District Court for the Northern District of Illinois, Case No. 08CV06337, Sep. 24, 2009, 18 pages.

Exhibit A, Part 1 to Joint Claim Construction Statement, *Healthways, Inc.* v. *Alere, LLC*, U.S. District Court for the Northern District of Illinois, Case No. 08CV06337, Aug. 10, 2009, 15 pages.

Exhibit A, Part 1 to Revised Joint Claim Construction Statement, *Healthways, Inc.* v. *Alere, LLC*, U.S. District Court for the Northern District of Illinois, Case No. 08CV06337, Sep. 4, 2009, 15 pages.

Exhibit A, Part 2 to Joint Claim Construction Statement, *Healthways, Inc.* v. *Alere, LLC*, U.S. District Court for the Northern District of Illinois, Case No. 08CV06337, Aug. 10, 2009, 15 pages.

Exhibit A, Part 2 to Revised Joint Claim Construction Statement, *Healthways, Inc.* v. *Alere, LLC*, U.S. District Court for the Northern District of Illinois, Case No. 08CV06337, Sep. 4, 2009, 15 pages.

Exhibit A, Part 3 to Joint Claim Construction Statement, *Healthways, Inc.* v. *Alere, LLC*, U.S. District Court for the Northern District of Illinois, Case No. 08CV06337, Aug. 10, 2009, 17 pages.

Exhibit A, Part 3 to Revised Joint Claim Construction Statement, *Healthways, Inc.* v. *Alere, LLC*, U.S. District Court for the Northern District of Illinois, Case No. 08CV06337, Sep. 4, 2009, 17 pages.

Exhibit B to Defendant-Counterclaimaint Alere LLC's Agreed Motion for Leave to Replace its Opposition to Plaintiffs' Partial Motion for Judgment on the Pleadings Pursuant to Rule 12(c) and Rule 9(b) and Exhibit 3 to its Opposition with Redacted Versions, Alere LLC's First Supplemental Objections and Responses to Plaintiffs' Second Set of Interrogatories (No. 9-10), Redacted, *Healthways, Inc.* v. *Alere, LLC*, U.S. District Court for the Northern District of Illinois, Case No. 08CV06337, Sep. 24, 2009, 63 pages.

Exhibit B to Defendant-Counterclaimant Alere, LLC's Unopposed Motion for Leave to Replace its Memorandum in Support of its Alternative Motion for Leave to File First Amended Answer and Counterclaims and First Amended Answer and Counterclaims with Redacted Versions, Defendant-Counterclaimant Counterclaimant Alere, LLC's First Amended Answer and Counterclaims, Redacted, *Healthways, Inc.* v. *Alere, LLC*, U.S. District Court for the. Northern District of Illinois, Case No. 08CV06337, Sep. 24, 2009, 127 pages.

Exhibit B to Joint Claim Construction Statement, *Healthways, Inc.* v. *Alere, LLC*, U.S. District Court for the Northern District of Illinois, Case No. 08CV06337, Aug. 10, 2009, 24 pages.

Exhibit B to Revised Joint Claim Construction Statement, *Healthways, Inc.* v. *Alere, LLC*, U.S. District Court for the Northern District of Illinois, Case No. 08CV06337, Sep. 4, 2009, 24 pages.

Exhibit C to Joint Claim Construction Statement, *Healthways, Inc.* v. *Alere, LLC*, U.S. District Court for the Northern District of Illinois, Case No. 08CV06337, Aug. 10, 2009, 8 pages.

Exhibit C to Revised Joint Claim Construction Statement, *Healthways, Inc.* v. *Alere, LLC*, U.S. District Court for the Northern District of Illinois, Case No. 08CV06337, Sep. 4, 2009, 7 pages.

Exhibit D to Joint Claim Construction Statement, *Healthways, Inc.* v. *Alere, LLC*, U.S. District Court for the Northern District of Illinois, Case No. 08CV06337, Aug. 10, 2009, 8 pages.

Exhibit D to Memorandum of Law in Support of Plaintiffs' Partial Motion for Judgment on the Pleadings Pursuant to Rule 12(C) and Rule 9(B), *Healthways, Inc.* v. *Alere, LLC*, U.S. District Court for the Northern District of Illinois, Case No. 08CV06337, Aug. 31, 2009, 3 pages.

Exhibit D to Revised Joint Claim Construction Statement, *Healthways, Inc.* v. *Alere, LLC*, U.S. District Court for the Northern District of Illinois, Case No. 08CV06337, Sep. 4, 2009, 8 pages.

Exhibit E to Joint Claim Construction Statement, *Healthways, Inc.* v. *Alere, LLC*, U.S. District Court for the Northern District of Illinois, Case No. 08CV06337, Aug. 10, 2009, 8 pages.

Exhibit E to Memorandum of Law in Support of Plaintiffs' Partial Motion for Judgment on the Pleadings Pursuant to Rule 12(C) and Rule 9(B), *Healthways, Inc.* v. *Alere, LLC*, U.S. District Court for the Northern District of Illinois, Case No. 08CV06337, Aug. 31, 2009, 3 pages.

Exhibit E to Revised Joint Claim Construction Statement, *Healthways, Inc.* v. *Alere, LLC*, U.S. District Court for the Northern District of Illinois, Case No. 08CV06337, Sep. 4, 2009, 8 pages.

Exhibit F to Joint Claim Construction Statement, *Healthways, Inc.* v. *Alere, LLC*, U.S. District Court for the Northern District of Illinois, Case No. 08CV06337, Aug. 10, 2009, 7 pages.

Exhibit F to Memorandum of Law in Support of Plaintiffs' Partial Motion for Judgment on the Pleadings Pursuant to Rule 12(C) and Rule 9(B), *Healthways, Inc.* v. *Alere, LLC*, U.S. District Court for the Northern District of Illinois, Case No. 08CV06337, Aug. 31, 2009, 3 pages.

Exhibit F to Revised Joint Claim Construction Statement, *Healthways, Inc.* v. *Alere, LLC*, U.S. District Court for the Northern District of Illinois, Case No. 08CV06337, Sep. 4, 2009, 7 pages.

Exhibit G to Joint Claim Construction Statement, *Healthways, Inc.* v. *Alere, LLC*, U.S. District Court for the Northern District of Illinois, Case No. 08CV06337, Aug. 10, 2009, 7 pages.

Exhibit G to Memorandum of Law in Support of Plaintiffs' Partial Motion for Judgment on the Pleadings Pursuant to Rule 12(C) and Rule 9(B), *Healthways, Inc.* v. *Alere, LLC*, U.S. District Court for the Northern District of Illinois, Case No. 08CV06337, Aug. 31, 2009, 2 pages.

Exhibit G to Revised Joint Claim Construction Statement, *Healthways, Inc.* v. *Alere, LLC*, U.S. District Court for the Northern District of Illinois, Case No. 08CV06337, Sep. 4, 2009, 7 pages.

Exhibit H to Joint Claim Construction Statement, *Healthways, Inc.* v. *Alere, LLC*, U.S. District Court for the Northern District of Illinois, Case No. 08CV06337, Aug. 10, 2009, 9 pages.

Exhibit H to Revised Joint Claim Construction Statement, *Healthways, Inc.* v. *Alere, LLC*, U.S. District Court for the Northern District of Illinois, Case No. 08CV06337, Sep. 4, 2009, 9 pages.
Joint Claim Construction Statement, *Healthways, Inc.* v. *Alere, LLC*, U.S. District Court for the Northern District of Illinois, Case No. 08CV06337, Aug. 10, 2009, 60 pages.
Memorandum of Law in Support of Plaintiffs' Partial Motion for Judgment on the Pleadings Pursuant to Rule 12(C) and Rule 9(B), *Healthways, Inc.* v. *Alere, LLC*, U.S. District Court for the Northern District of Illinois, Case No. 08CV06337, Aug. 31, 2009, 12 pages.
Revised Joint Claim Construction Statement, *Healthways, Inc.* v. *Alere, LLC*, U.S. District Court for the Northern District of Illinois, Case No. 08CV06337, Sep. 4, 2009, 58 pages.
Request for Ex Parte Reexamination filed Oct. 8, 2009 of USP 6,113,540, issued Sep. 5, 2000.
Complaint, *Healthways, Inc.* v. *Alere, LLC*, U.S. District Court for the Northern District of Illinois, Case No. 08CV06337, Nov. 4, 2008, 14 pages.
Alere's Answer and Counterclaims, *Healthways, Inc.* v. *Alere, LLC*, U.S. District Court for the Northern District of Illinois, Case No. 08CV06337, Dec. 9, 2008, 29 pages.
Memorandum of Law in Support of Plaintiffs' Motion to Dismiss under Rule 12(b)(6) or Rule 9(b), *Healthways, Inc.* v. *Alere, LLC*, U.S. District Court for the Northern District of Illinois, Case No. 08CV06337, Dec. 29, 2008, 9 pages.
Plaintiffs' Reply to Alere's Counterclaims, *Healthways, Inc.* v. *Alere, LLC*, U.S. District Court for the Northern District of Illinois, Case No. 08CV06337, Dec. 29, 2008, 10 pages.
Alere's First Amended Answer and Counterclaims, *Healthways, Inc.* v. *Alere, LLC*, U.S. District Court for the Northern District of Illinois, Case No. 08CV06337, Jan. 6, 2009, 28 pages.
Alere's First Amended Answer and Counterclaims, *Healthways, Inc.* v. *Alere, LLC*, U.S. District Court for the Northern District of Illinois, Case No. 08CV06337, Jan. 8, 2009, 30 pages.
Plaintiffs' Reply to Alere's First Amended Counterclaims, *Healthways, Inc.* v. *Alere, LLC*, U.S. District Court for the Northern District of Illinois, Case No. 08CV06337, Jan. 9, 2009, 11 pages.
First Amended Complaint, *Healthways, Inc.* v. *Alere, LLC*, U.S. District Court for the Northern District of Illinois, Case No. 08CV06337, Jan. 15, 2009, 15 pages.
Alere's Answer to First Amended Complaint and Counterclaims, *Healthways, Inc.* v. *Alere, LLC*, U.S. District Court for the Northern District of Illinois, Case No. 08CV06337, Jan. 22, 2009, 32 pages.
Exhibit 1 to Alere's Answer to First Amended Complaint and Counterclaims, *Healthways, Inc.* v. *Alere, LLC*, U.S. District Court for the Northern District of Illinois, Case No. 08CV06337, Jan. 22, 2009, 2 pages.
Exhibit 2 to Alere's Answer to First Amended Complaint and Counterclaims, *Healthways, Inc.* v. *Alere, LLC*, U.S. District Court for the Northern District of Illinois, Case No. 08CV06337, Jan. 22, 2009, 5 pages.
Exhibit 3 to Alere's Answer to First Amended Complaint and Counterclaims, *Healthways, Inc.* v. *Alere, LLC*, U.S. District Court for the Northern District of Illinois, Case No. 08CV06337, Jan. 22, 2009, 6 pages.
Exhibit 4 to Alere's Answer to First Amended Complaint and Counterclaims, *Healthways, Inc.* v. *Alere, LLC*, U.S. District Court for the Northern District of Illinois, Case No. 08CV06337, Jan. 22, 2009, 2 pages.
Exhibit 5 to Alere's Answer to First Amended Complaint and Counterclaims, *Healthways, Inc.* v. *Alere, LLC*, U.S. District Court for the Northern District of Illinois, Case No. 08CV06337, Jan. 22, 2009, 3 pages.
Replacement Exhibit 1 to Alere's Answer to First Amended Complaint and Counterclaims, *Healthways, Inc.* v. *Alere, LLC*, U.S. District Court for the Northern District of Illinois, Case No. 08CV06337, Jan. 23, 2009, 4 pages.
Plaintiffs' Reply to Alere Medical, Inc.'s Counterclaims, *Healthways, Inc.* v. *Alere, LLC*, U.S. District Court for the Northern District of Illinois, Case No. 08CV06337, Feb. 10, 2009, 11 pages.
Plaintiffs' Amended Reply to Alere Medical, Inc.'s Counterclaims, *Healthways, Inc.* v. *Alere, LLC*, U.S. District Court for the Northern District of Illinois, Case No. 08CV06337, Feb. 10, 2009, 11 pages.
Alere, LLC's Objections and Answers to Plaintiffs First Set of Interrogatories (Nos. 1-8), *Healthways, Inc.* v. *Alere, LLC*, U.S. District Court for the Northern District of Illinois, Case No. 08CV06337, Feb. 11, 2009, 30 pages.
Alere, LLC's Objections and Answers to Plaintiffs' Second Set of Interrogatories (No. 9-10), *Healthways, Inc.* v. *Alere, LLC*, U.S. District Court for the Northern District of Illinois, Case No. 08CV06337, Mar. 2, 2009, 10 pages.
Alere, LLC's First Supplemental Objections and Responses to Plaintiffs First Set of Interrogatories (Nos. 1-8), *Healthways, Inc.* v. *Alere, LLC*, U.S. District Court for the Northern District of Illinois, Case No. 08CV06337, Mar. 3, 2009, 23 pages.
Exhibit B to Alere, LLC's First Supplemental Objections and Responses to Plaintiffs First Set of Interrogatories (Nos. 1-8), *Healthways, Inc.* v. *Alere, LLC*, U.S. District Court for the Northern District of Illinois, Case No. 08CV06337, Mar. 3, 2009, 18 pages.
Exhibit C to Alere, LLC's First Supplemental Objections and Responses to Plaintiffs First Set of Interrogatories (Nos. 1-8), *Healthways, Inc.* v. *Alere, LLC*, U.S. District Court for the Northern District of Illinois, Case No. 08CV06337, Mar. 3, 2009, 5 pages.
Exhibit D to Alere, LLC's First Supplemental Objections and Responses to Plaintiffs First Set of Interrogatories (Nos. 1-8), *Healthways, Inc.* v. *Alere, LLC*, U.S. District Court for the Northern District of Illinois, Case No. 08CV06337, Mar. 3, 2009, 15 pages.
Exhibit E to Alere, LLC's First Supplemental Objections and Responses to Plaintiffs First Set of Interrogatories (Nos. 1-8), *Healthways, Inc.* v. *Alere, LLC*, U.S. District Court for the Northern District of Illinois, Case No. 08CV06337, Mar. 3, 2009, 12 pages.
Exhibit F to Alere, LLC's First Supplemental Objections and Responses to Plaintiffs First Set of Interrogatories (Nos. 1-8), *Healthways, Inc.* v. *Alere, LLC*, U.S. District Court for the Northern District of Illinois, Case No. 08CV06337, Mar. 3, 2009, 61 pages.
Exhibit G to Alere, LLC's First Supplemental Objections and Responses to Plaintiffs First Set of Interrogatories (Nos. 1-8), *Healthways, Inc.* v. *Alere, LLC*, U.S. District Court for the Northern District of Illinois, Case No. 08CV06337, Mar. 3, 2009, 31 pages.
Exhibit H to Alere, LLC's First Supplemental Objections and Responses to Plaintiffs First Set of Interrogatories (Nos. 1-8), *Healthways, Inc.* v. *Alere, LLC*, U.S. District Court for the Northern District of Illinois, Case No. 08CV06337, Mar. 3, 2009, 13 pages.
Exhibit I-1 to Alere, LLC's First Supplemental Objections and Responses to Plaintiffs First Set of Interrogatories (Nos. 1-8), *Healthways, Inc.* v. *Alere, LLC*, U.S. District Court for the Northern District of Illinois, Case No. 08CV06337, Mar. 3, 2009, 83 pages.
Exhibit I-2 to Alere, LLC's First Supplemental Objections and Responses to Plaintiffs First Set of Interrogatories (Nos. 1-8), *Healthways, Inc.* v. *Alere, LLC*, U.S. District Court for the Northern District of Illinois, Case No. 08CV06337, Mar. 3, 2009, 87 pages.
Exhibit J to Alere, LLC's First Supplemental Objections and Responses to Plaintiffs First Set of Interrogatories (Nos. 1-8), *Healthways, Inc.* v. *Alere, LLC*, U.S. District Court for the Northern District of Illinois, Case No. 08CV06337, Mar. 3, 2009, 22 pages.
Exhibit K to Alere, LLC's First Supplemental Objections and Responses to Plaintiffs First Set of Interrogatories (Nos. 1-8), *Healthways, Inc.* v. *Alere, LLC*, U.S. District Court for the Northern District of Illinois, Case No. 08CV06337, Mar. 3, 2009, 41 pages.
Exhibit L to Alere, LLC's First Supplemental Objections and Responses to Plaintiffs First Set of Interrogatories (Nos. 1-8), Healthways, Inc. v. Alere, LLC, U.S. District Court for the Northern District of Illinois, Case No. 08CV06337, Mar. 3, 2009, 18 pages.
Alere LLC's Counterclaims, *Healthways, Inc.* v. *Alere, LLC*, U.S. District Court for the Northern District of Illinois, Case No. 08CV06337, Mar. 4, 2009, 10 pages.
Exhibit 12 to Alere LLC's Counterclaims, *Healthways, Inc.* v. *Alere, LLC*, U.S. District Court for the Northern District of Illinois, Case No. 08CV06337, Mar. 4, 2009, 2 pages.
Exhibit 13 to Alere LLC's Counterclaims, *Healthways, Inc.* v. *Alere, LLC*, U.S. District Court for the Northern District of Illinois, Case No. 08CV06337, Mar. 4, 2009, 5 pages.
Exhibit 14 to Alere LLC's Counterclaims, *Healthways, Inc.* v. *Alere, LLC*, U.S. District Court for the Northern District of Illinois, Case No. 08CV06337, Mar. 4, 2009, 6 pages.

Exhibit 15 to Alere LLC's Counterclaims, *Healthways, Inc.* v. *Alere, LLC*, U.S. District Court for the Northern District of Illinois, Case No. 08CV06337, Mar. 4, 2009, 2 pages.

Exhibit 16 to Alere LLC's Counterclaims, *Healthways, Inc.* v. *Alere, LLC*, U.S. District Court for the Northern District of Illinois, Case No. 08CV06337, Mar. 4, 2009, 3 pages.

Applied Medical Informatics, Inc., "Medical House Call™ Interactive Home Medical Guide & Symptom Analysis", Applied Medical Informatics, 1995, pp. 24-Jan., Salt Lake City, UT.

Barnett et al., A computer-based medical information system for ambulatory care, Proc. IEEE, 1979, Issue 67, pp. 1226-1237.

Bouhaddou et al., An interactive patient information and education system (Medical HouseCall) based on a physician expert system (Iliad), Medinfo, 1995, vol. Pt 2, Issue 8, pp. 1181-1185, Vancouver, Canada.

Bouhaddou et al., AMIA, Inc., pp. 742-746, 1995, "Iliad and Medical House Call: evaluating the impact of common sense knowledge on the diagnostic accuracy of a medical expert system".

Collen, Machine diagnosis from a multiphasic screening program, Proceedings of 5$^{th}$ IBM Medical Symposium at 131, 1963.

Cope, For well-connected in study, computer's diagnosis is just a phone call away, Minneappolis Star-Tribune, Mar. 1992, pp. 03E.

Crossman, Confused? Take two aspirin and call up advisor, New Jersey Record, Apr. 1992, pp. B02.

Dawson, Sun, Microsoft battle over Net computing, Multichannel News, Nov. 1996.

Gorry et al., Decision analysis as the basis for computer-aided management of acute renal failure, Am. J. Med., Oct. 1973, vol. 3, Issue 55, pp. 473-484.

Lai, Abstraction models at system level for interactive multimedia scripting, Master's Thesis, Massachusetts Institute of Technology, May 1995, Boston.

Magnet, Who's winning the information revolution, Fortune, Nov. 30, 1992, vol. 12, Issue 126, pp. 110-117.

Mallya et al., Correlation in rheumatoid arthritis of concentrations of plasma C3d, serum rheumatoid factor, immune complexes and C-reactive protein with each other and with clinical features of disease activity., Clin. Exp. Immunol., 1982, Issue 48, pp. 747-753.

Markoff, Making the PC come alive, New York Times, Sep. 1995.

Miller, Dial 1-900 for doctor, Newsweek, Oct. 1991.

Okada, Medical data base system with an ability of automated diagnosis, Computer Programs in Biomedicine, Sep. 1977, vol. 3, Issue 7, pp. 163-170.

Olson et al., 21$^{st}$ century learning and health care in the home: creating a national telecommunications network, IAF/CRI, Jan. 1992.

Pauker et al., Towards the simulation of clinical cognition: taking a present illness by computer, Am. J. Med., Jun. 1976, vol. 7, Issue 60, pp. 981-996.

Riordan, Patents; Prodigy's patent is being debated as a possible threat to Sun Microsystems' Java language, New York Times, Feb. 1996.

Roberts, Dr. Schueler's home medical advisor 2.0, Compute!, Oct. 1992, Issue 145, pp. 106.

Shannon, Peripherals; choosing a college, New York Times, Jan. 1989.

Shannon, "Peripherals; advice on a disk: the doctor is really in", New York Times, Jul. 14, 1992 at C7.

Shannon, "Peripherals; Doctor, I have this funny pain . . . ", New York Times, Nov. 3, 1992.

Stearn et al., A statistical analysis of subjective and objective methods of evaluating fabric handle Part 2: Relationship between subjective and objective measurements, Journal of the Textile Machinery Society of Japan, 1988, vol. 2, Issue 34, pp. 39-46.

Szolovits et al., Categorical and probabilistic reasoning in medical diagnosis, Artificial Intelligence, Aug. 1978, vol. 1&2, Issue 11, pp. 115-144.

Tedesco, Microsoft, Intel and Sun advance NC visions, Broadcasting & Cable, Nov. 1996.

Templeton, Medical software that makes house calls, BusinessWeek, Jun. 1992, Issue 3720.

Vaughn et al., Effective algorithm-based triage and self-care protocols: quality medicine at lower costs, Ann. Emerg. Med., Jan. 1980, vol. 1, Issue 9, pp. 31-36.

Warner, Knowledge sectors for logical processing of patient data in the help system, Proc. IEEE, 1978.

Wijkstra et al., Relation of lung function, maximal inspiratory pressure, dyspnoea, and quality of life with exercise capacity in patients with chronic obstructive pulmonary disease, Thorax, May 1994, vol. 5, Issue 49, pp. 468-472.

Zallen, Member-centered managed care and the new media, ed. Linda M. Harris, in Health and the New Media, 1995.

International Search Report dated Aug. 12, 1998 in PCT/US98/04865, filed Mar. 13, 1998.

Written Opinion (Rule 66) dated Dec. 15, 1998 in PCT/US98/04865, filed Mar. 13, 1998.

International Preliminary Examination Report dated Jun. 11, 1999 in PCT/US98/04865, filed Mar. 13, 1998.

JP Office Action dated Apr. 24, 2007 in Japanese Patent Application No. 539802/98, filed Mar. 13, 1998.

CN Office Action dated May 18, 2007 in Chinese Patent Application No. 200410057537.8, filed Mar. 13, 1998.

CN Office Action dated Jan. 4, 2008 in Chinese Patent Application No. 200410057537.8, filed Mar. 13, 1998.

EP Office Action dated Jan. 10, 2006 in European Patent Application No. 98911601.7, filed Mar. 13, 1998.

AU Office Action dated Jul. 1, 2005 in Australian Patent Application No. 2003235078, filed Aug. 19, 2003.

CA Office Action dated Feb. 13, 2006 in Canadian Patent Application No. 2,284,168, filed Mar. 13, 1998.

CA Office Action dated Apr. 15, 2008 in Canadian Patent Application No. 2,284,168, filed Mar. 13, 1998.

JP Office Action dated Aug. 18, 2008 in Japanese Patent Appliation No. 539802/98 (under Appeal No. 2008-005314).

The Alpha Media Catalog, Advertisement, Oct. 1993, "Physician's Database Manager" and "Iliad.".

Arthur D. Little, Inc., Acorn Park, Cambridge, MA, Jul. 1992, "Can Telecommunications Help Solve America's Health Care Problems?" Summary.

Arthur D. Little, Inc., Acorn Park, Cambridge, MA, Jul. 1992, "Telecommunications: Can It Help Solve America's Health Care Problems?" pp. 1-116.

Becher, Ernst, "Fernmeldewesen für soziale Dienste in Entwicklungsländern," NTZ, 33:304, 1980.

Bergman, "Computers make 'house calls' to patients; Harvard Community Health Plan offers computerized information service to patients," J American Hospital Association, 67(10): 52, May 20, 1993.

Bowden, K.F. et al., Information Processing, 71:1398-1406, 1972, "Data structures for general practice records.".

Cimino, James J. et al., IEEE/Ninth Annual Conference of the Engineering in Medicine and Biology Society, 1987, "DXplain: An interactive knowledge base for assistance in medical diagnostic decisions.".

Conrath, David W. et al., IEEE Transactions on Communications, COM-23(10):1119-1126, 1975, "A preliminary evaluation of alternative telecommunication systems for the delivery of primary health care to remote areas."

Currid, Cheryl, PC Week, Sep. 17, 1990, "Risky Business: doctors, lawyers shy away from computer technology."

Dahmer J., "Anamnese und Befund", Georg Thieme Verlag, 1981, pp. 22-25, 44-47, 292-295 and 371-375.

Dahmer J., Der Denkprozess "Vom Symptom zur Diagnose", Anamnese und Befund, Georg Thieme Verlag, 1981, p. 3.

Doheny, Kathleen, La Times Magazine, p. 8, Aug. 4, 1991, "Hack attack."

Fisher et al., "Great Expectations: Expectation-based reasoning in Medical Diagnosis," Proceedings of the 12th Annual Symposium on Computer Applications in Medical Care, Nov. 6, 1988, pp. 38-42.

Frenger, Paul, IEEE Frontiers of Computers in Medicine, 1982, "Details of a database management system for a telephone medical consultation service."

Frenger, Paul, ISA, pp. 103-107, 1983, "Advanced techniques used to create a telephone medical consultation service."

Freudenheim, Milt, The New York Times, Business and Health, p. D2, Jun. 25, 1991, "Computer says take 2 aspirin."

Goldbard, Gary A, Class Notes, Tulane Medicine, Tulane University Medical Center, 1430 Tulane Avenue, New Orleans, LA 70112-2699, p. 26, Jun. 1991.

Gome, Amanda, Herald-Sun, p. 13, Nov. 19, 1991, "A picture of success."

Gorry, G. Anthony, Bulletin of the Operations Research Society of America, 19(2), 1971, "FA6.3 Automating Judgmental decision making in medicine."

"Harvard Community Health Plan Testing Computerized Service that Answers Health-Care Questions," Technical Computing, 6(9), Aug. 1991.

Hudson et al., "Human-Computer Interaction in a Medical Decision Support System." IEEE Computer Society Press, 2: 429-435, 1989.

Kerr, Jennifer, San Diego Union-Tribune, p. A3, Sunday, Jul. 18, 1993, "Phone is link to health-care information."

Larsson et al., "An Expert System Interface for an Identification Program," Automatica, Pergamon Press Ltd., Oxford, GB., 27(6): 919-930, 1991.

Laughlin, Michael L., ed., Computers in Health Care, pp. 32-37, Nov. 1992, "Telecommunications may offer poor a 'road' to healthcare."

Levin, Carol, PC Magazine, p. 32, Mar. 16, 1993, "Patient, heal thyself".

Mallory, Jim, Newsbytes, American Association for the Advancement of Science, Panel Discussion, Feb. 19, 1992, "Computers now giving medical advice."

McDonald et al., Environmental Science and Policy Institute, 1992, "Health in the Information Age: The Emergence of Health Oriented Telecommunication Applications."

"Netscape & Sun Announce Javascript The Open, Cross-Platform Object Scripting Language for Enterprise Networks and the Internet", Press Release, Dec. 4, 1995, web at http://java.sun.com/pr/1995/12/pr951204-03.html. (10 pages).

New York Times, p. 18, Jul. 13, 1991, "System helps doctors keep up to date."

O'Neil, et al., Conference Paper, IEEE Coll. On Computer Based Diagnosis, p. 8/1-4, 1989, "Diagnostic Support in the Oxford System of Medicine."

Rose, J, ed., "Progress of Cybernetics, vol. 2, Cybernetics and Industry, Social and Economic Consequences, Cybernetics and Artifacts," Proceedings of the First International Congress of Cybernetics, London, Gordon and Breach Science Publishers, pp. 803-811, 1969.

Rymon, et al., IEEE Transactions on Systems, Man, and Cybernetics, 23(6):1551-1560, Nov./Dec. 1993, "Progressive Horizon Planning-Planning Exploratory-Corrective Behavior."

Sacks, Terry, San Diego Union-Tribune, p. E-16, Mar. 24, 1992, "Pocket computer may cure technology-shy physicians."

Salvans, P. Ferrer and Alonso L. Vallès, Computer Biol. Med., 20(6):433-443, 1990, "An epidemiologic approach to computerized medical diagnosis—AEDMI program."

San Diego Emergency Physicians Society, Meeting Minutes, Regular Oct. 1991 Meeting, P.O. Box 16685, San Diego, CA 92176, first page.

Schild, W. et al., IBM J. Res. Develop., 22(5):518-532, 1978, "Computer-aided diagnosis with an application to endocrinology."

Shapiro, Encyclopedia of Artificial Intelligence, 2nd Edition, vol. 2, pp. 916-926, John Wiley & Sons, Inc., 1992.

Shortliffe, Edward H., Expert Systems and AI Applications, pp. 323-333, 1980, "Consultation system for physicians: the role of artificial intelligence techniques."

Sloane, L., New York Times, p. 16, Jul. 13, 1991, "For round-the-clock diagnosis, just pick up your telephone."

Smothers, R., New York Times, Sep. 16, 1992, "New video technology lets doctors examine patients many miles away."

Starr et al., "Gycon: A Microcomputer Based Gynecological Consultant," Proceed Inter Comp Symposium, Dec. 17-19, 1986, Tainan, Taiwan R.O.C. pp. 1678-1684.

Starr et al., "A microcomputer-based medical expert system shell using a weight/threshold decision mechanism," Proc. Of the 13th Annual Northeast Bioengineering Conference, Mar. 12-13, 1987, pp. 279-281.

Szolovits et al., "Artificial Intelligence in Medical Diagnosis," Ann Intern Med., Jan. 1988, 108(1): 80-87; (pp. 1-12).

Thorpe, C. William et al., "A microcomputer-based interactive cough sound analysis system", Computer Methods and Programs in Biomedicine, Section II, Systems and programs, 36:33-43, 1991.

Wagner, J et al., Conference Paper of Expert Systems and Decision Support in Medicine, 33rd Annual Meeting of the GMDS EFMI Special Topic Meeting, pp. 449-465, Sep. 1988, "A knowledge-based system for interactive medical diagnosis encoding."

Walz, Nancy, The Associated Press, Business News, Jun. 25, 1991, "Computer system aims to wipe out medical paperwork."

Waterman, A Guide to Expert Systems, Addison-Wesley Publishing Co., pp. 46-47 and 272-288, 1986.

Weinstock, Edward, Cover, Avant-Garde, 1984, "An Apple a Day™."

Werner, et al., Conference Paper, IEEE Engineering in Medicine and Biology, 3 pages, 1989, "Interlocutor: Conferring with an Expert Diagnostic Consultant in Geriatric Psychiatry ."

Belzer et al. "Encyclopedia of Computer Science and Technology", Marcel Dekker, Inc. NY (1978) pp. 78-79 and 114-115.

Curtin et al. "Disease Management Information System: Design, Development, Testing, and Clinical Application for Cancer Management", Abstract http://ascobeta.infostreet.com/prof/me/html/abstracts/hre/m_1509.htm (1997).

Gale et al. Medical Diagnosis From Student to Clinician, (1983) pp. 1-22.

Gini et al. "A Serial Model for Computer Assisted Medical Diagnosis", Int J Bio-Med Comp. (1980) 11: 99-113.

Hile et al. "Reliability of an Automated Decision Support System for Behavioral Treatment Planning: Preliminary Results from the Mental Retardation-Expert", Computers in Human Services (1994) 10(4): 19-29.

Medical Computer Consultants' Consortium, Inc. "Disease State Management Software System Product Description", http://www.mc3co.com/DMSS.htm (1997).

Memorial Sloan-Kerrering Cancer Center "Center Develops New System for Disease Management" http://www.mskcc.org/document/cn950601.htm (1997).

JP Office Action dated Feb. 27, 2007 in Japanese Patent Application No. 506146/98, filed Jul. 11, 1997.

* cited by examiner

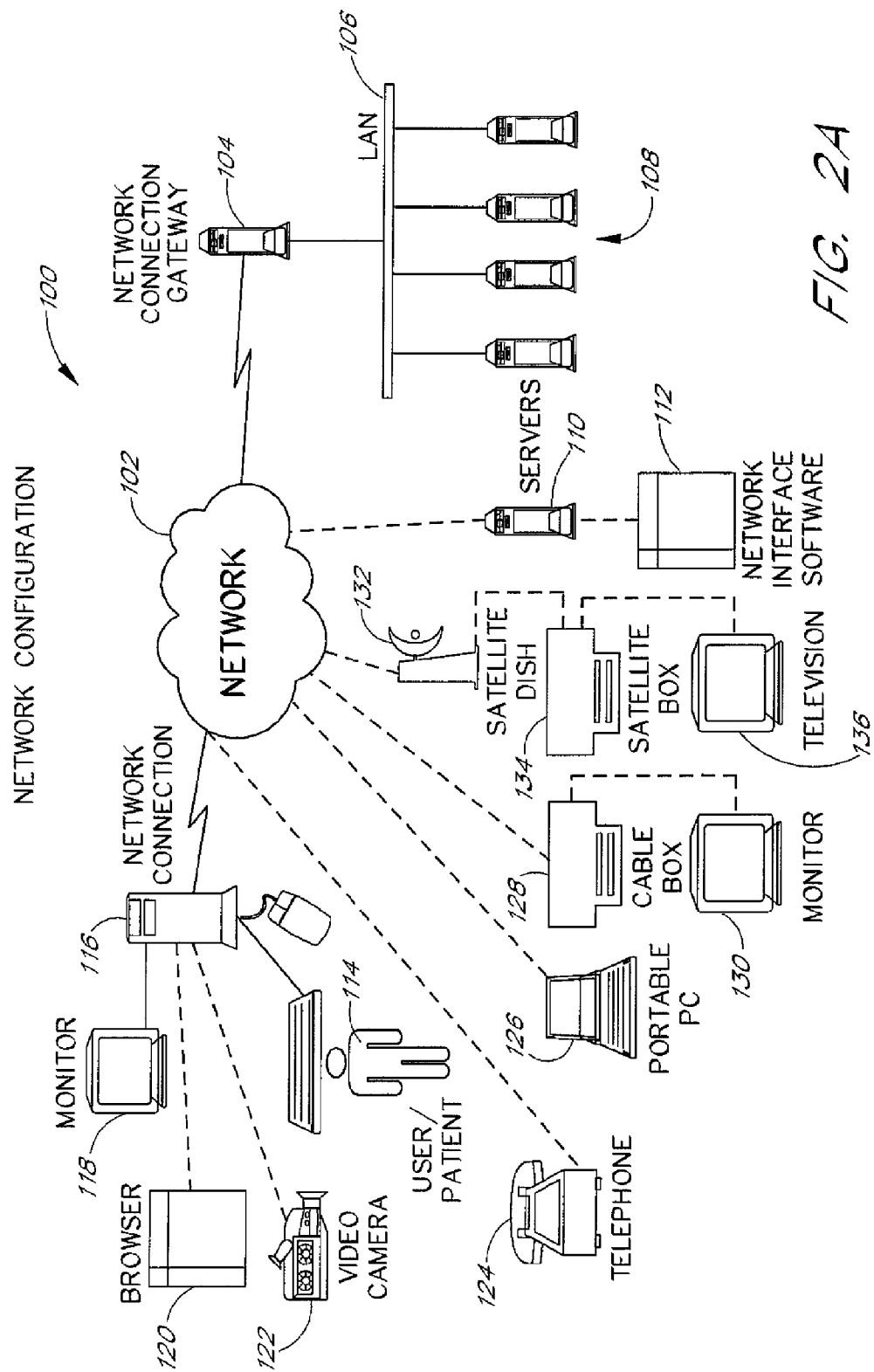

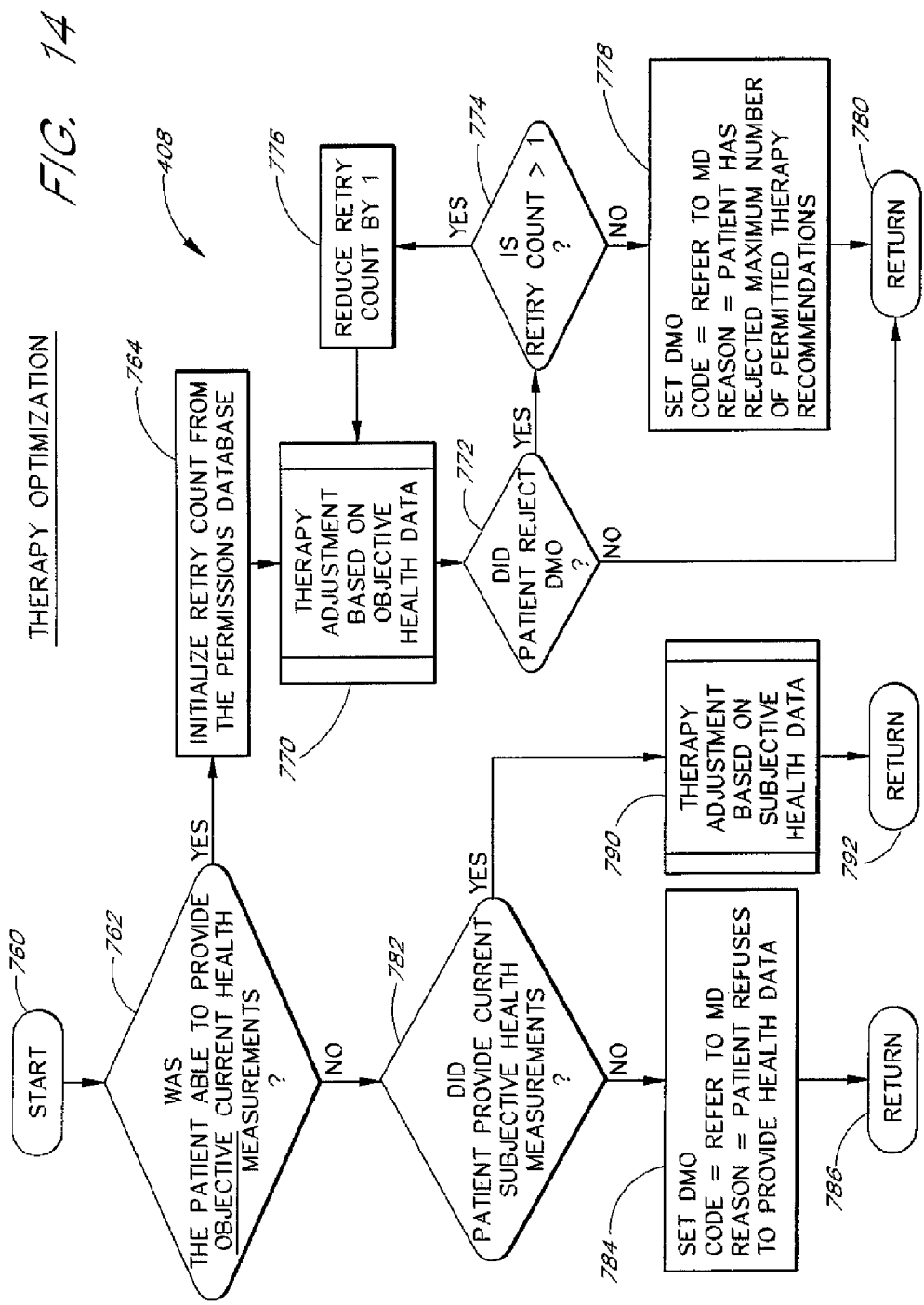

THE CRITICAL CURVE

DISEASE MANAGEMENT SYSTEM AND METHOD INCLUDING PAIN CODE

ASSIGNEE'S APPLICATIONS RELATED BY FILING DATE

This application is a divisional of application Ser. No. 10/261,919, filed Oct. 1, 2002, now U.S. Pat. No. 7,297,108, which is a divisional of application Ser. No. 09/818,187, filed Mar. 26, 2001, now abandoned, which is a divisional of application Ser. No. 09/042,075, filed Mar. 13, 1998, now U.S. Pat. No. 6,234,964, which claims the benefit of provisional Application No. 60/040,522, filed Mar. 13, 1997, all of which are hereby incorporated by reference.

This application is related to application Ser. No. 11/929,472 filed Oct. 30, 2007, and entitled Disease Management System And Method Including Permission Database; application Ser. No. 11/929,836 filed Oct. 30, 2007, and entitled Disease Management System And Method Including Therapy Optimization; application Ser. No. 11/929,609, filed Oct. 30, 2007, and entitled Disease Management System And Method Including Question Version; application Ser. No. 11/933,205, filed Oct. 31, 2007, and entitled Disease Management System And Method Including Therapeutic Alterations Permission Level; application Ser. No. 11/933,150, filed Oct. 31, 2007, and entitled Disease Management System And Method Including Preview Mode; application Ser. No. 11/933,167 filed Oct. 31, 2007, and entitled Disease Management System Including A No Response Method; application Ser. No. 11/930,778, filed Oct. 31, 2007, and entitled Disease Management System And Health Assessment Method; application Ser. No. 11/930,792, filed Oct. 31, 2007, and entitled Disease Management System and Method Including Significant Symptom Filtering; application Ser. No. 11/932,811, filed Oct. 31, 2007, and entitled Disease Management System Operating On A Network; application Ser. No. 11/933,098, filed Oct. 31, 2007, and entitled Disease Management System And Method; and application Ser. No. 11/927,630, filed Oct. 29, 2007, and entitled Disease Management System And Method.

BACKGROUND OF THE INVENTION

1. Field of the Invention

The present invention generally relates to medical knowledge systems, and more specifically, to systems for computerized long-term management of patient diseases.

2. Description of the Related Technology

Health is the ground upon which we lead our lives. Medicine is composed of diagnosis and treatment. Diagnosis means finding the cause of the patient's problem; treating is the application of the best therapy available. However, not all diseases can be completely cured by a treatment regime.

Diseases such as asthma and diabetes may require a regular schedule of treatment, termed therapy, for the duration of a patient's life. In this case, the disease is managed rather than cured. Disease management may be defined as managing a patient with a known diagnosis with the intention of providing patient education and monitoring to prevent symptom flare ups and acute episodes of the disease in order to eliminate costly medical intervention and promote patient well being. The therapy portion of disease management must be custom-tailored to the response of a particular patient since diseased patients may respond differently to the same treatment, e.g., a prescribed dosage and pharmaceuticals.

Since disease management creates reoccurring expenses to society, there is a tremendous desire to reduce costs. One must understand a capitated healthcare system in the extreme to see why the goal is worth achieving. Advocates of a fully capitated system say that everyone will win. Taken to the extreme no one will ever get sick, and doctors will be paid for never seeing patients because there wouldn't be any patients. In a fully capitated system, every person in the world pays a predetermined amount per person per month to health maintenance organizations whose sole purpose is to keep you healthy. This is an admirable goal, but impossible to achieve. However, a realizable goal is to automate the way diseases are managed.

The entire concept of disease management, carried to the extreme, is to visualize a doctor following a patient around for 24 hours a day. Of course, this is an unobtainable solution for the vast majority of the population. To reduce costs, the doctor's knowledge must be disseminated to the general public and one approach might be to not require the physical presence of the doctor at the site of the patient.

Much of medicine is algorithmic. That is, the diagnosis follows a sequence of steps to isolate the cause of the problem. Advanced cardiac life support (ACLS) and advanced trauma life support (ATLS) have shown how much care can be improved by setting standards. Some standards may be translated into medicinal algorithms, which can help set the standard of care for physicians. The concept of telephone medical advice has been proven by nationwide poison control centers, and physicians, particularly pediatricians, have practiced medicine over the telephone since it was invented. In fact, the very first words uttered over the telephone were an appeal for help, for Alexander Graham Bell had just spilled battery acid (for the batteries for the telephone) and said, "Come here, Mr. Watson, I need you" on Mar. 7, 1876. Today's so-called telemedicine remains a one-to-one relationship. The phenomenon of telemedicine depends, in part, on best-practice guidelines helping make the practice of medicine consistent.

Disease management is nothing less than the redesign of the practice of medicine. The problem with medicine was mostly one of information and arrangement of that information. Because of the development of the personal computer and standards, advances can now be made in disease management. In the past, doctors have been the repository of medical information and the ones to "arrange" it so that it had clinical meaning. But these functions can now be performed in an automated way using the "lever" of telecommunication and computer technologies.

Disease management can involve coordinating care for patients across the entire health care continuum from birth to death. Disease management has a program available for every part of everyone's life, including prevention, diagnosis, treatment and rehabilitation. The process involves managing not only the patient with a particular disease, but also the healthy patient. Too often, providers focuses on providing intensive and costly services to patients with acute episodes of disease. Disease management advocates seek a greater focus on preventive, comprehensive care to improve the health of the entire population. In a sense, disease management attempts to take the practice of medicine out of the hands of physicians and puts it into the hands of patients.

Almost all "knowledge based" clinical reasoning could be performed better and more reliability by computers. Technology will drive the democratization of medicine. A system that can automate the practice of medicine, especially in disease management, and which encourages and trains patients to play a major beneficial role in their medical health care is highly desired. Such a system should give a sustainable, substantive, and significant competitive advantage in a capitated health care marketplace. Such a system should be able to automatically identify very critical points in any disease process so that intervention is clinically, economically and humanistically maximized.

SUMMARY OF THE INVENTION

In one embodiment, there is an automated system for encoding a subjective experience of a patient's pain, the system comprising a software function configured to encode a subjective description of a patient's pain to represent a degree or description of pain; and a pain code array, wherein the pain code array comprises encoded numeric values representing a plurality of different aspects of subjective patient descriptions of pain.

In another embodiment, there is a computerized method for encoding a description of a patient's pain into a pain code array, the method comprising storing a set of aspect words in a data storage, wherein the aspect words correspond to an aspect of pain; receiving one or more aspect words from a patient that describe a pain of the patient; encoding the received aspect words into subcodes; and combining the subcodes into a pain code array.

In another embodiment, there is an automated method for decoding a description of pain from a pain code array, the method comprising retrieving a pain code array containing one or more subcodes from a storage location of the pain code array; and decoding the subcodes of the pain code array into subjective aspect words.

In another embodiment, there is a computer usable medium having computer readable program code embodied therein for representing a description of a pain in a digitized form for adjusting therapy, the computer readable code comprising instructions for storing a listing of aspect words describing a pain experienced by a patient; receiving a selection of an aspect word from the listing of aspect words; and converting the received aspect word into an integer subcode that represents the received aspect word.

In another embodiment, there is a computerized medical diagnosis method, comprising encoding a patient's subjective perception of pain into a pain code; and indexing a database of diseases with the pain code thereby diagnosing a disease.

BRIEF DESCRIPTION OF THE DRAWINGS

FIG. 2a is a diagram of a configuration of components of the system shown in FIG. 1.

FIG. 2b is a diagram of a configuration of components of the server computer shown in FIGS. 1 and 2a.

FIG. 14 is a flowchart of the Therapy Optimization process shown in FIG. 5.

FIG. 22b is a flowchart of a function utilized by the Diagnostic process shown in FIG. 4d in retrieving a diagnosis using the PQRST (pain code) array entry stored for a patient in FIG. 22a.

DETAILED DESCRIPTION OF THE PREFERRED EMBODIMENT

Figure 1:
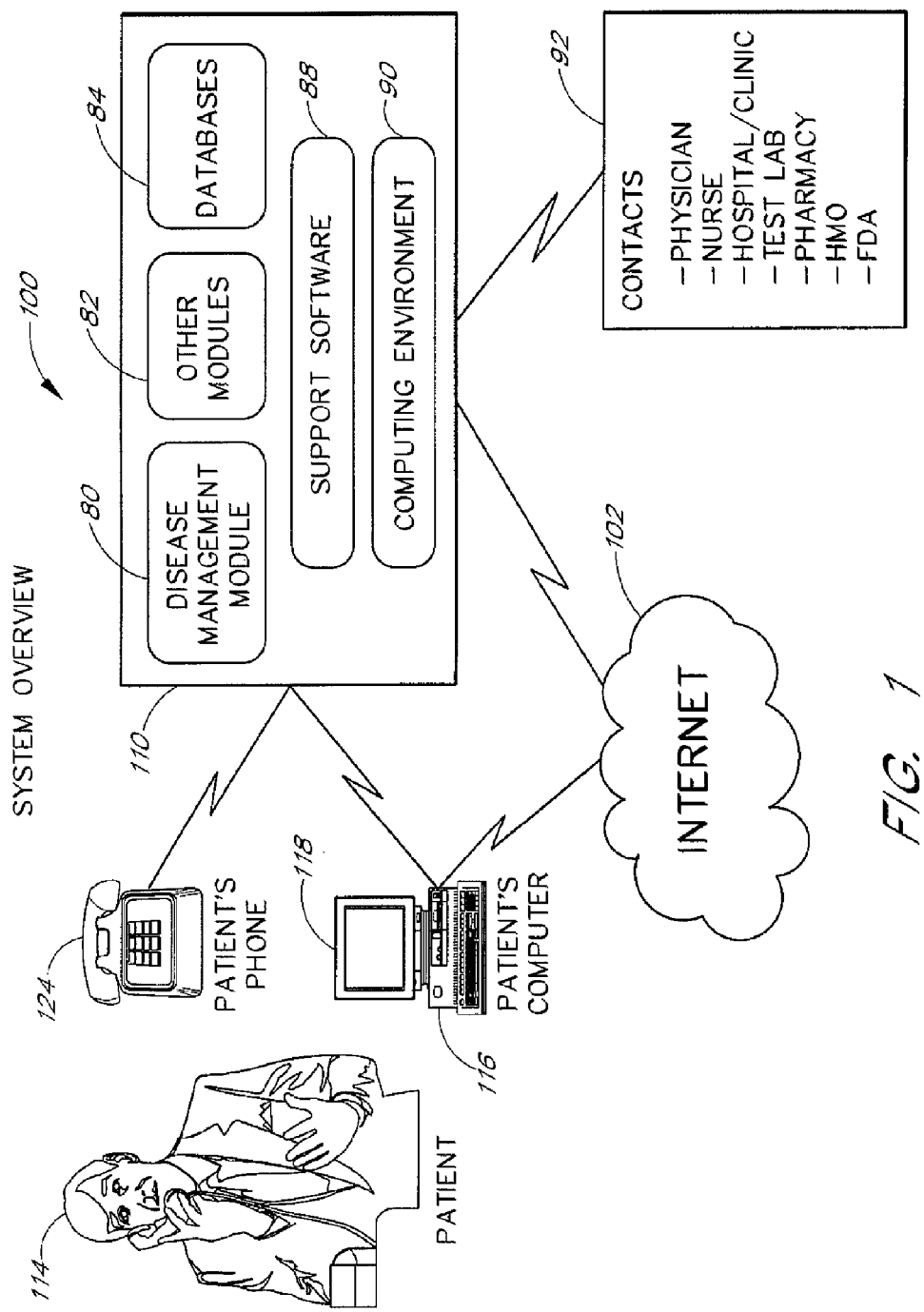
FIG. 1 is a block diagram of an automated medical diagnosis, treatment, disease management and information system of the present invention.

The following detailed description of the preferred embodiments presents a description of certain specific embodiments to assist in understanding the claims. However, the present invention can be embodied in a multitude of different ways as defined and covered by the claims. Reference is now made to the drawings wherein like numerals refer to like parts throughout.

The detailed description is organized into the following sections:

1. System Overview
2. System Processes and Databases
3. Top-level System Process Flow
4. Disease Management Overview
5. Disease Management Module
6. Open Session
7. Health Assessment
8. Significant Symptom Filter
9. Severity Assessment
10. Initial Health Assessment
11. Current Health Assessment
12. Correlation Assessment
13. Critical Curve Assessment
14. Therapy Optimization
15. Therapy Adjustment (Subjective)
16. Therapy Adjustment (Objective)
17. Patient Consent Level 18. Close Session
19. Question Versions
20. Preview Mode Feature
21. No-Response Feature
22. The PQRST Array
23. Disease Management Order (DMO)
24. Permissions Database
25. Regulatory Permissions
26. Sharing Permissions
27. Therapeutic Alteration Permission Level (TAPL)
28. Meta Structures
29. Meta Functions
30. Benefits of Disease Management System Overview Referring to FIG. 1, a computerized knowledge-based medical management system 100 will be described. A disease management module (DMM) 80 and several other high-level service modules 82 perform automated medical services for the users of the medical management system 100. The service modules 82 may include Diagnosis, Treatment Table, Automated Demand Management, Audio/Visual/Image Library, and Author Access. The DMM 80 handles tasks associated with Disease Management (DM); its major goals are to promote patient well-being, to educate patients, and to reduce costly medical intervention. The user may be a patient 114 or an assistant for a patient. Throughout this document, the words user and patient are used interchangeably. However, it will be understood that the user may be acting as a proxy for the patient. If this is the case, the user is registered as an assistant for the patient. Appropriate registration and login processes, described herein below, are utilized by the system 100 for either the patient or the assistant.

The modules 80 and 82 are supported by an Operating System and support software 88, by a number of databases 84, and by a computing environment 90 of an embedding computer hardware platform 110. The entire computer hardware-software-communications complex is operated and maintained by a support staff. All application tasks of the DMM 80 are fully automated. External contact of the DMM with patients, physicians, clinics, pharmacies, laboratories, and so on (collectively 92) are handled by automated communications systems using appropriate media and methods of the computing environment 90, such as interactive voice response (IVR), direct modem-to-modem access, or access via the Internet 102. The patient 114 utilizes a computer 116 and monitor 118, a telephone 124, or other components, some of which are described in conjunction with FIG. 2a below, to communicate with the system computer platform 110.

Referring to FIG. 2a, a block diagram of one embodiment of the medical management system 100 will be described. The system 100 includes a network "cloud" 102, which may represent a local area network (LAN), a wide area network (WAN), the Internet, or another connection service.

The system programs and databases may reside on a group of servers 108 that are preferably interconnected by a LAN 106 and a gateway 104 to the network 102. Alternatively, the system programs and databases may reside on a single server 110 that utilizes network interface hardware and software 112. The system servers 108/110 store the modules 80 and 82 (FIG. 1).

The network 102 may connect to a user computer 116, for example, by use of a modem or by use of a network interface card. The user 114 at the computer 116 may utilize a browser 120 to remotely access the system programs using a keyboard and/or pointing device and a visual display, such as the monitor 118. Alternatively, the browser 120 is not utilized when the system programs are executed in a local mode on the computer 116. A video camera 122 may be optionally connected to the computer 116 to provide visual input, such as visual symptoms or signs. Furthermore, clinical sounds could be picked up by the video camera or separate microphone (not shown).

Various other devices may be used to communicate with the system servers 108/110. If the servers are equipped with voice recognition or DTMF hardware, the user can communicate with the system program by use of the telephone 124. A telephonic embodiment is described in Applicant's application entitled "Computerized Medical Diagnostic and Treatment Advice System," U.S. application Ser. No. 08/176,041, filed Dec. 29, 1993, which has issued as U.S. Pat. No. 5,660,176, and is hereby incorporated by reference. Other connection devices for communicating with the system servers 108/110 include a portable personal computer 126 with a modem or wireless connection interface, a cable interface device 128 connected to a visual display 130, or a satellite dish 132 connected to a satellite receiver 134 and a television 136. Other ways of allowing communication between the user 114 and the system servers 108/110 are envisioned.

Figure 2B:
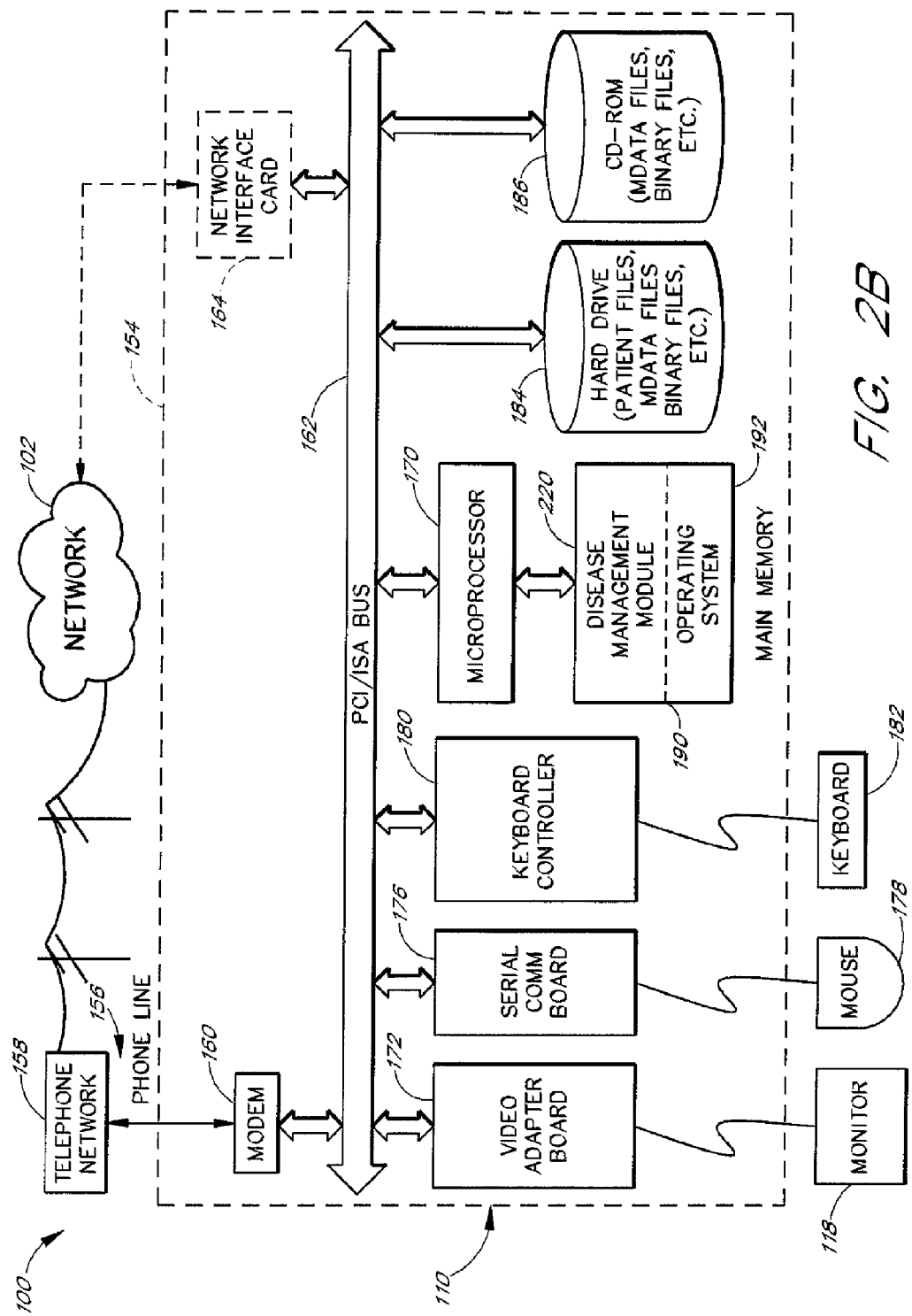

Referring to FIG. 2b, a diagram of one embodiment of a server computer 110 shows several possible interconnections to the network. To "play" a script, a special program called a Script Engine is used, which reads a medical diagnostic script file and uses its codes to perform interview actions, such as outputting a question to a patient and inputting an answer. The scripts may also collect the answers from the patient, evaluate the answers, issue a diagnosis, and update the patient's medical record. The script engine may also reside in the user computer 116 (FIG. 2a). The script engine may be stored on the hard drive or a CD-ROM, and is loaded into the main memory or a cache for execution.

The components of a presently preferred server computer 110 of the computerized medical system 100 of the present invention, are shown in FIG. 2b. The server computer 110 includes a plurality of components within an enclosure. A telephone line 156 interfaces the public telephone network 158 to the computer 110 via a modem 160. The telephone network 158 may connect to the network 102, which has connections with the system server(s) 108/110. Alternatively, the computer 110 may connect to the network 102 by use of a network interface card 164.

The hardware and system software are assembled with two basic concepts in mind: portability to other operating systems and the use of industry standard components. In this way, the system can be more flexible and will allow free market competition to continually improve the product, while, at the same time, decreasing costs. While specific hardware and software may be referenced, it will be understood that a panoply of different components could be used in the present system.

The computer 110 preferably is a personal computer with an Intel Pentium microprocessor 170. Other computers, such as an Apple Macintosh, an Amiga, a Digital Equipment Corporation VAX, or an IBM mainframe, could also be utilized. The modem 160 or the network interface card 164 connects to an industry standard architecture (ISA) or a peripheral component interconnect (PCI) bus 162. The bus 162 interconnects the microprocessor 170 with a plurality of peripherals through controller circuits (chips or boards).

The computer bus 162 has a plurality of peripherals connected to it through adapters or controllers. A video adapter board 172, preferably at SVGA or better resolution, interconnects to a video monitor 118. A serial communication circuit 176 interfaces with a pointing device, such as a mouse 178. A parallel communication circuit may be used in place of circuit 176 in another embodiment. A keyboard controller circuit 180 interfaces with a keyboard 182. A 500 Mb or greater hard disk drive 184 and an optional CD-ROM drive 186 are preferably attached to the bus 162. The hard disk 184 stores database files such as the patient files, DM files, other system files, and binary support files. The CD-ROM drive 186 also stores database files and binary support files.

A main memory 190 connects to the microprocessor 170. In one embodiment, the computer 110 may operate under the Windows 95 operating system 192. The memory 190 executes a diagnostic script engine (not shown) and a disease management module (DMM) process 220. Portions of the disease management module process software may be written in Borland Delphi Pascal, version II, and other portions may be written in Microsoft 'C', version 7.0. Furthermore, in one embodiment, the database is implemented with Microsoft Foxpro or another database program such as a SQL-compatible relational database program.

System Processes and Databases

Figure 3:
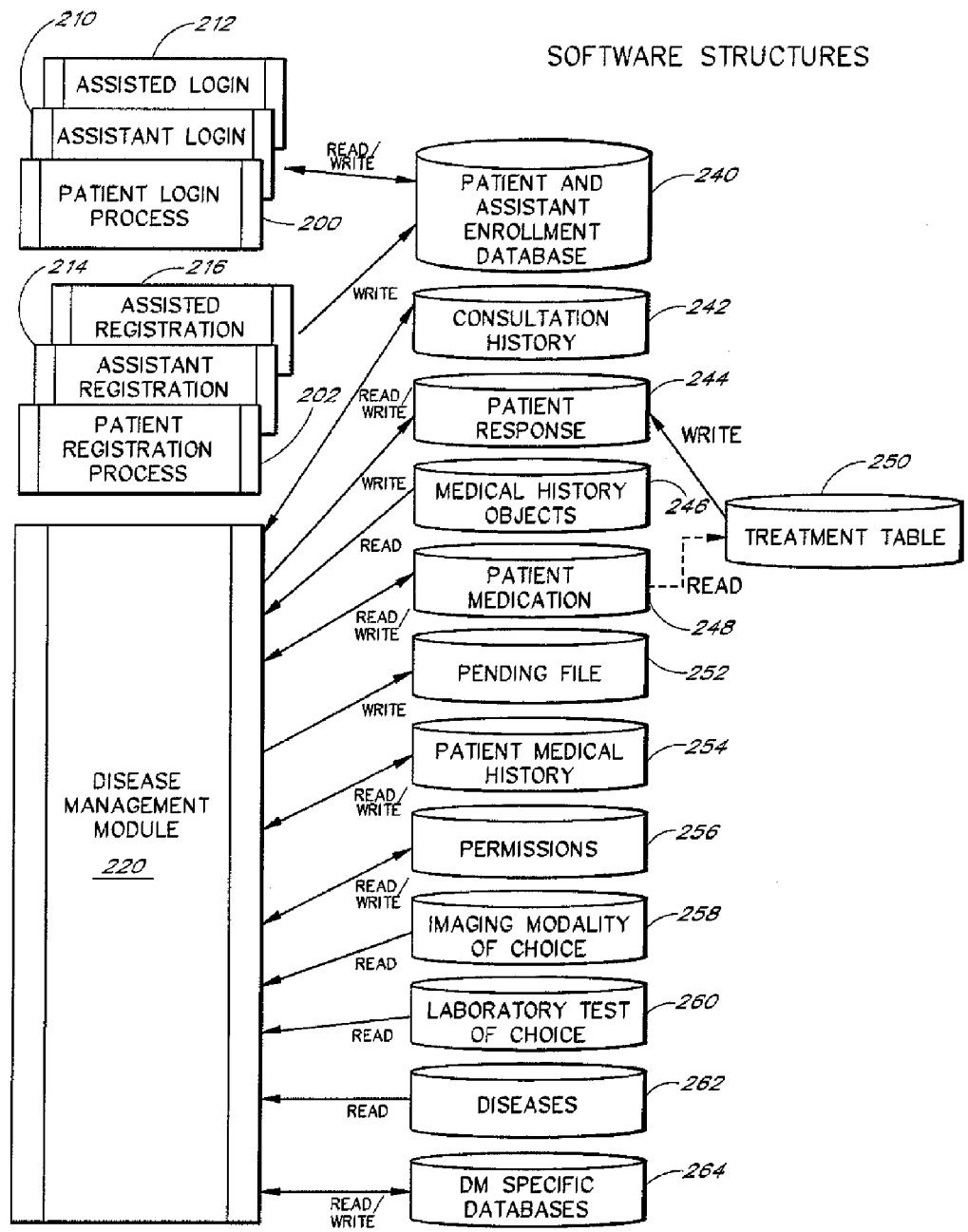
FIG. 3 is a block diagram of a portion of the processes and database files utilized by the system of FIG. 1.

Referring to FIG. 3, a portion of the processes, files, and databases utilized by the medical management system 100 will be described. Except for the DMM process, a Permissions database, an Imaging Modality database, a Laboratory Test database, a Diseases database, and other DM specific databases which are described herein below, these processes, files, and databases were described in Applicant's patent entitled "Computerized Medical Diagnostic and Treatment Advice System," U.S. Pat. No. 5,660,176.

The medical management system 100 utilizes several principal processes and related databases. A set of patient/assistant login processes 200, 210 and 212 is used by the system 100 to identify a patient who has previously registered into the system in one of three ways: 1) by prompting for a patient identification number (PIN) in process 200; 2) identify an assistant who has previously registered into the system by prompting for an assistant identification number (AIN) in process 210; or 3) identify a patient, having an assistant, who has previously registered into the system by prompting for the patient identification number in process 212. One of a set of processes 202, 214 or 216 is used to register a patient or assistant. If the user is the patient, a patient registration process is used by the system to register new or first-time patients in process 200. If the user is not the patient, an assistant registration process is used by the system to register new or first-time assistants in process 214. Then, if the patient is not already registered, an assisted patient registration process is used by the system to register the patient in process 216.

Once a user has logged in or registered, the system provides a choice of processes. The primary process of concern in the current embodiment is the DMM process 220 that manages a disease or condition of the patient. The DMM process 220 may access the laboratory test of choice database 260 or imaging modality of choice database 258 in the course of disease management and a treatment table 250 to obtain current treatment information for a particular disease or diagnosis. Associated with these processes are a patient and assistant enrollment database 240, a consultation history database 242, a patient response database 244, a medical history objects database 246, a patient medication database 248, a pending database 252, and a patient medical history database 254. These databases include an electronic medical record for each patient that is registered with the medical system 100. The electronic medical record contains all the information about each patient. A permissions database 256, a diseases database 262 and other DM specific databases 264 will be described herein below. In another embodiment, other choices are added to access other medical information processes.

Top-Level System Process Flow

Referring to FIGS. 4a, 4b, 4c and 4d, the top level flow 300 of the medical management system software will be described. A telephone number used to access the system 100 via the telephone may vary in various embodiments of the system. If the sponsoring agency or hospital wishes to provide access to the medical management system 100 at no cost to the caller, then a toll-free (e.g., 800, 888 or other number) service number can be used. If the sponsoring agency or hospital wishes to recover the costs of running the system 100 from the caller, it may use a pay-per-call or premium charge number (e.g., 900 service). "Current Procedural Terminology" (CPT-4) codes are available to describe and bill third party payers for telephone consultations. They are a listing of the descriptive terms and identifying codes for reporting medical services and procedures. CPT-4 codes are the most widely accepted nomenclature for reporting physician services to insurance companies. If access is provided to the system 100 via the Internet or other network, an appropriate web address (or addresses) is provided to the user.

Beginning at a start state 302, the user 114 (FIG. 1) desiring medical advice dials the telephone number for the system 100 on the telephone 124 (FIG. 2a). The user may be the patient or may be an "assistant", e.g., parent, relative, or friend, that is helping the patient. Alternatively, the user may access the system 100 though the user computer 116, such as through the Internet as previously described. Moving to state 304, the system 100 answers the call automatically and greets the caller 114 with an introductory greeting message by playing back a speech file stored on the system hard drive by use of a voice processing board, such as a D/41D available from Dialogic. Alternatively, if the user is using the browser 120 (FIG. 2a) or other user interface on the Internet 102, a greeting message is displayed to the user on the visual display 118. Thus the system 100 communicates with the user 114 either by the telephone or by messages displayed on the visual display. Subsequent steps in the process or function flowcharts will only describe one form of user communication for brevity purposes.

Proceeding at state 306, the system 100 asks each patient who calls the system a series of "initial screening questions." These questions are designed to identify patients who are critically ill; they are not designed to identify the patient's problem. The initial screening questions enable the system to filter out patients who require immediate medical attention.

Moving to decision state 308, any patient found to be critically ill is instructed to dial the emergency response telephone number "911" at state 309 or will be automatically connected to the nearest emergency medical services system in the patient's area. The session is terminated by process 300 at state 310. The following are examples of initial screening questions:

? IS THIS A MEDICAL EMERGENCY?
? ARE YOU HAVING DIFFICULTY BREATHING?
? ARE YOU EXPERIENCING SEVERE PAIN OR PRESSURE IN YOUR CHEST?

If the system determines that the patient is experiencing a medical emergency, it may provide the patient with a menu of emergency medical procedures at state 311. In situations where the patient or the caller for the patient is far from the nearest emergency help, e.g., a rural setting, the user may need to initiate emergency procedures immediately. The menu of emergency medical procedures provides several choices to the user. If the user presses touch tone key "1" or speaks the word "one" into the telephone mouthpiece, process 300 branches to state 312 wherein well known CPR (cardiopulmonary resuscitation) information is recited. If the user has a speakerphone capability associated with the telephone 124 being used, the user may be able to listen to and perform the instructions given by the system 100 in a hands-free manner away from the telephone. If the caller presses touch tone key "2" or speaks the word "two" into the telephone mouthpiece, process 300 branches to state 313 wherein well known Heimlich Hug information for choking is recited. At the completion of either state 312 or state 313, the session ends at state 314.

If the patient is determined at state 308 not to have a medical emergency, i.e., the system 100 is satisfied that no immediately life threatening condition is present, process 300 moves to a decision state 315 to determine if the user is the actual patient. If so, process 300 proceeds to a decision state 316 to determine if the patient has previously registered or ever consulted with the system 100, i.e., is not a new or first-time caller. If so, the system 100 verifies the patient's identification and retrieves their medical record at the patient login process 200. At the completion of process 200, process 300 proceeds through off-page connector C 317 to state 344 (FIG. 4d). If the patient is not registered, as determined at decision state 316, the system 100 proceeds to the patient registration process 202 for a new patient. At the completion of process 202, process 300 proceeds through off-page connector C 317 to state 344 on FIG. 4d.

Figure 4A:
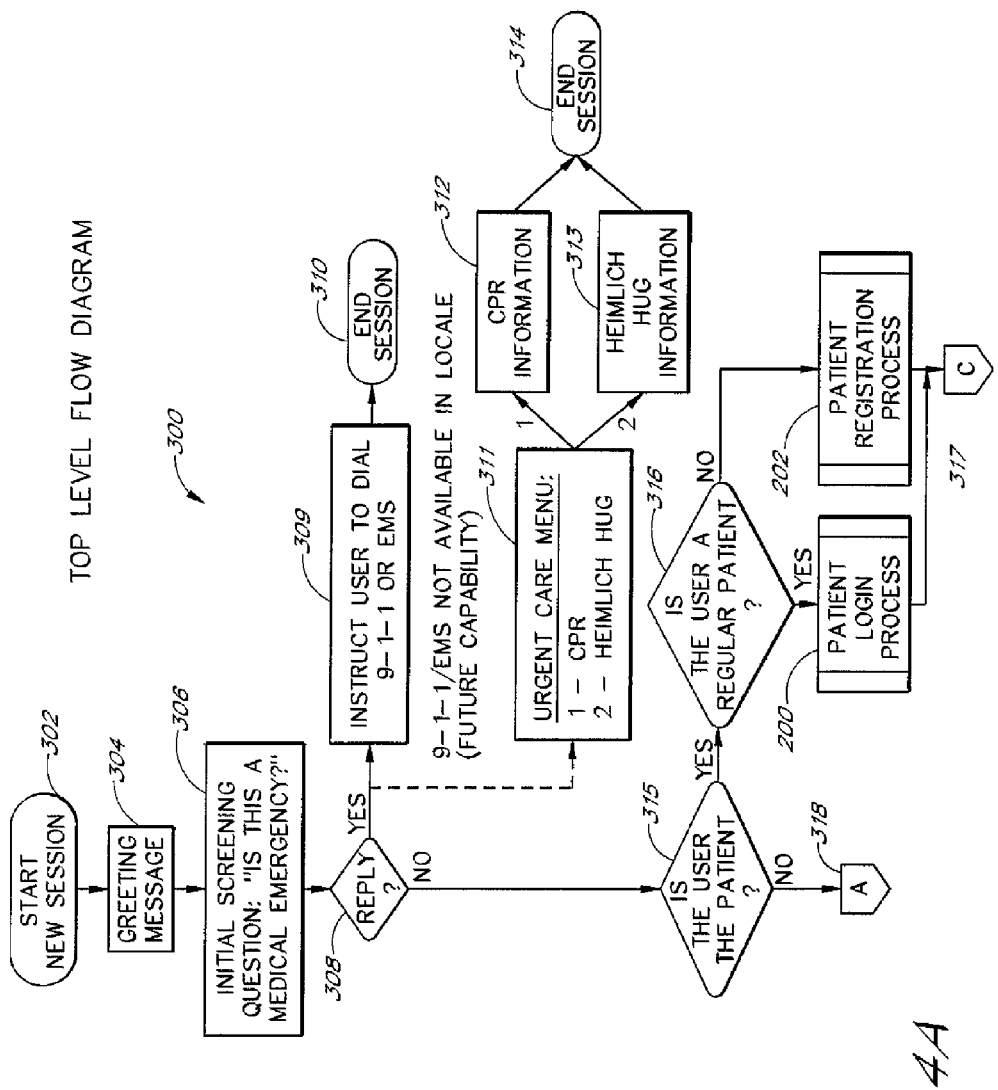
FIGS. 4a, 4b, 4c and 4d are a flowchart of the top-level process performed by the system of FIG. 1.
Figure 4B:
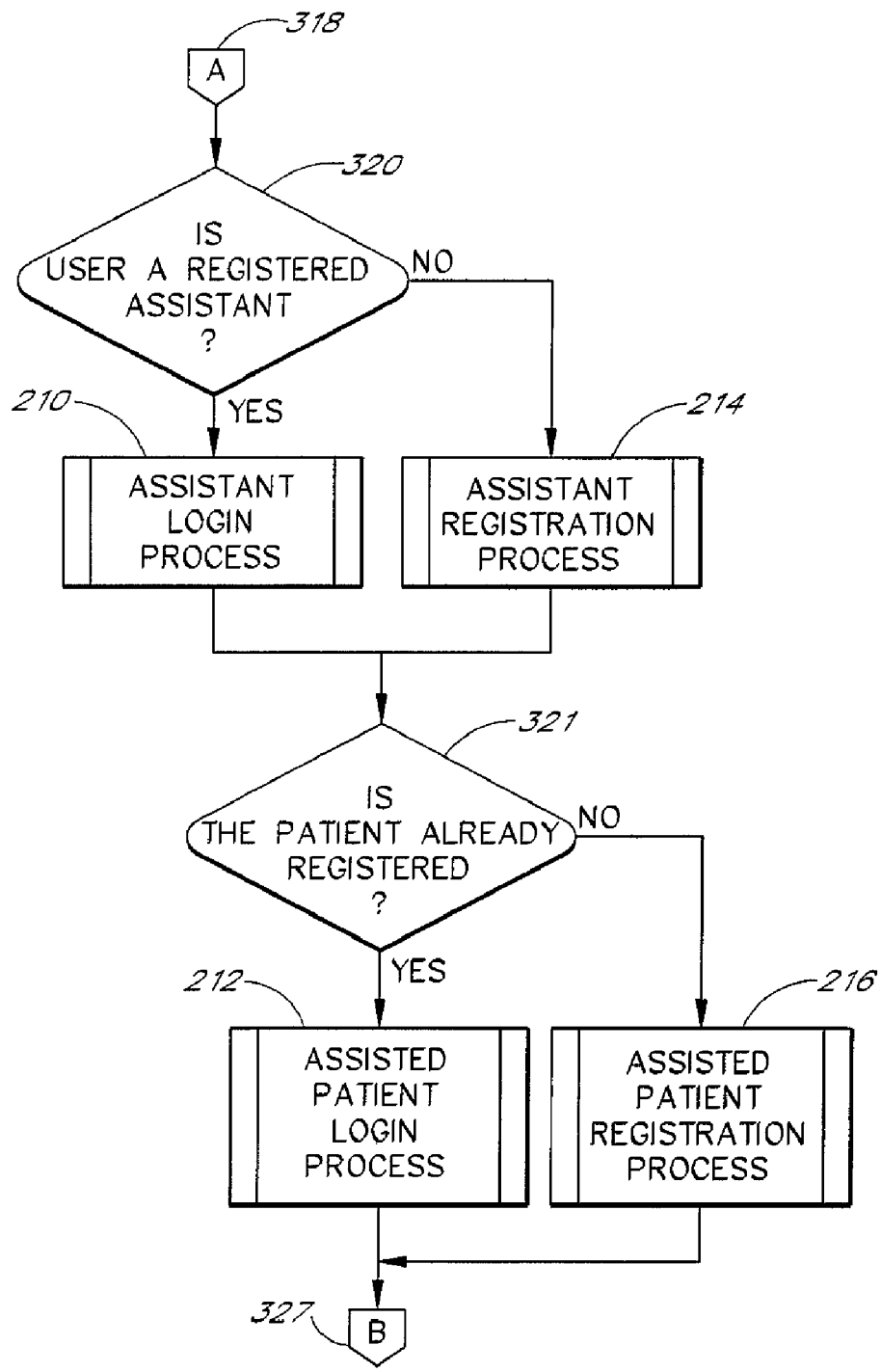
Figure 4C:
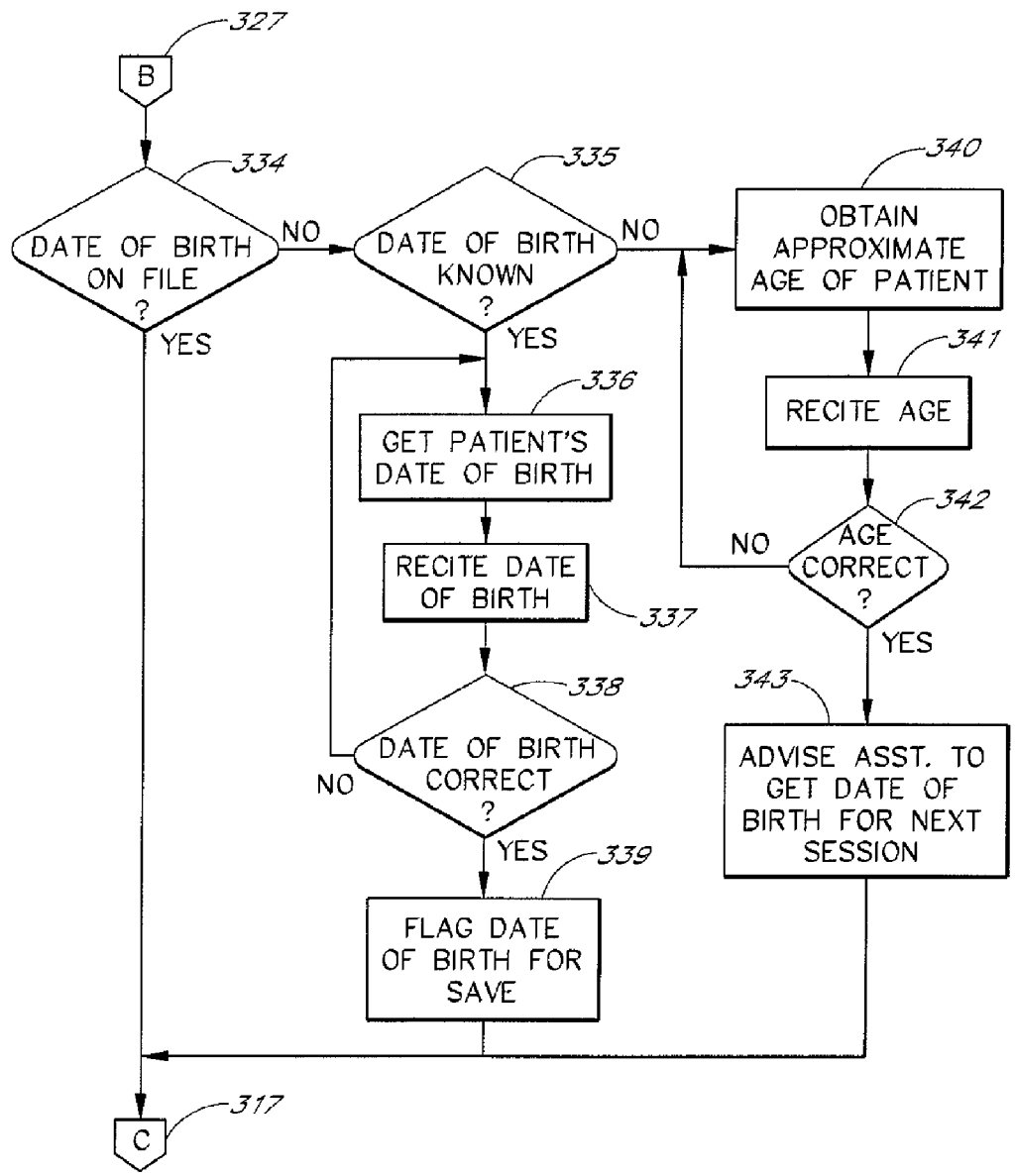
Figure 4D:
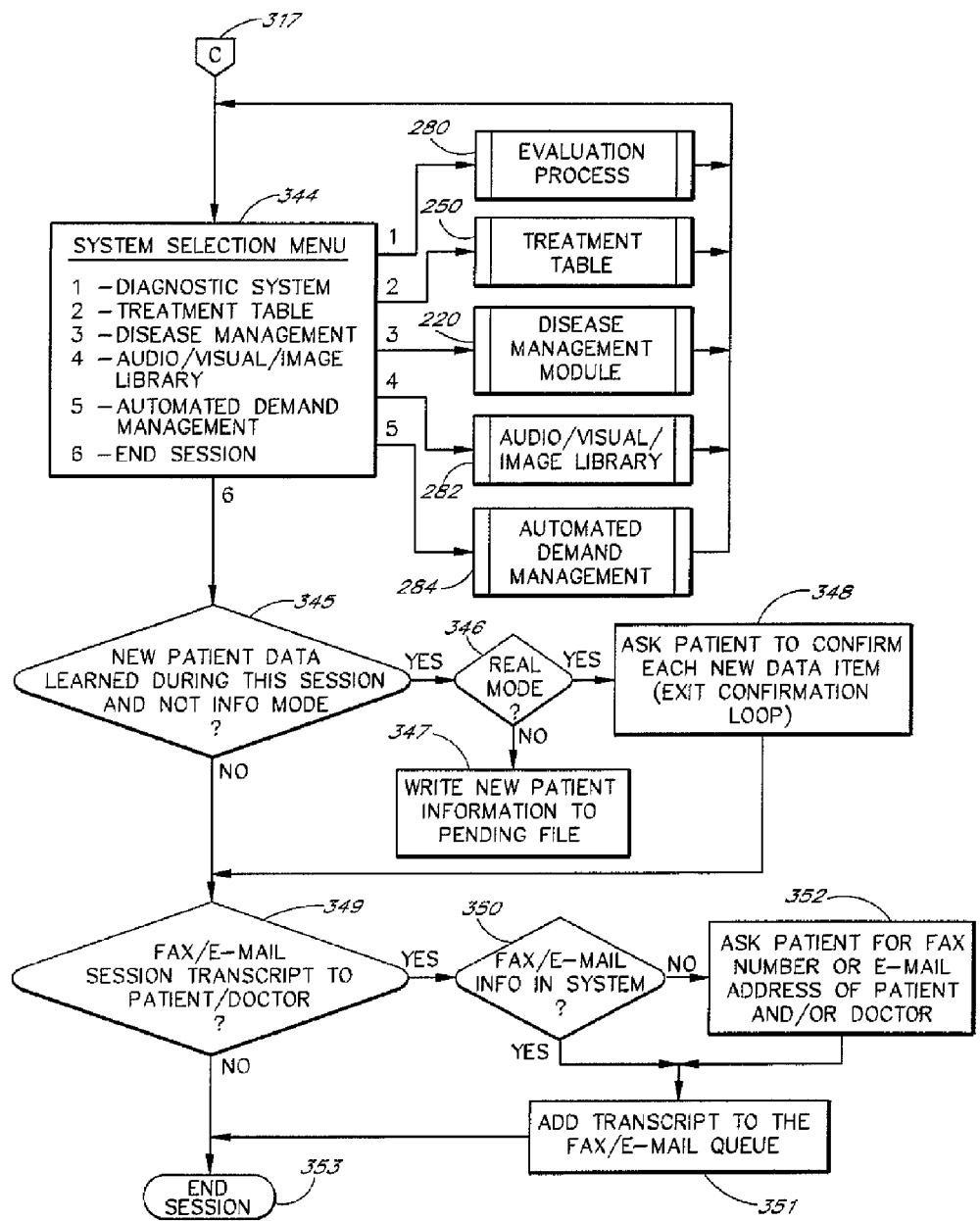

If the user is not the patient, as determined at state 315, process 300 proceeds through off-page connector A 318 to a decision state 320 on FIG. 4b. There will be times when the patient may not be able to use the system 100 directly, e.g., due to injury, weakness or altered level of consciousness. In these cases, an "assistant" may interact with the system on behalf of the patient.

An assistant registers with the system through the assistant registration process 214. The assistant registration record is identical to the patient registration record in structure, but three fields have special significance for an assistant: ASST_PERM, ASST_EXP, and RELATIONS. The ASST_PERM field is a Boolean flag that can only be set true off-line by the system administrator who has verified, through separate means, that a relationship exists between a patient and an assistant. The relationships are one-to-many, i.e., a patient may have one or more assistants, and an assistant may be related to more than one patient. The ASST_PERM flag may also be constrained by the ASST_EXP field, which contains a timestamp for the expiration of the ASST_PERM attribute. If the ASST_PERM flag is true, then the RELATIONS pointers will point to one or more patient records for whom this assistant is a "permanent assistant;" otherwise the RELATIONS field will be empty.

The medical information gathered during an assisted consultation is written to the patient's medical record if the following three conditions are met:

(a) the assistant's ASST_PERM flag is True
(b) the ASST_EXP timestamp has not been reached
(c) the assistant has a relationship pointer to the patient record If any of these conditions are not met, then any new medical information gathered on this patient will be saved to the Pending file 252 (FIG. 3) for off-line verification by the system administrator.

The system 100 establishes at state 315 whether the user is the patient, or an assistant. If the user is not the patient, then the system asserts that the user is an assistant and, at decision state 320, determines if the assistant is registered. If the assistant is not already registered with the system, the system enrolls the new assistant at the assistant registration process 214. If the assistant is already registered with the system 100, process 300 performs the assistant login process 210. At the completion of either process 214 or process 210, process 300 advances to a decision state 321.

If the patient is not already registered with the system 100, as determined at decision state 321, then the system allows the assistant to register a new patient at the assisted patient registration process 216. However, if the patient is already registered with the system 100, as determined at state 321, process 300 performs the assisted patient login process 212. At the completion of process 216 or process 212, process 300 proceeds through off-page connector B 327 to a decision state 334 on FIG. 4c.

At decision state 334, process 300 determines if the patient's date of birth is in the patient's medical record. If so, process 300 proceeds through off-page connector C 317 to state 344 on FIG. 4d. If not, the system 100 attempts to get the patient's date of birth. Moving to state 335, the system 100 asks the assistant if the patient's date of birth is known. If so, process 300 advances to state 336 to request the patient's date of birth. At state 337, the system 100 recites the patient's date of birth obtained at state 336. At a decision state 338, the assistant determines if the date of birth is correct as recited by the system 100. If not, process 300 loops back to state 336 to request the patient's date of birth again. If the patient's date of birth is correct, as determined at state 338, process 300 flags the date of birth for saving in the patient's medical record at state 339, and proceeds to state 344 on FIG. 4d.

If the patient's date of birth is not known, as determined at state 335, process 300 proceeds to state 340 wherein the system requests the assistant to provide an approximate age of the patient. The age is an important parameter used by the DMM process 220, the diagnostic module and the treatment table 250. At state 341, the system 100 recites the patient's approximate age obtained at state 340. At a decision state 342, the assistant determines if the age is correct as recited by the system 100. If not, process 300 loops back to state 340 to request the patient's approximate age again. If the patient's approximate age is correct, as determined at state 342, the system 100 advises the assistant at state 343 to get the patient's actual date of birth before the next consultation, and proceeds to state 344 on FIG. 4d. The system 100 uses the approximate age in the session during the diagnostic module and the treatment table 250.

At state 344 on FIG. 4d, the system 100 presents the user with a system selection menu. Here, the caller is asked to select from among six choices: diagnostic system, treatment table, disease management, audio/visual/image library, automated demand management, or end session as described below:

A. Diagnostic System: The system starts an evaluation process 280 at a menu, where it asks the patient to begin identification of the complaint.

B. Treatment Table: The system takes the patient to the treatment table process 250 at a menu, where it asks the patient to select a treatment selection method.

C. Disease Management: The system starts the DMM process 220 where it first determines if the patient has previously used the Disease Management Module. This process is described in detail below.

D. Audio/Visual/Image Library: The system starts a Audio/Visual/Image Library process 282 which lets a patient hear medical sounds, see medical videos, or see medical photographs or other images.

E. Automated Demand Management: The system starts an Automated Demand Management process 284 to help the patient determine if a physician should be seen, and if so, who should be seen and when they should be visited.

F. End Session: The system performs several steps and then terminates the session.

At the exit point of the evaluation process 280, the system 100 gives the patient the option of selecting another complaint. At the end of the treatment table process 250, the system gives the patient the option of selecting another treatment. At the end of the audio/visual/image library process 282, the system 100 gives the patient the option of selecting another audio clip, video, or image. At the end of the automated demand process 284, the system 100 gives the patient the option of receiving advice for another problem.

At the completion of the evaluation process 280, the treatment table process 250, the disease management module process 220, the audio/visual/image library process 282, or the automated demand management process 284, the system 100 loops back to state 344 and again provides the system selection menu for the user. If the user chooses the End Session selection at state 344, the system 100 moves to a decision state 345. At decision state 345, the system 100 determines if process 280, process 250, process 220, or process 284 did not occur in Information mode, i.e., did occur in either Real mode or Pending Mode, and examines a symbol table associated for the current patient to determine if any of the configured memory variables are past medical history conditions that need to be saved to the patient's medical history file. If both conditions are true at state 345, the system 100 advances to a decision state 346 to determine if the consultation is being performed in Real mode. If not, the consultation is being performed in Pending mode, and the system 100 then writes any new patient information obtained during the consultation to the Pending file 252 at state 347.

If decision state 346 proves to be true, i.e., Real mode, for each past medical condition that needs to be saved, the system 100 asks the patient at state 348 to grant permission to save the datum to the patient's medical history file and to confirm that the datum is correct. For example, during a consultation for cough, the system 100 may have learned that the patient has been diagnosed as being HIV positive. The system 100 will ask, "May I record the information about your HIV diagnosis in your medical record?" If the patient responds "yes", then the system 100 will ask, "Please verify that your diagnosis for HIV was positive, is this correct?" If the patient responds "yes", then the system 100 writes the diagnosis, and a score indicative of system accuracy to the patient's medical history file. After confirmation, each data item is stored in the patient's file in the patient medical history database 254 (FIG. 3).

At the completion of either updating the patient medical history database 254 at state 348, or state 345 proves to be false, or at the completion of state 347, the process 300 moves to a decision state 349. Before the system 100 ends the consultation with the patient, it presents a summary of all the advice it has given. In a telephonic session, the patient is asked to write down and repeat back the key points. The system 100 then gives the patient the option of receiving a summary of the consultation session and specific recommendations provided by the system via facsimile, electronic mail (E-mail) or a mail service, such as first-class mail. If a fax or E-mail is desired, process 300 moves to a decision state 350 to determine if information to send the summary and recommendations is available in the system. If not, process 300 asks the patient for the information, e.g., a fax number, E-mail address or mail address, at state 352. The patient also has the option to send a summary of the consultation to his or her health care provider or specialist. Proceeding to state 351, process 300 adds the transcript of the current telephone session to a fax queue or an E-mail queue, as desired, for subsequent transmission. At the completion of state 351 or if process 300 determined at state 349 that the session transcript was not to be sent, the session is terminated at state 353.

Disease Management Overview

The present invention includes a computer program called a Disease Management Module (DMM). The disease management module is one of several high-level service modules that perform automated medical services for the users of the medical management system 100. In this context, disease management (DM) means the continuing medical care of a patient who has been diagnosed with a specified health problem called a disease. The DDM may continue care throughout a patient's lifetime. The DMM performs disease management in a fully automated manner, using periodic interactive dialogs with the patient to obtain health state measurements from the patient, to evaluate and assess the progress of the patient's disease, to review and adjust therapy to optimal levels, and to give the patient medical advice for administering treatment and handling symptom flare-ups and acute episodes of the disease. The goal of the disease management module is to promote patient health in an automated manner that reduces costly medical intervention.

Various features of the DMM software are specifically designed to accumulate and use patient-specific information, so that disease management can be tailored more to each individual case. As the module manages a given patient over time, it builds a profile of the case, in the form of the frequency and reasons for the patient's contacts with the DMM, the patient's subjective understanding of the disease, the patient's objective response to various medical treatments, and the patient's preferences in treatment. The module then uses that knowledge to adjust its internal procedures, so that they adapt more to the specific patient.

When a patient is first admitted to DM, the DMM runs a registration procedure that verifies the patient's medical history, initializes the initial therapy for the patient's disease, and sets up a schedule for patient contacts. For every registered DM patient, the DMM conducts periodic automated sessions with the patient. During each session, the DMM obtains and updates the patient's medical history with the latest health measurements, analyzes and assesses patient health as needed, adjusts therapy as needed, and gives the patient appropriate medical advice. At the end of each session, the DMM schedules the next session. Ultimately, the DMM discharges patients by moving them from the disease management state to another state such as to the medical care of a human physician, to the care of the diagnostic module of the medical system, or to a normal health state with the appropriate follow-up health checkups.

The DMM module is now summarized here in terms of its overall features, so as to put the features into the overall context. Each feature will be further described herein below.

In all of its contacts with patients, the DMM must insure that it complies with a large number of permissions, consents, and authorizations granted by various agents and agencies. The DMM uses the Permissions database to manage these control data.

To conduct online interactive dialogs with patients (or their agents), the DMM uses scripts. Scripts are special computer programs capable of outputting text and questions to a patient, waiting for a response from the patient, recording the response, and taking further action based on the response. The development and use of scripts has been described in U.S. application Ser. No. 08/893,402, filed Jul. 11, 1997, issued as U.S. Pat. No. 5,935,060, entitled "Computerized Medical Diagnostic and Treatment Advice System including List Based Processing", and in U.S. application Ser. No. 08/893,912, filed Jul. 11, 1997, issued as U.S. Pat. No. 6,022,315, entitled "Computerized Medical Diagnostic and Treatment Advice System including Network Access", both of which are hereby incorporated by reference.

A normal online dialog with a patient takes the general form of a sequence of questions asked by a script, and answers provided by the patient. As the script runs, it considers the patient's current status, selects a question, and presents the question to the patient. The patient responds, the script analyzes the response, selects another question, and so on until the session is normally terminated.

A script Preview Mode for the DMM allows the patient to answer a question in a "look ahead" mode, to see what the consequences of a given response would be, without formally selecting the response. Abnormal script terminations can be handled by the DMM in an intelligent, proactive manner using a No-Response function. If a patient suddenly fails to respond in the middle of a dialog, this function can use all that is known about the patient, the patient's location, and the disease being managed to respond proactively, including—if necessary—the ability to contact the patient's nearest emergency assistance facility or to call 911 for the patient.

The DMM performs all of its contact with patients in the form of Disease Management sessions, which are regularly scheduled, online dialogs with the patient. A DM session can be initiated by either the patient calling the medical system (inbound), or by the system calling the patient (outbound). Every DM session consists of four major tasks performed in the following sequence: Open Session, Health Assessment, Therapy Optimization, and Close Session.

The Open Session task initializes data and registers patients. The task uses the patient's health history and the disease being managed to establish the assessment health parameters that are to be measured and tracked, including relevant thresholds, limits, ranges, and critical values. It also gives patients instructions on how to observe symptoms, perform health measurements, assess their health, and prospectively trend their disease.

The Health Assessment task obtains health measurements from the patient for the interval since the last session, encodes symptom descriptions using a PQRST Array, and calculates various relevant health counts, patterns, and trends. It analyzes health state using a Correlation Assessment function and a Critical Curve Assessment function. The Correlation Assessment function uses a Subjective-Objective Correlation Factor (SOCF), a statistical measure of how well a given patient can assess his/her own disease state and progress, to assess the patient's health based on subjective data. The PQRST Array is an encoding scheme used to convert subjective descriptions of pain symptoms into a DMM-wide digitized pain code. The Critical Curve is a time-plot of specified health parameters that the DMM can compare to standard critical curves to detect or predict rapid deterioration of patient health.

Finally, the Health Assessment task decides what action to take for the patient, such as referring the patient out of the system, to seek human medical attention; or referring the patient to the diagnostic module process for diagnosis of a new symptom; or proceeding to the next task to determine the next therapy step for the patient.

The third task of the DM session is Therapy Optimization, whose express goal is to adjust therapy step by step in a manner that balances the risks and benefits, maximizes efficacy and minimizes adverse side effects, and converges to an optimum therapy for this patient over the long term. The task selects one of several possible therapies from a treatment table, adjusts dosages in small steps as controlled by a Patient Consent Level function, presents the risks and benefits to the patient, and lets the patient accept or reject the recommendation. If the patient rejects, the task computes the next best therapy, and the next, until it reaches a limit that is stored in the Permissions database. In all of its work, the task consults a Therapeutic Alteration Permission Level (TAPL) to determine how much authority it has to modify therapy automatically. If the task has too little authority to recommend a therapy, or if the patient rejects all therapy suggestions, the task refers the patient to a human physician.

The final task of the DM session, Close Session, stores all of the assessment measurements, parameters, and decision factors in the patient's medical history database. The task also processes the therapy changes that the patient accepted, issues relevant instructions to the patient, and finally reschedules the patient for the next session. Then the task initiates processes to output various session logs and reports requested during the session, and finally, the DMM saves the relevant data and terminates the current DM session. The DMM is now done with this patient until the next session repeats the process.

Disease Management Module

Figure 5:
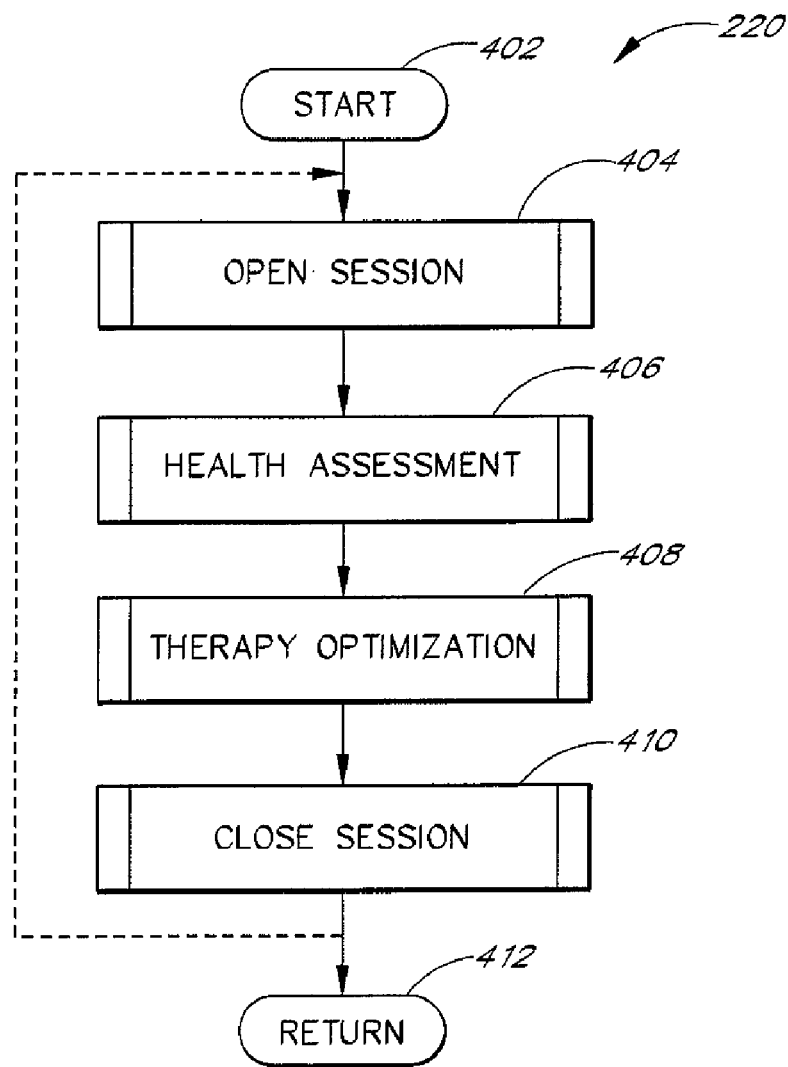
FIG. 5 is a flowchart of the Disease Management Module process shown in FIG. 4d and performed by the system of FIG. 1.

Referring to FIG. 5, the process 220 will be described. Process 220 comprises the executable portion of the Disease Management Module (DMM), which conducts an on-line, interactive dialog with a patient for the purpose of managing a known disease of the patient. Process 220 consists of four processes 404, 406, 408, and 410. A DM session starts when control is passed to program 220 at the start node 402. From the start node 402, process 220 invokes process 404, which performs initialization, file opening, and registration functions as described in conjunction with FIG. 6 below. When process 404 returns control to process 220, process 220 next invokes process 406, which inputs health measurements from the patient, analyzes them, and assesses the patient's current health state. When process 406 returns control to process 220, process 220 next invokes process 408, which computes an optimum next therapy step that is accepted by the patient. When process 408 returns control to process 220, process 220 next invokes process 410, which outputs various reports, saves session data, and closes working files. When process 410 returns control to process 220, process 220 passes control to step 412. Step 412 returns control to the process that invoked process 220 at node 402.

Open Session

Figure 6:
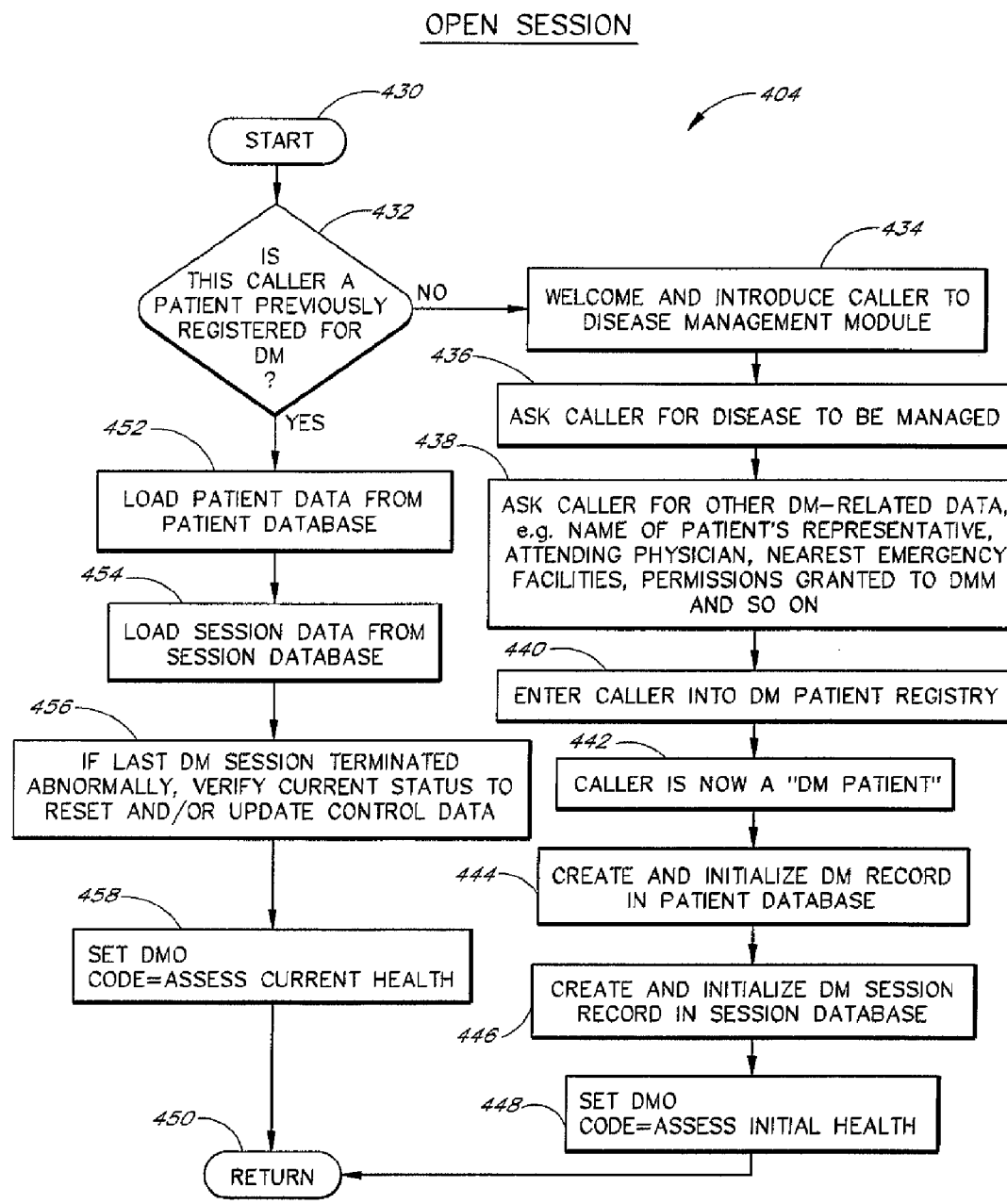
FIG. 6 is a flowchart of the Open Session process shown in FIG. 5.

Referring to FIG. 6, the process 404 will be described. Process 404 establishes the data needed to conduct a DM session. It registers patients that are new to the DMM and loads existing data for patients that have previously conducted DM sessions. Finally, process 404 creates a Disease Management Order(DMO) record, in which the cumulative decisions made by the DMM during this DM session are stored. The DMO is further described in section Disease Management Order. Process 404 receives control at the start node 430. Next, process 220 passes control to decision 432, which looks up the patient's identification in the DM register to see whether the patient is a registered, i.e. has conducted previous DM sessions. If the patient is not registered, process 404 passes control to step 434, otherwise to step 452, which will be described later in this section.

Step 434 is the first of seven successive steps 434, 436, 438, 440, 442, 444, 446 that register a patient for Disease Management. Step 434 outputs messages to greet and inform the patient that s/he is about to begin registration for DM. Next, step 436 inputs the name of the disease to be managed. Next, step 438 interviews the patient to input data required to conduct Disease Management, including the name of a representative that can speak for the patient, the name and location of the patient's physician, names and telephones emergency facilities near the patient, and so on. Next, step 440 creates a record for the new patient in the DM registry. Next, step 442 establishes the patient as a registered DM patient. Next, step 444 creates a new data record for use by the DMM in the patient's database. Next, step 446 creates a new data record for session data in the session database. Step 446 completes the registration of the patient as a new DM patient. After step 446, control goes to step 448, which creates a new creates a Disease Management Order (DMO) record, in which the cumulative decisions made by the DMM during this DM session are stored. Step 448 initializes the DMO to indicate that this patient is a newly registered DM patient and needs an initial health assessment. After step 448, process 404 passes control to step 450, which returns control to the process that called process 404.

Continuing now to describe process 404 at step 452. Step 452 retrieves the patient's medical record from the patient database. After step 452, control passes to step 454, which loads the last DM session data for this patient from the session database. After step 454, control passes to step 456, which confirms that the last session terminated normally and sets appropriate control data if it did not. After step 456, control passes to step 458, which initializes the DMO to indicate that this patient needs a current health assessment in subsequent processing. After step 458, control passes to step 450, which returns control to the process that called process 404.

Health Assessment

Figure 7:
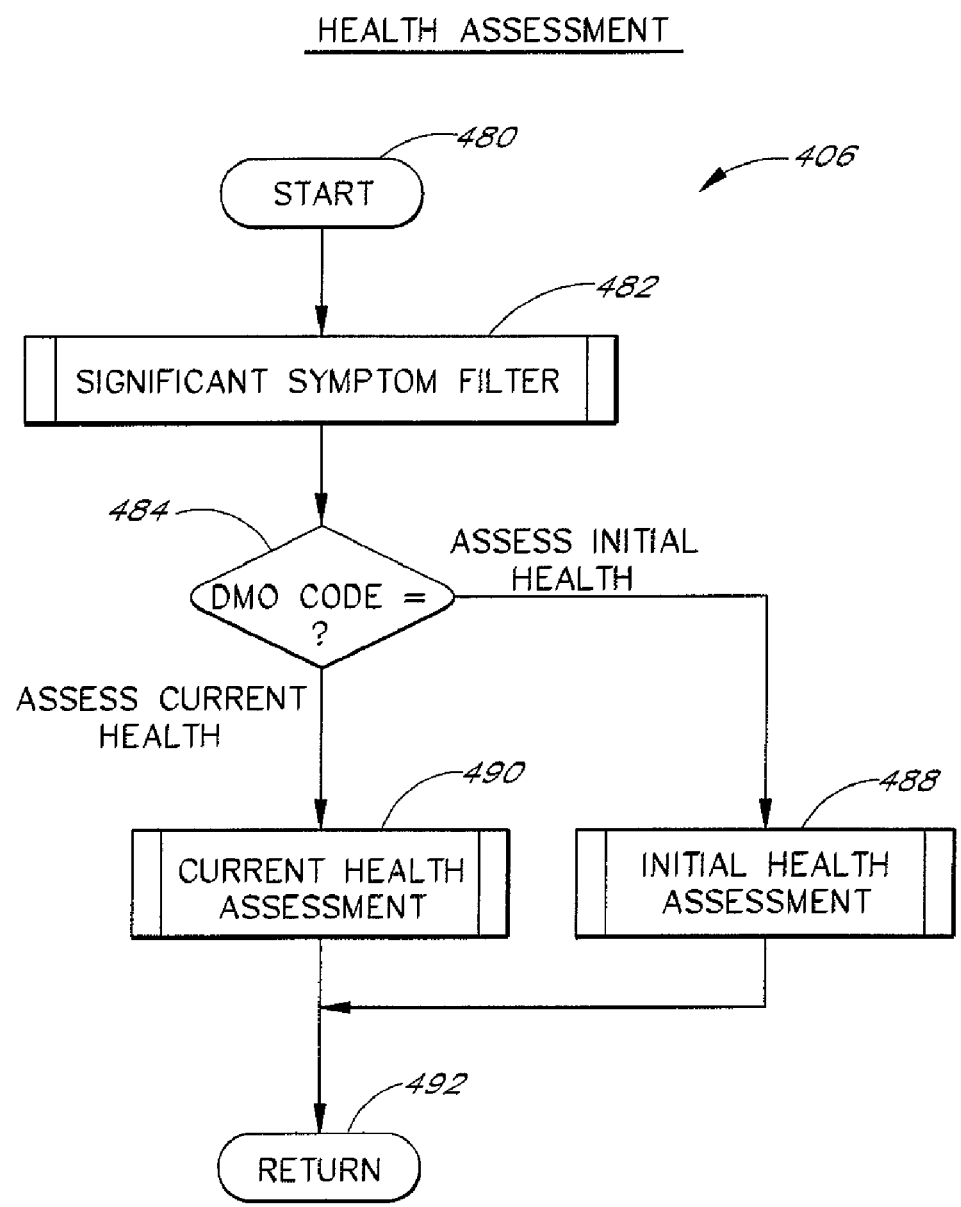
FIG. 7 is a flowchart of the Health Assessment process shown in FIG. 5.

Referring to FIG. 7, the process 406 will be described. Process 406 performs the health assessment for the DM session. It is basically a staging process that invokes other processes that perform health assessment of the patient. Process 406 receives control at start node 480. After node 480, process 406 invokes process 482, which is named the Significant Symptom Filter and will be described below in conjunction with FIG. 8. When process 482 returns control, process 406 passes control to the test 484, which tests the DMO record code to determine whether this patient is a new DM registrant or a returning DM patient. For new patients, process 406 invokes node 488, which assesses the health of newly registered patients and will be described below in conjunction with FIG. 10. For current patients, process 406 invokes node 490, which performs the health assessment for returning DM patients and will be described below in conjunction with FIG. 11. After health assessment for new or returning patients is completed, process 406 returns control at node 492.

Significant Symptom Filter

Figure 8:
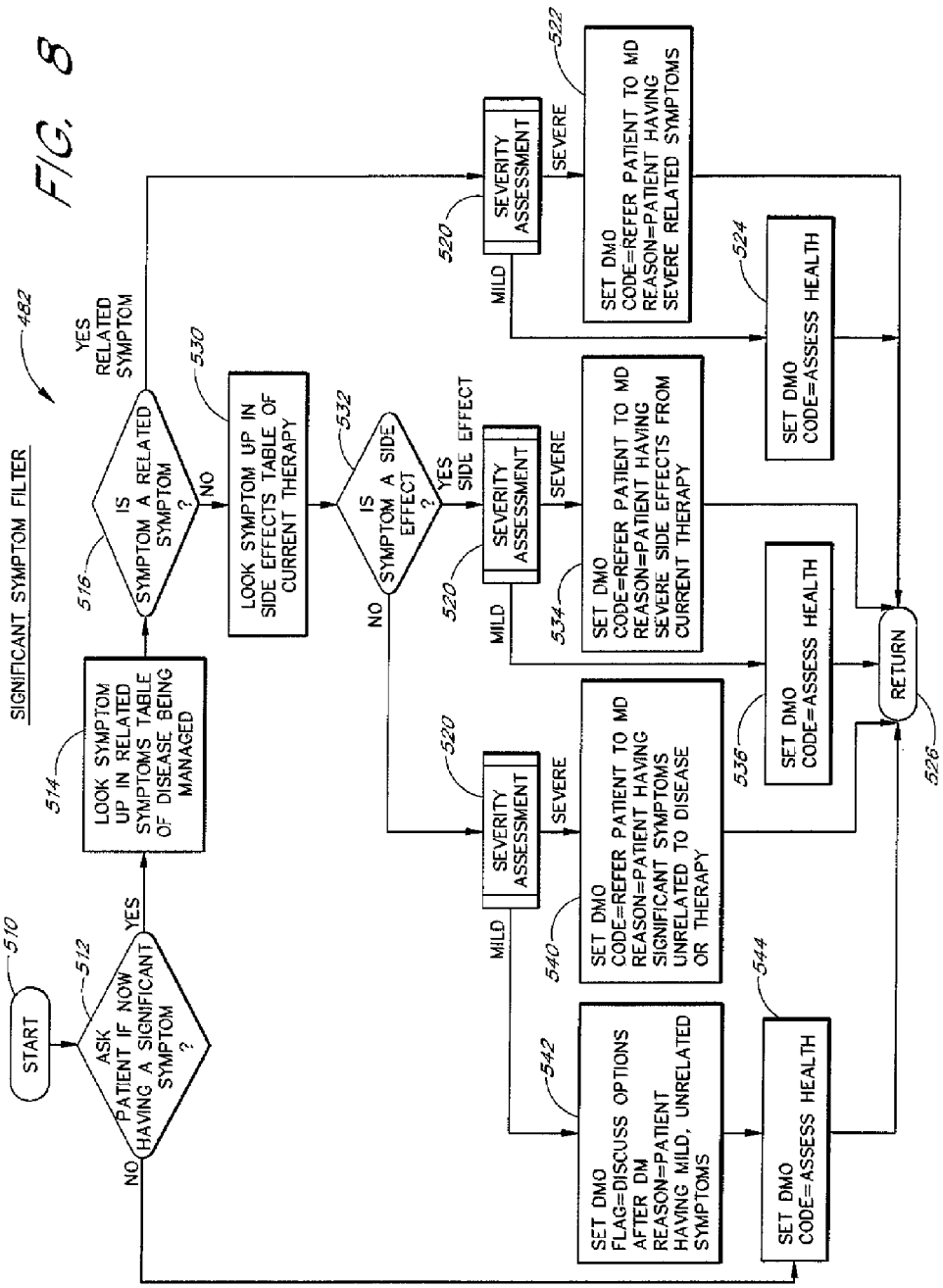
FIG. 8 is a flowchart of the Significant Symptom Filter process shown in FIG. 7.

Referring to FIG. 8, the process 482 will be described. Process 482 applies several tests to the patients current symptoms to classify the patient's current health state, decide on specific assessment needs and their reasons, and forward this assessment to subsequent DM processes. These needs are saved in the patient's DMO, which is then processed by subsequent DMM routines. The DMO record is described later in section Disease Management Order.

Process 482 receives control at start node 510. From there, it passes control to test node 512, which represents the first filter by asking the patient whether s/he is having any significant symptoms at present. If the patient is not having significant symptoms, s/he can be assessed by automated means, and therefore process 482 passes control to step 544. Step 544 which sets the DMO record code to indicate that this patient's health needs to be further assessed by subsequent routines. The control returns via node 526.

If, at node 512, the patient is currently having significant symptoms, then process 482 needs to determine whether or not the patient has a symptom related to the disease being managed. To do this, process 482 passes control first to step 514, which inputs the symptom from the patient and looks it up in a table of related symptoms, and next to test 516, which branches to node 520 if the symptom is related to the disease being managed, and branches to node 530 otherwise. This completes the second filter, which has now identified patients with and without significant related symptoms.

If, at node 516, the patient does have a related symptom, process 482 invokes the Severity Assessment function 520 to further classify the related symptom as mild or severe. For patients with severe related symptoms, process 482 passes control to step 522, which sets the DMO record to indicate the findings so far. From step 522, control returns via node 526. But if at test 520, the symptom is judged to be mild, then process 482 passes control to node 524, which sets the DMO record to indicate need for normal health assessment. From node 524, process 482 returns control via node 526.

If, at node 516, the patient does not have a related symptom, process 482 needs to determine whether or not the patient has a side effect related to the current therapy of the patient. To do this, process 482 passes control first to step 530, which looks up the patient's symptom in a table of side effects of the current therapy. Process 482 next passes control to test 532, which is a filter that determines side effect symptoms. If the patient's symptom is a side effect, process 482 invokes the Severity Assessment function 520 to classify the side effect as mild or severe. For mild side effects, process 482 passes control to node 536, which sets the DMO record to be assessed by subsequent processing. For severe side effects, process 482 passes control first to step 534, which marks the DMO record to refer the patient out of the system to a human physician, and then returns to the calling process via node 526.

If, at test 532, the patient's symptom is not a side effect, the symptom is a significant symptom unrelated to either the disease being managed or to the therapy being applied. Process 482 invokes the Severity Assessment function 520 to classify the symptom as mild or severe. For mild symptoms, process 482 passes control to node 542, which sets the DMO record flag to force a special discussion with the patient after all DM processing is performed, and notes the reasons for the discussion. Then process 482 passes control first to node 544 which sets the DMO record to force subsequent health assessment and next to node 526, which returns to the process that called process 482. For severe unrelated symptoms, process 482 passes control first to step 540, which marks the DMO record to refer the patient out of the system to a human physician, and then returns to the calling process via node 526.

Severity Assessment

Figure 9:
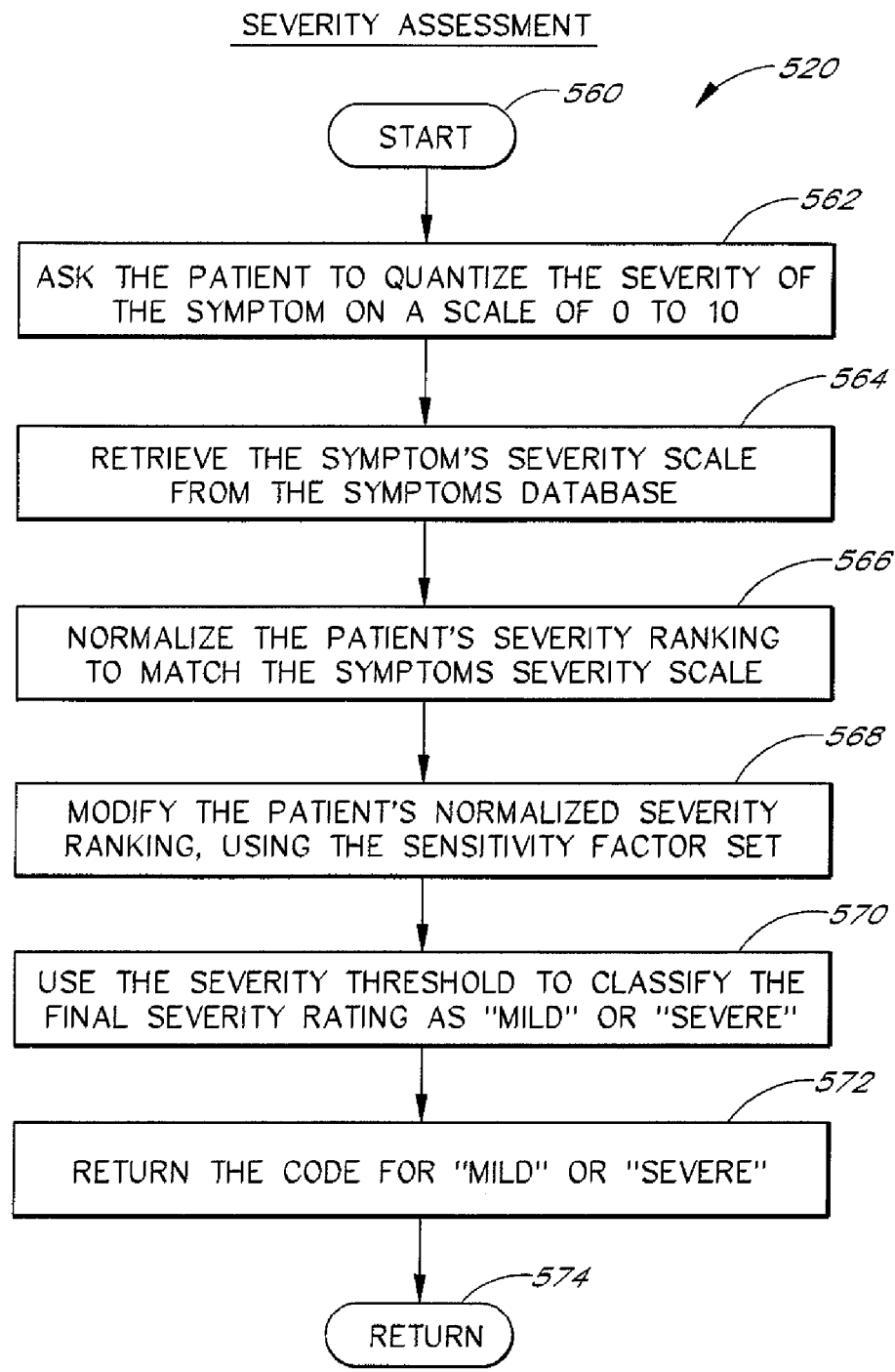
FIG. 9 is a flowchart of the Severity Assessment function shown in FIG. 8.

Referring to FIG. 9, the Severity Assessment function 520 will be described. This function uses a number of criteria to decide whether a given symptom is to be considered mild or severe for the DM assessment purposes. Function 520 receives control at start node 560, where it begins a sequence of 6 consecutive steps and then returns the computed result. First, function 520 passes control to node 562, which asks the patient to rank the symptom's severity on a scale of 0 to 10. Next, function 520 passes control to node 564, which obtains the absolute severity scale of the symptom itself from the symptoms database. Different symptoms have different severity scales, and the patient's ranking is now matched to that of the symptom. Therefor, next, function 520 passes control to node 566, which normalizes the patient's ranking, so that it is expressed in terms of the symptom's severity scale. Next, function 520 passes control to node 568, which uses the Sensitivity Factor Set to adjust the normalized severity ranking up or down, depending on the current sensitivity setting of the DMM. Thus, the higher the Sensitivity, the more conservative the system is in its assessments. At the lowest Sensitivity setting, all symptoms severity ratings will be considered mild. Next, function 520 passes control to node 570, which converts the final adjusted ranking into 2 classifications, mild or severe. It is important to note that this final step can, in other contexts, classify the final ranking into any number of gradations; but for the current assessment purpose, the symptom must be classified as mild or severe. Next, function 520 passes control to node 572, which returns a code for either "mild" or "severe" to the calling process.

Initial Health Assessment

Figure 10:
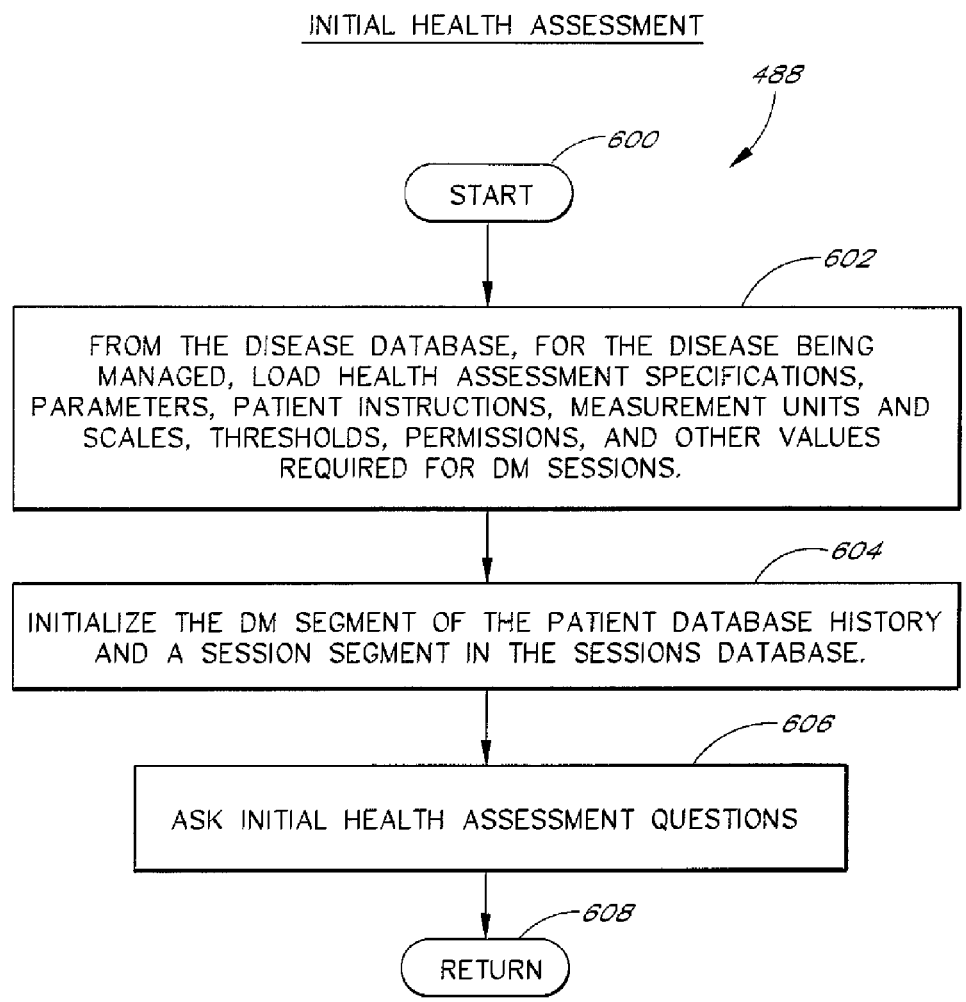
FIG. 10 is a flowchart of the Initial Health Assessment process shown in FIG. 7.

Referring to FIG. 10, the process 488 will be described. This process performs a health assessment for patients who are having their first Disease Management session. Process 488 receives control at node 600. Process 488 then passes control to node 602, which loads the health assessment specifications for the disease being managed from the disease database. These specifications include various parameters to be used in Disease Management sessions, such as patient instructions, choices of therapies, permissions required, and so on. After these values are obtained, process 488 passes control to node 604, which initializes a DM session segment in the patient's medical history and the sessions database. Then, process 488 passes control to node 606, which conducts an initial health interview to ask the patient for a subjective assessment of current health, for any objective health measurements the patient may have available, any pre-existing therapy or side effects, and so on. Then process 488 passes control to node 608, which returns control to the calling process.

Current Health Assessment

Figure 11:
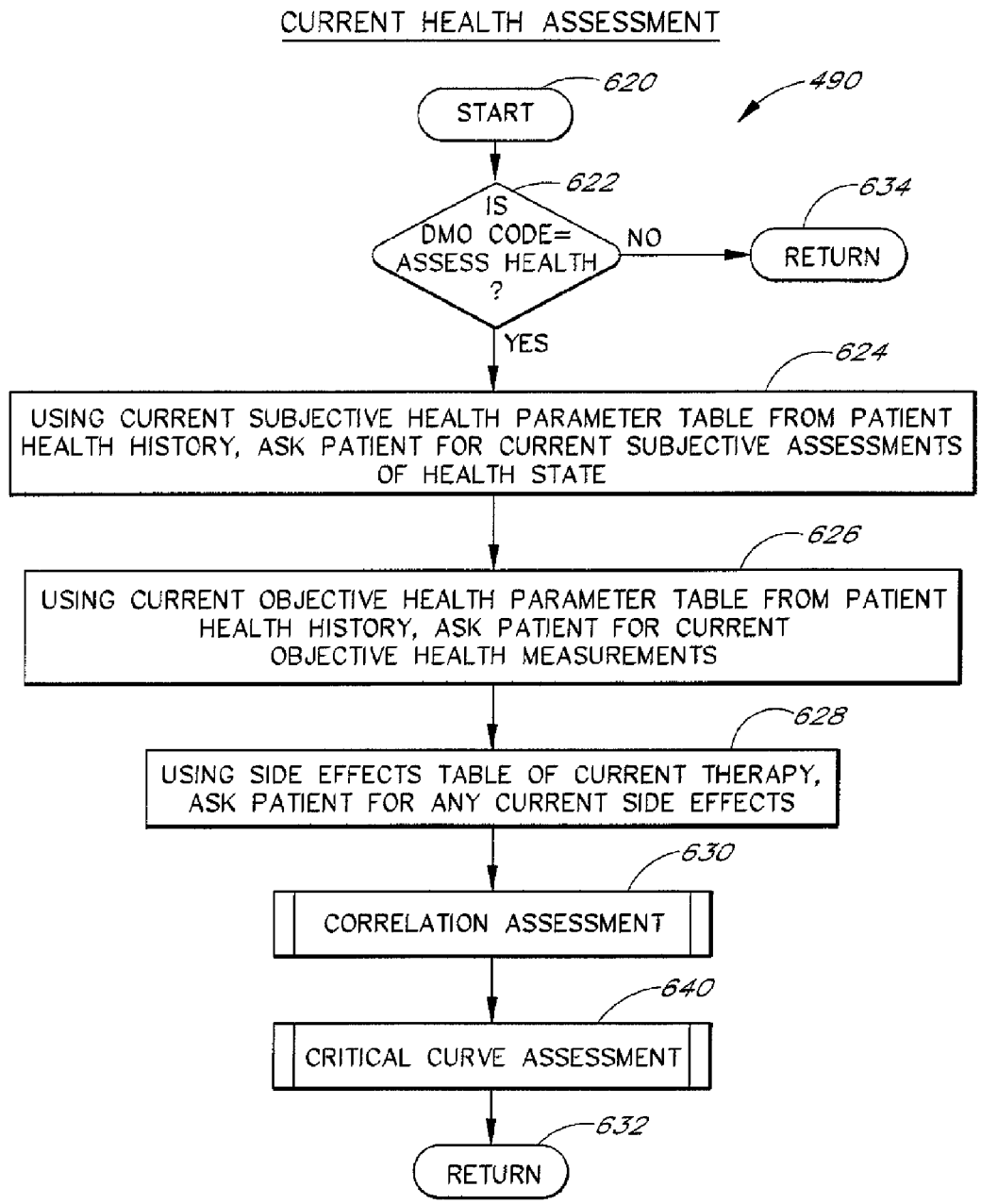
FIG. 11 is a flowchart of the Current Health Assessment process shown in FIG. 7.

Referring to FIG. 11, the process 490 will be described. This process obtains current health data from the patient in three forms: subjective (i.e. as perceived or felt by the patient), objective (i.e. as measured by the patient, typically with an instrument), and side effects noted by the patient. These health measurements are then used to analyze the current health state. Process 490 receives control at node 620. From node 620, process 490 passes control to test 622, which examines the current DMO record of the patient to determine what processing has been done and what needs to be done. If the DMO record code does not indicate that a health assessment is required, process 490 passes control to node 634, which returns control to the calling process. If a health assessment is required, process 490 passes control to a sequence of 5 steps that obtain various health assessments. First, process 490 passes control to step 624, which asks the patient for a subjective assessment of the patient's current health state. Next, process 490 passes control to step 626, which asks the patient for objective health measurements of the patient's current health state. Next, process 490 passes control to step 628, which asks the patient for any current side effects. Next, process 490 invokes the Correlation Assessment function 630. This function is described in conjunction with FIG. 12. Next, process 490 passes invokes the Critical Curve Assessment function 640. This function is described in conjunction with FIG. 13. Next, process 490 passes control to step 632, which returns control to the calling process.

Correlation Assessment

Figure 12:
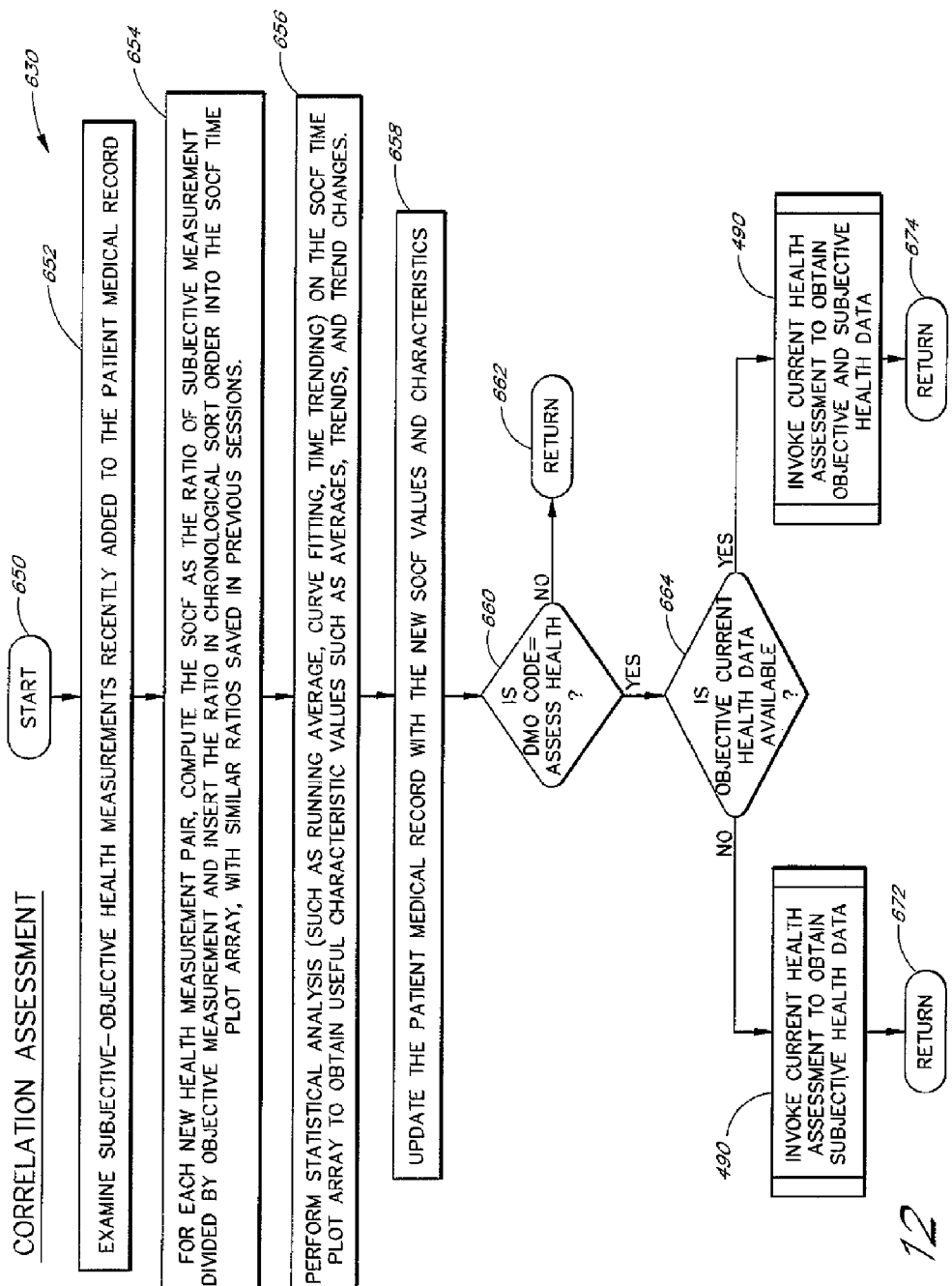
FIG. 12 is a flowchart of the Correlation Assessment function shown in FIG. 11.

Referring to FIG. 12, the process 630 will be described. This function computes and standardizes the SOCF for recently added data, computes other assessment parameters and statistics, and updates the patient medical history. Finally, it invokes the health assessment function again to fill in data gaps for the interval since the last session.

Process 630 receives control at start node 650. Then process 630 passes control to step 652, which obtains any new health data that have been added to the patient's medical history since the last DM session. Then process 630 passes control to step 654, which computes new points on the raw SOCF time plot by taking the ratio of subjective to objective measurement for the same time and updating the raw SOCF time plot array with the new points. Then process 630 passes control to step 656, which applies standard statistical normalization and curve-fitting techniques to normalize the raw SOCF points and obtain a single current SOCF that is high in patients whose subjective assessment tends to match their objective health measurements, and low in patients whose subjective assessments tend to be inaccurate by comparison with their objective health measurements. Step 656 also computes other parameters used in the rest of the DM session, such as the slope and slope trend for the most recent 3 data points and the difference between patient's measurements and normal measurements. Step 656 also determines whether there are large gaps in the patient's health data, that need to be filled retroactively in by an interval assessment. Step 656 sets the DMO code appropriately to call for another assessment. Then process 630 passes control to step 658, which updates the patient's medical history with the computed assessment parameters. Then process 630 passes control to test 660, which determines whether the patient's health is to be assessed again for missing interval data. If test 660 determines that no further assessment is required, process 630 passes control to terminal node 662, which returns control to the calling process. If test 660 determines that another round of health assessment is required, process 630 passes control to test 664. Test 664 determines the type of data to be re-assessed for the interval. If test 664 determines that objective data are available, process 630 invokes Health Assessment process 490, passing a parameter that asks for both subjective and objective patient health data to be assessed for the interval. Then process 630 passes control to terminal node 674, which returns control to the calling process. If test 664 determines that objective data are not available, process 630 invokes Health Assessment process 490, passing a parameter that asks for only subjective patient health assessments to be obtained for the interval. Then process 630 passes control to terminal node 672, which returns control to the calling process.

Critical Curve Assessment

Critical Curve Assessment is a DMM process for monitoring patient health for significant deterioration. A critical curve is defined as a plot of a health measurement against time that is used to identify significant changes in health state. The Critical Curve Assessment process selects a disease- and patient-specific health parameter, plots it as a critical curve, updates the critical curve as a normal part of continuing DM sessions, and takes specific action if the patient's critical curve exhibits specific critical points, slopes, and slope trends. The process is based on comparing the patient's critical curve to standard, disease-specific critical curves. A constant, high ordinate value indicates good health; a declining curve indicates declining health; a sharp drop in the curve indicates a health crisis. The "critical point" on the curve is a point that predicts a significant decline in health.

Figure 23:
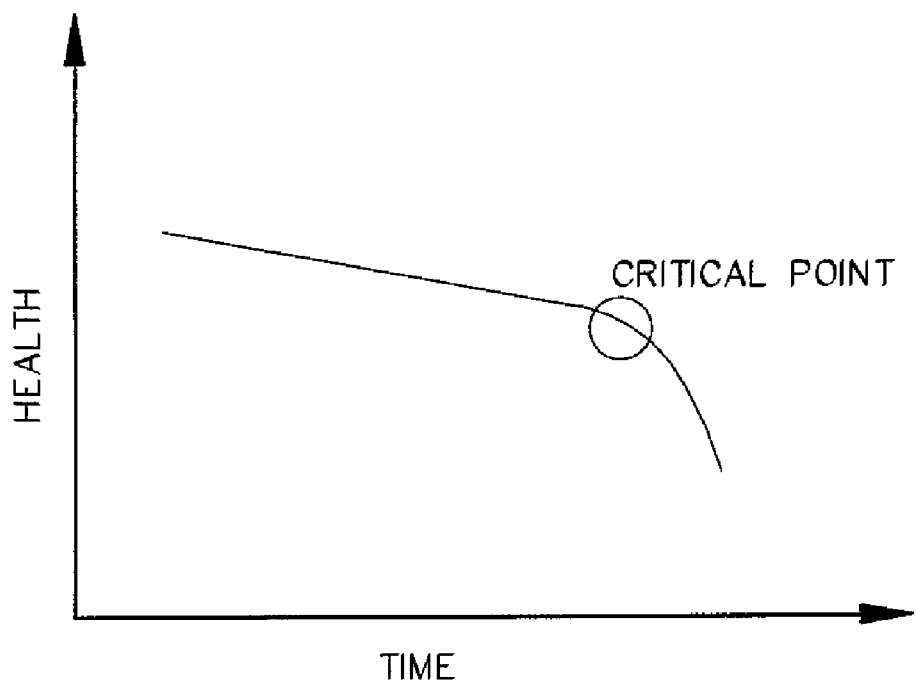
FIG. 23 is a graph of an exemplary critical curve plotting health measurements over time for a particular disease.

An example of a generic critical curve is shown in FIG. 23, which contains a point circled as the "critical point". Referring to FIG. 23, it will be noted that, at the critical point, the slope of the curve (i.e. the line tangent to the curve at the critical point) is sharply negative, which predicts that the next health measurement will be lower than the critical point. Moreover, at the critical point, the rate of slope change may also be negative, indicating that the slope of the curve is decreasing even more, predicts a rapidly deteriorating health state. For brevity, these three critical test items are typically referred to in the DMM processes as the critical point, slope, and trend. They are calculated using the last three health measurement points. For critical curves with sufficient data points, curve fitting techniques can also be used.

The DMM has a database of diseases 262 (FIG. 3) that contain standard critical curves for various diseases, patient populations, and health parameters. The Critical Curve Assessment process extracts the appropriate disease data set, selects an appropriate health parameter to be used, adapts it for the current patient, and saves it as the standard curve for the current patient in the patient's medical history 254 (FIG. 3). As the DMM periodically dialogs with the patient, the Critical Curve Assessment process obtains current data from the patient, plots them on the patient's critical curve, and uses curve-fitting and pattern matching techniques to compare the patient's actual CC to the patient's standard CC. This comparison enables the DMM to detect key points and trends on the patient's curve, such as the "critical point" that predicts a significant impending health decline. When the curve approaches this critical point, the Critical Curve Assessment method orders alterations in therapy that will prevent the predicted deterioration, or sets a flag to refer the patient to a health care provider. Both objective and subjective health data are used to plot the CC, especially if the Subjective-Objective Correlation Factor (SOCF) is high (which means that the patient knows his/her disease process well and the DMM can rely on the patient's responses more and more).

Homeostasis

The concept of homeostasis, as described by Claude Bernard, is helpful in understanding the concepts behind the Critical Curve and its analysis. Briefly, homeostasis is a state of dynamic equilibrium of the body. This equilibrium is maintained by various internal control mechanisms that force certain system parameters to remain within a desired range. Using these homeostatic mechanisms, the body is able to tolerate disease up to a certain point, at which time progression of the disease begins to accelerate. Good examples of this are:

the bicarbonate buffering system for maintenance of blood pH,
the oxyhemoglobin disassociation curve, and
the deterioration of a patient with chronic obstructive pulmonary disease.

The Critical Curve

The Critical Curve (CC) describes the patient's health state during a bout with disease. The curve plots the patient's health state against time, starting initially at a (high) normal state of health and descending—as the disease progresses—to a lower state of health.

A normal, disease-free patient will have a fairly steady plot at a high level of health. The initial part of the curve is asymptotic to normal health because the healthy body can often resist disease for some time by using reserve capacities and internal defense mechanisms. After the initial phase, the health curve begins to descend at a steeper and steeper angle, as reserves are used up and the disease is established and produces secondary effects. At some critical point, the curve steepens so dramatically that the patient's condition may deteriorate quickly.

Many physiologic parameters have a characteristic response to change, being able to compensate up to a point, and then responding with very large changes in signal findings to small changes in the progression of the disease. It is very important to know where the patient is on the Critical Curve, because if the expression of the disease in this patient is about to accelerate significant intervention is required. When there is an indication or even a suspicion that the patient's condition is approaching the steep area of the health curve, the DMM can recommend a change in therapy or consultation with the patient's health caregiver. If confirmation of the change of the health state is required, the DMM reenter feature allows the DMM system to confirm its hypothesis before making recommendations.

Critical Curve Analysis

For a patient with a known disease, who is managing the disease at home with suitable maintenance therapy, the DMM monitors the patient's periodic contacts and health state reports. When the trend line indicates that the patient's health curve is reaching the critical point, the DMM can change the therapy and/or notify the patient's physician. Since patients can go for months successfully managing their disease, this Curve analysis approach can save a significant number of unnecessary physician visits, yet inform the physician and the patient at once when a change in health state indicates that the critical point is being approached.

Obviously, it is best to use an easily quantifiable parameter as a marker for the progression of the disease in question to embody this curve, but if the subjective-objective correlation is high in a given patient, their subjective evaluation can accomplish the same thing.

The system measures the tidal volume and peak flow rates over time. If it is found that small changes in tidal volume make large differences in the patient's impression of the severity of their disease (compared to the changes made previously in this patient), the patient is on the steep part of the curve. A flag is set and significant intervention is necessary.

If the therapeutic alteration permission level is set low, then the patient is referred to his physician, and the patient's doctor receives a report, frequently a fax, e-mail or downloads about the new developments. If the therapeutic alteration level is set high, then therapeutic optimization may occur before the patient sees his physician. A report is sent to the physician and the patient may or may not have to be seen.

It is this analysis and the recognition of this relationship that constitutes the "curve" analysis of the health state.

Example

Chronic Obstructive Pulmonary Disease

We will discuss chronic obstructive pulmonary disease as an example. Chronic obstructive pulmonary disease slowly destroys lung tissue. As mentioned, many physiologic parameters have the same response to changes, being able to compensate up to a point, and then, after that reserve capacity is gone, very small changes in the disease state produce very large changes in the expression of the progression of the disease in the patient its early phase, the patient with chronic obstructive pulmonary disease loses only reserve lung capacity, so there is no significant change in the resting health state. After the reserve tissue has been destroyed, a threshold is reached beyond which smaller and smaller time increments (and progression of the disease process) will produce more and more profound deterioration in the patient's ability to blow off carbon dioxide and oxygenate the blood. Ultimately, even a very small change in chronic obstructive pulmonary disease results in respiratory failure.

When we start to see larger and larger decrements to pulmonary function plotted against time, the patient is reaching the critical part of the curve. Significant intervention is necessary and should be started as soon as possible.

The Critical Curve Assessment process is especially effective in the DMM setting because the DMM:
- is fully automated,
- tracks patient health through time,
- has various modules that track and correlate patient contacts,
- knows the patient (history, Subjective-Objective Correlation Factor)
- has access to databases of medical knowledge,
- can analyze disease progress using mathematical trend analysis, and
- can select alternate therapies as required by altered conditions.

Figure 13A:
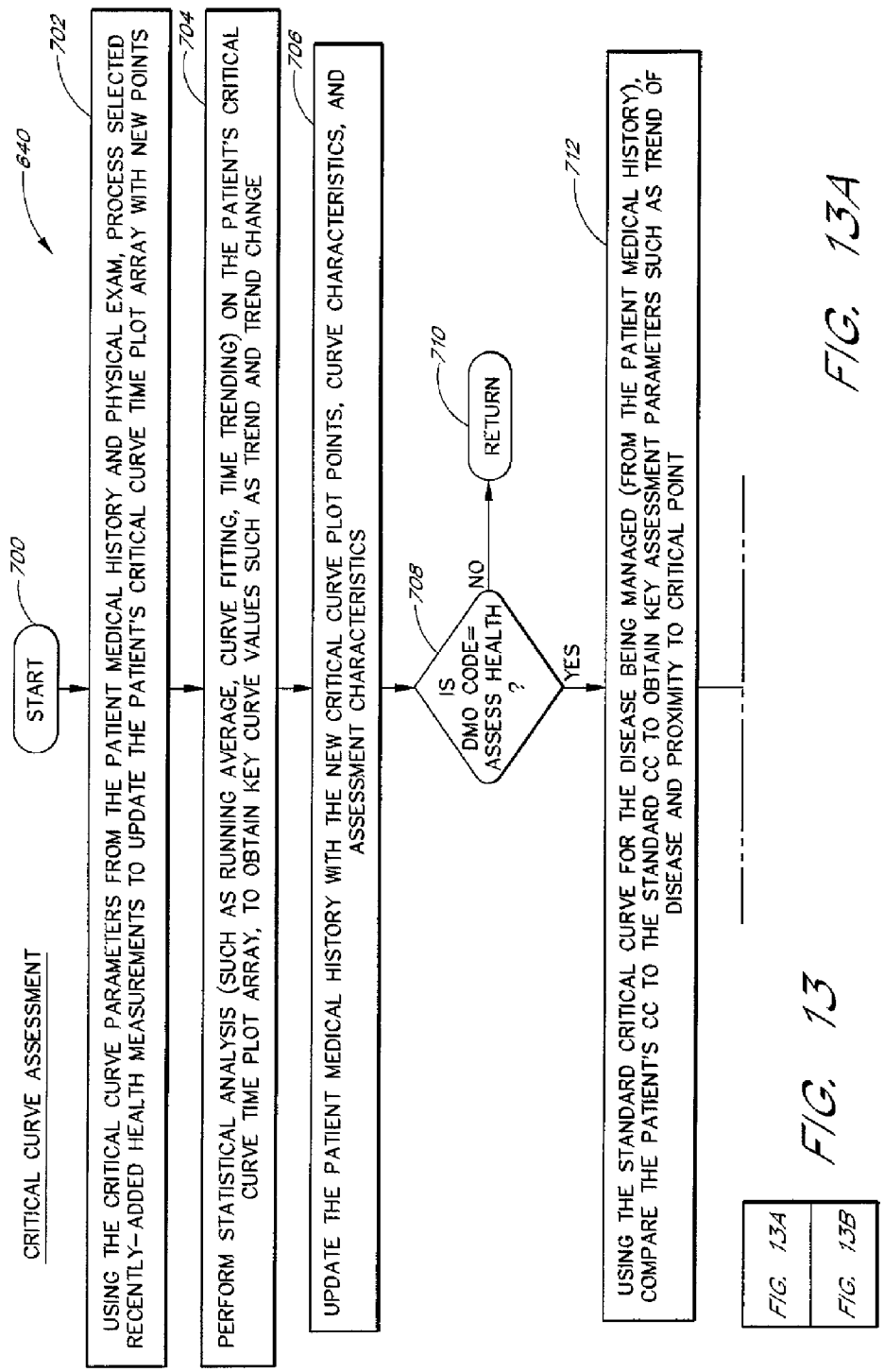
FIG. 13 is a flowchart of the Critical Curve Assessment process shown in FIG. 11.
Figure 13B:
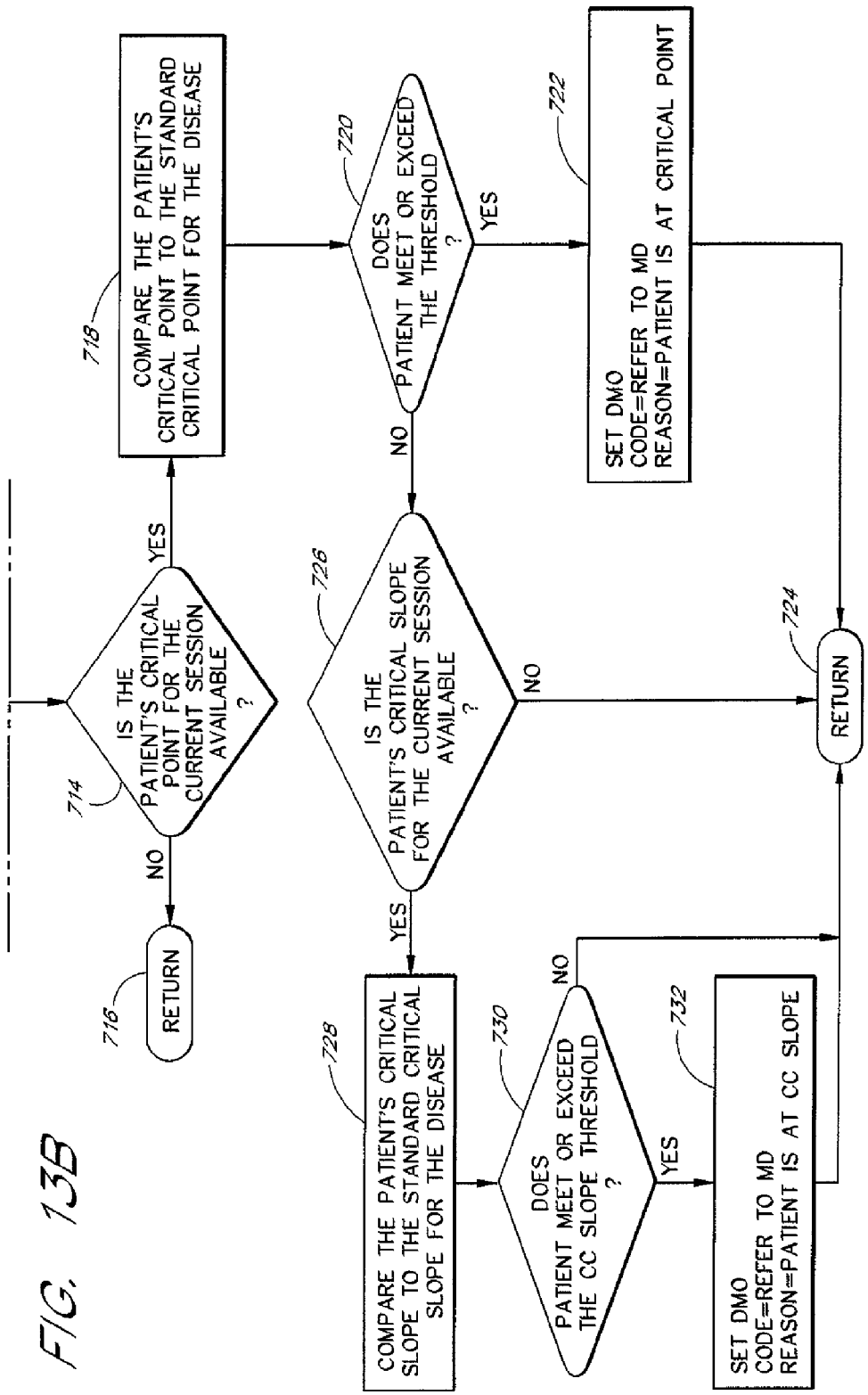

Referring to FIG. 13, the Critical Curve Assessment function 640 will be described. This function has two phases. The first phase (starting at node 702) updates the patient's critical curve with health measurements added to the patient's medical history since the last critical curve assessment. The second phase (starting at node 712) compares the patient's actual critical curve to the standard critical curve used for this patient. If a patient is at (or is approaching) a critical part of the curve, this suggests the possibility of rapid deterioration of the disease being managed, and the patient is referred to a human physician for consultation.

Process 640 receives control at start node 700. Then process 640 passes control to step 702, which updates the patient's actual critical curve with new health measurements. Next, process 640 passes control to step 704, which analyzes the patient's updated critical curve to obtain the latest critical curve point, slope, and 3-point trend. Next process 640 passes control to step 706, which saves the patient's critical curve data in the patient medical history. Next, process 640 passes control to test 708, which examines the DMO record code to see whether the patient's critical points should be assessed. If the patient's critical points should not be assessed, process 640 passes control to terminal node 710, which returns control to the calling process. If the test 708 indicates that health assessment is needed, process 640 passes control to step 712.

Step 712 begins the assessment phase of process 640. Step 712 retrieves or computes the working data needed to use the critical curve to assess patient health. Working data include the patient's latest actual health point and slope, the matching point and slope on the patient's standard critical curve, and the thresholds used to rule the patient as critical for each set. When step 712 has computed these working data, process 640 passes control to test 714.

Test 714 begins a sequence of steps that examine the patient's critical point. If test 714 finds that the patient's latest health point is not available or cannot be matched on the standard curve, process 640 passes control to terminal node 716 which passes control to the calling process. If test 714 determines that the latest health point is available, then process 640 passes control to step 718 which compares the difference between the actual and standard critical health points. Then process 640 passes control to test 720. If test 720 finds that the patient does meet or exceed the critical point threshold, process 640 passes control to step 722, which sets the DMO record to refer the patient to a human physician for consultation. Then process 640 passes control to terminal node 724, which returns control to the calling process. If test 720 finds that the patient does not meet the critical point threshold, process 640 passes control to test 726.

Test 726 begins a sequence of steps that examine the patient's critical slope. If test 726 determines that the critical slope is not available, process 640 passes control to terminal node 724 which returns control to the calling process. If test 726 determines that the actual slope is available, process 640 passes control to 728, which compares the difference between the actual and standard critical slopes. Then process 640 passes control to test 730. If test 730 determines that the patient is below the critical slope threshold, process 640 passes control to node 724, which returns control to the calling process. If test 730 determines that the patient does meet or exceed the critical slope threshold, process 640 passes control to node 732, which sets the DMO record to refer the patient to a human physician for consultation. Then process 640 passes control to node 724, which returns control to the calling process.

Therapy Optimization

Therapy Optimization consists of a set of processes that review and adjust patient therapy from session to session, with a long-term goal of maximizing efficacy, minimizing adverse side effects, and maintain patient cooperation and acceptance of the recommended therapy. The Therapy Optimization processes select therapy parameters from medical treatment tables and track patient-specific efficacy by reviewing subjective and objective patient health data from session to session. The Therapy Optimization process selects from multiple therapies. It seeks to minimize side effects by offering the patient the choice of alternate therapies, and by adjusting therapy dosage levels until the patient finds the appropriate comfort level. Disagreements between the DMM and the patient are resolved by referring the patient to a human physician for face-to-face consultation and advice. Therapy Optimization is guided and controlled by the Therapy Optimization Permission Level (TAPL), a DMM-global variable that specifies the amount of autonomy that the DMM has to alter therapy. The TAPL is described in a separate section below.

After the patient health state has been assessed, the Therapy Optimization process reviews and adjusts (to the extent the TAPL allows it) the patient's treatment to achieve the best combination of several subgoals of the overall goal of restoring normal health. The Therapy Optimization process also seeks to minimize treatment side effects. To the extent allowed by the current TAPL setting, the DMM will gradually titrate the dose of a medication until the benefit/side effect ratio is maximized. The overall idea is to achieve the desired physiological changes with the fewest side effects. Initial treatment is selected from a treatment table based on disease, age, and sex. Due to the wide range of responses to treatments by different patients, once a drug has been selected as the therapy for a given disease, the different formulation, dosing, administering methods and timing are, in effect, a matter of trial and error for a specific patient. To review therapy, the Therapy Optimization task compares the patient's current therapy to the treatment table to detect and analyze differences. If a new treatment is available, the patient and the healthcare giver are notified, and the therapy may be altered, depending on the TAPL. To maximize the therapeutic result and minimize side effects, the Function can select the initial therapy, review the patient's current therapy, adjust various parameters of the therapy, and monitor the effect of these changes.

Therapy parameters that can be changed include drug class, type, brand, dose, route, mode of drug administration, formulation, timing, and frequency. As each of these is modified, the patient's health data and side effects are checked to see if the current modification of therapy makes the patient better, and so on. Each therapy parameter is sequentially altered on a trial and error basis to find the overall best combination of therapy parameters. When the DMM adjusts a patient's therapy, it adjusts the DM session schedule appropriately, typically instructing the patient to re-enter the system within a few iterations of therapy or dosage.

Side effect minimization is a special goal of the Therapy Optimization process, which seeks to reduce the undesirable side effects of therapy. This task illustrates the complex, trial-and-error methods used by the DMM to Therapy Optimization feature. Example 1: In cancer patients there is a point at which patients receiving chemotherapy decide that the side effects are not worth the slowing of the progression of the disease. At that point, one "backs off" (decreases the dosage), knowing that any further increase will be futile. The process becomes more complicated if multiple drugs are involved, but the same relationships hold. Example 2: Albuterol-metered dose inhalers help the wheezing of asthma patients, but at a certain patient-specific dose, the side effects get so bad, that the patient cannot tolerate them. At that point, the dosage is backed off in small steps to get the best ratio of efficacy to side effects.

Referring to FIG. 14, the Therapy Optimization process 408 will be described. Process 408 performs the therapy phase of the DM session. This phase computes the next best therapy step that is accepted by the patient, using two major subordinate processes and a loop that tries various therapies until the patient accepts one. The general goal of process 408 is to select therapy steps in a manner that optimizes therapy over the long term, by maximizing efficacy, minimizing side effects, and adjusting therapy types and modalities to meet the patient's comfort level. Process 408 receives control at start node 760. Then, process 408 passes control to test 762, which tests whether the patient provided current objective health measurements during the earlier part of this DM session. If test 762 finds that the patient did not provide current objective health data, process 408 passes control to test 782, which tests whether the patient entered a subjective assessment of his/her health during the earlier part of the DM session. If test 782 finds that the patient provided a subjective health assessment, process 408 invokes process 790. Process 790 adjusts the therapy based on current subjective health data. Process 790 is detailed below in conjunction with FIG. 15. When process 790 returns control, process 408 passes control to terminal node 792, which returns control to the calling process. If test 782 finds that the patient did not provide a current subjective health assessment, process 408 passes control to 784, which sets the DMO record to refer the patient to a human physician for consultation. Then, process 408 passes control to terminal node 786, which returns control to the calling process.

If test 762 finds that the patient did provide current objective health data, process 408 passes control to step 764, which initializes a loop that will try various therapies until the patient accepts one or until the number of retries is exhausted, whichever occurs first. Step 764 obtains the maximum number of therapy permitted from the permissions database for this patient. Then, process 408 invokes process 770. Process 770 selects the next best therapy from the treatment table for this patient and offers it to the patient who can accept or modify or reject it. Process 770 is further described below in conjunction with FIG. 16. When process 770 returns control, process 408 passes control to test 772. If test 772 determines that the patient accepted the therapy recommended, process 408 passes control to terminal node 780, which returns control to the calling process.

If test 772 determines that the patient rejected the therapy recommended, process 408 passes control to test 774. If test 774 determines that the loop retry count is greater than one, process 408 passes control to step 776. Step 776 reduces the loop retry count by 1 and then process 408 invokes process 770 again for another iteration of the loop. If test 774 determines that the retry count is 1, then process 408 passes control to step 778. Step 778 sets the DMO record to refer the patient to a human physician for consultation. Then, process 408 passes control to terminal node 780, which returns control to the calling process.

Therapy Adjustment (Subjective)

Figure 15A:
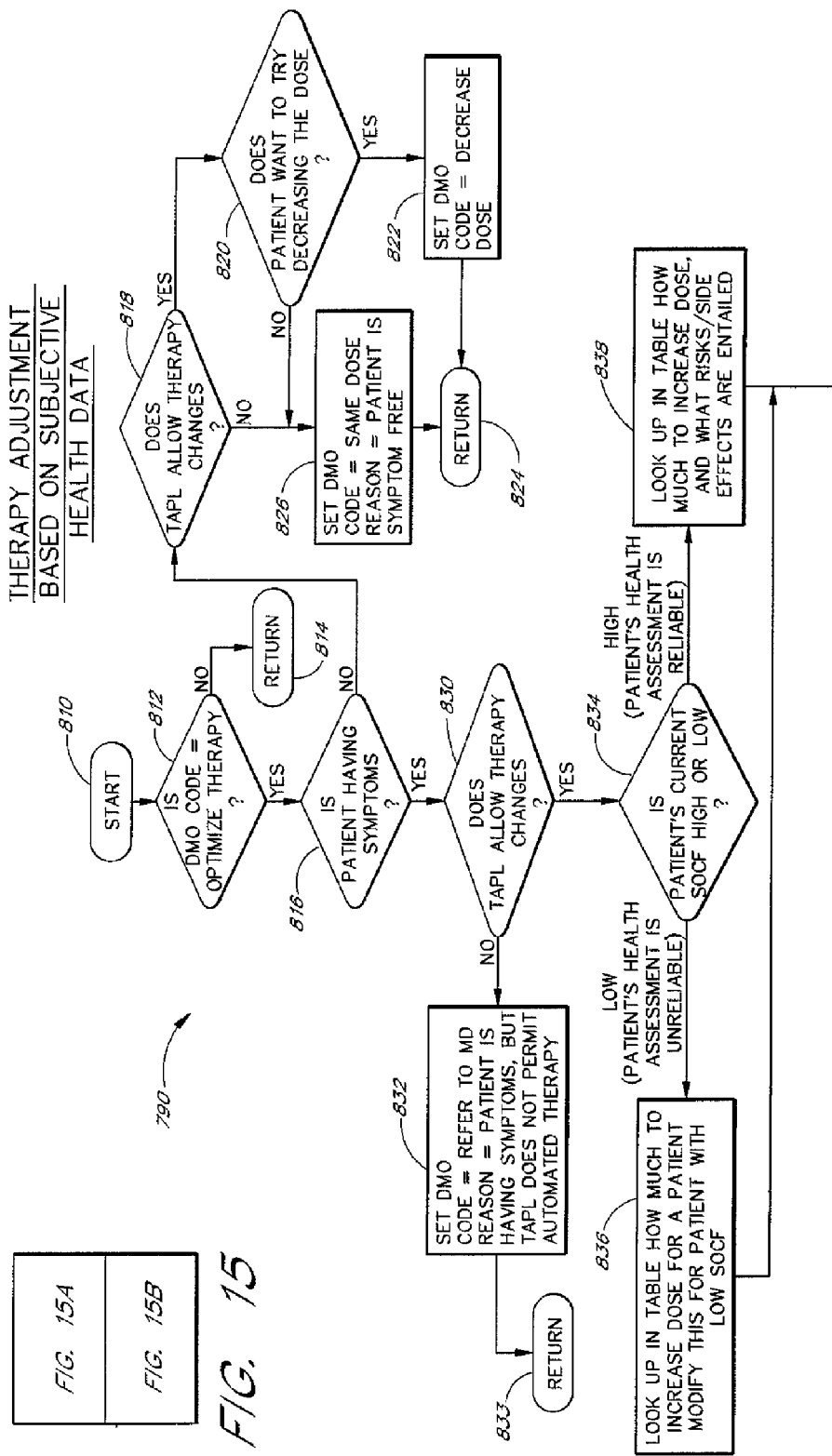
FIG. 15 is a flowchart of the Therapy Adjustment Based on Subjective Health Data process shown in FIG. 14.
Figure 15B:
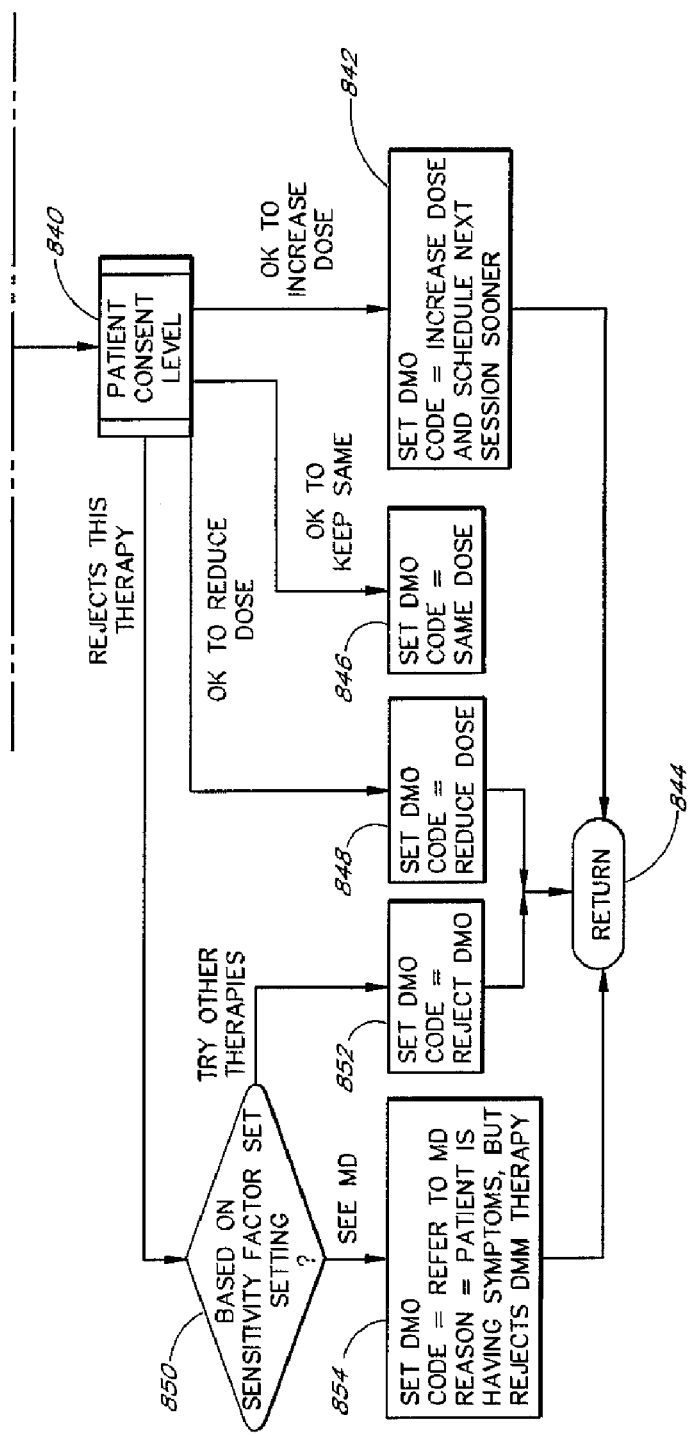

Referring to FIG. 15, the process 790 will be described. Process 790 computes the next best therapy for this patient, based only on the patient's subjective assessments of his/her health. Process 790 uses the Subjective-Objective Correlation Factor (SOCF) which is described below in the section Subjective-Objective Correlation Factor. The SOCF indicates how reliable this patient is in subjectively assessing his/her disease, and process 790 relies on the SOCF in computing the next therapy step.

Process 790 receives control at start node 810. Then, process 790 passes control to test 812. If test 812 determines that the patient does not need therapy adjustment, i.e. that the DMO record of this patient has already been completed for an approved therapy, process 790 passes control to terminal node 814 which returns control to the calling process. If test 812 determines that this patient requires therapy optimization, process 790 passes control to test 816. Test 816 determines (by asking the patient or by obtaining the patient's saved response if the patient has already been asked) whether the patient is having any current symptoms. If test 816 finds that the patient is symptom-free, process 790 passes control to test 818. If test 818 determines that the current DMM TAPL setting does not permit therapy adjustments, process 790 passes control to node 826, which sets the DMO record to maintain the same therapy, e.g. the same dose in the case of a drug-based therapy. Then, process 790 passes control to terminal node 824, which returns control to the calling process.

If test 818 determines that the current TAPL setting does permit therapy adjustments, process 790 passes control to test 820. If test 820 determines that the patient does not want to try to reduce the dose, process 790 passes control to step 826, which sets the DMO record to maintain the same therapy. Then, process 790 passes control to terminal node 824, which returns control to the calling process. If test 820 determines that the patient wants to reduce the dose, process 790 passes control to step 822, which looks up the next lower dosage level in the treatment table and sets the DMO record to decrease the dose. Then, process 790 passes control to terminal node 824, which returns control to the calling process.

If test 816 finds that the patient is having current symptoms, process 790 passes control to test 830. If test 830 finds that the TAPL does not permit changes in therapy, process 790 passes control to step 832. Step 832 sets the DMO record to refer the patient to a human physician for consultation. Then, process 790 passes control to terminal node 833 returns control to the calling process. If test 830 finds that the TAPL does permit changes in therapy, process 790 passes control to step 834.

Step 834 begins that phase of process 790 which computes the next therapy step for a patient who is having symptoms, but has only reported current subjective health assessments. Step 834 uses the current SOCF from the patient's medical history, modifies it by the current Sensitivity Factor Set to adjust it to the sensitivity being used for this patient, and then classifies the patient's current SOCF as "high" or "low" for the purpose at hand. If test 834 classifies the patient's SOCF as high, the patient's subjective health assessment is reliable, and process 790 passes control to step 838 which looks up in the treatment table how much the therapy (i.e. dose in the example drawn) can be increased for a patient with a high SOCF, and what the associated benefits and risks are. Then, process 790 invokes function 840. Alternatively, if test 834 deems the SOCF as low, process 790 passes control to step 836, which obtains the dose and risk/benefit factors for unreliable patients. In either case, process 790 continues by invoking function 840.

The Patient Consent Level function 840 presents a recommended therapy to the patient and obtains a consent of the patient to the therapy as recommended or to some variation of it; the patient may also reject the recommended therapy entirely. Function 840 is described below in conjunction with FIG. 17.

When function 840 returns control, if function 840 returns the result that the patient consents to an increased dose, process 790 passes control to step 842. Step 842 sets the DMO record to indicate the next therapy with an increased dose, and with an appropriate change in schedule for a sooner DM session. Then, process 790 passes control to terminal node 844 which returns control to the calling process.

When function 840 returns control, if function 840 returns the result that the patient consents to continue therapy with the same dose, process 790 passes control to step 846. Step 846 sets the DMO record to indicate that the same therapy is to be continued. Then, process 790 passes control to terminal node 844 which returns control to the calling process.

When function 840 returns control, if function 840 returns the result that the patient consents to a reduced dose, process 790 passes control to step 848. Step 848 sets the DMO record to indicate the next therapy with a reduced dose. Then, process 790 passes control to terminal node 844 which returns control to the calling process.

When function 840 returns control, if function 840 returns the result that the patient rejects the recommended therapy at any level, process 790 passes control to test 850. Test 850 consults the current Sensitivity Factor Set to see whether process 790 should try the next best therapy or should refer the patient to a human physician. If test 850 determines that other therapies may be tried, process 790 passes control to node 852, which sets the DMO record to indicate that the patient rejected the recommended therapy. Then, process 790 passes control to terminal node 844, which returns control to the calling process. If test 850 determines that the patient should be referred, process 790 passes control to node 854, which sets the DMO record to refer the patient to a human physician. Then, process 790 passes control to terminal node 844 which returns control to the calling process.

Therapy Adjustment (Objective)

Figure 16A:
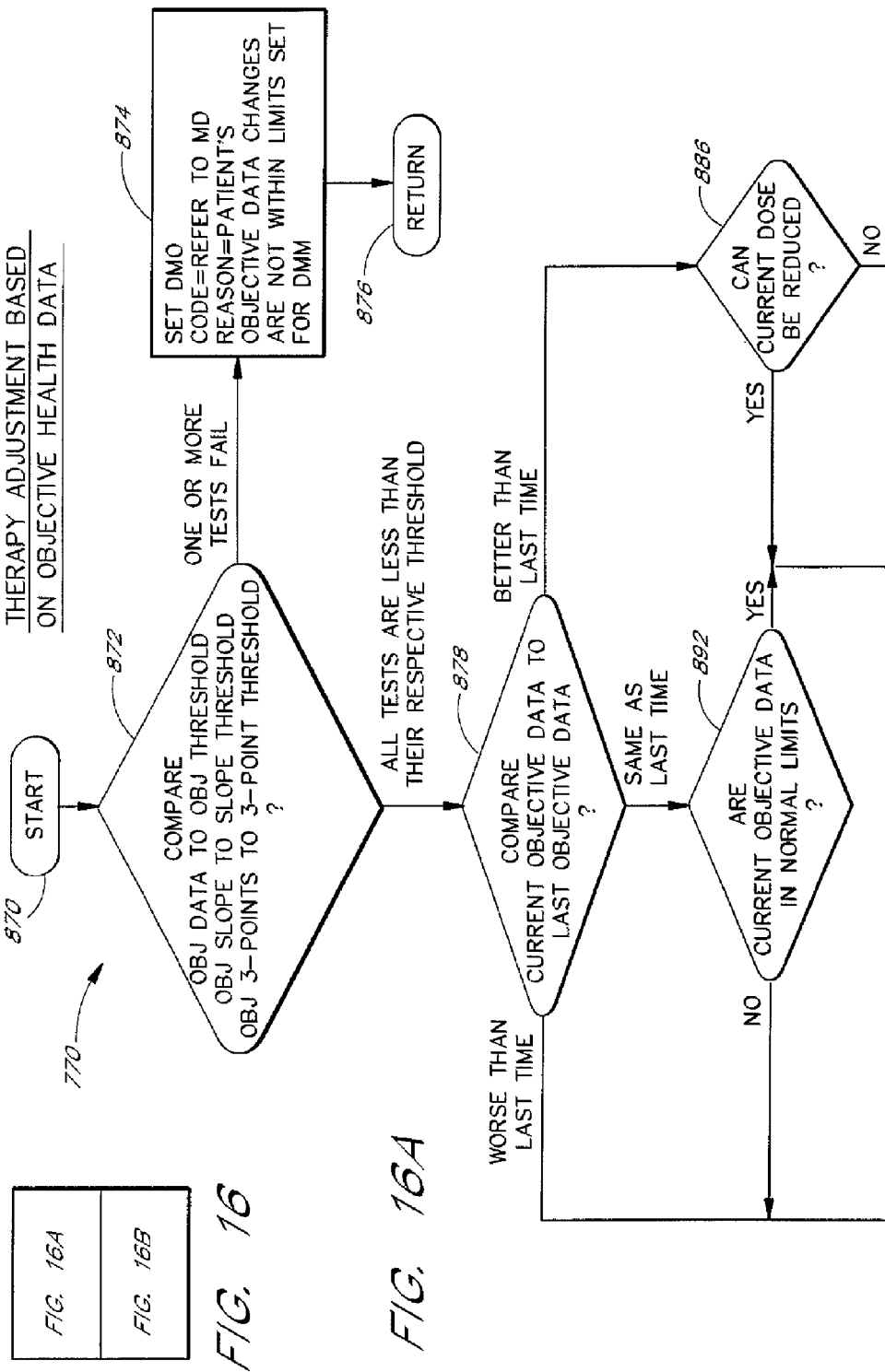
FIG. 16 is a flowchart of the Therapy Adjustment Based on Objective Health Data process shown in FIG. 14.
Figure 16B:
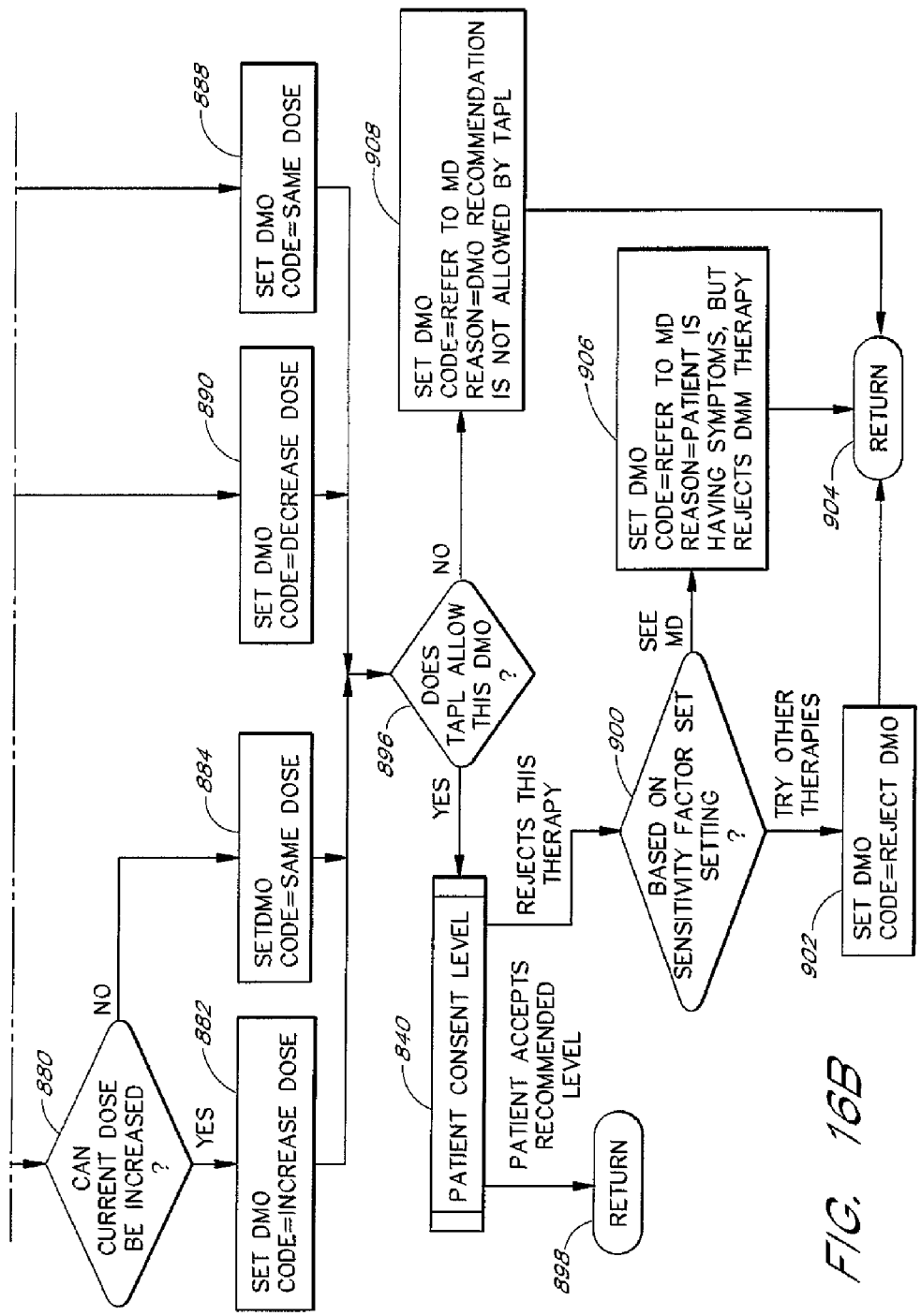

Referring to FIG. 16, the process 770 will be described. Process 770 computes the next best therapy for this patient, based on the patient's current objective health measurements. The process receives control at start node 870. Then, process 770 passes control to test 872. Test 872 compares health assessment parameters to determine whether the patient's objective health data meet or exceed various thresholds. Test 872 first compares the patient's current health measurement to an absolute threshold for that measurement, to see if the measurement itself is in acceptable range. Test 872 next compares the slope of the last two health measurements, to see if the patient's health is deteriorating at a rate that exceed a threshold. Test 872 next compares the change in the slopes of the last three measurements, to see if the patient's rate of change of health is getting worse more and more rapidly. If any one of these thresholds is met or exceeded, process 770 passes control to step 874, which sets the DMO to refer the patient to a human physician. Then, process 770 passes control to terminal node 876, which returns control to the calling process.

If test 872 determines that all of the patient's current health statistics are below threshold, process 770 passes control to test 878. Test 878 begins that phase of process 770 which computes the next recommended therapy for this patient. Test 878 compares the current patient health measurements to those of the previous DM session, to classify the patient's change of health state as "better, same, or worse" for the purpose of computing the next therapy step.

If test 878 determines that the patient is worse than the last time, process 770 passes control to test 880. Test 880 determines (from the treatment table) whether the current therapy dose can be increased. If test 880 determines that the dose can be increased, process 770 passes control to node 882, which sets the DMO to increase the dose. Then, process 770 passes control to test 896. If test 880 determines that the dose can not be increased, process 770 passes control to node 884, which sets the DMO to continue therapy with the same dose. Then, process 770 passes control to test 896.

If test 878 determines that the patient is in the same health as the last time, process 770 passes control to test 892. Test 892 determines whether the patient's current health measurements are in normal limits. If test 892 determines that the patient's current health data are normal, process 770 passes control to step 890. Step 890 sets the DMO to decrease the dose. Then process 770 passes control to 896. If test 892 determines that the patient's current health data are outside normal limits, process 770 passes control to test 880. Test 880 has been described above for process 770.

If test 878 determines that the patient is better than the last time, process 770 passes control to test 886. If test 886 determines (by consulting the treatment table) that the current dose can be reduced, process 770 passes control to step 890. Step 890 has been described above for process 770. If test 886 determines that the current dose can not be reduced, process 770 passes control to step 888, which sets the DMO to continue therapy with the same dose. Then, process 770 passes control to test 896.

Test 896 determines whether the TAPL setting for this patient allows the DMO as computed so far by process 770. If test 896 determines that the TAPL allows the DMO as written, process 870 invokes the Patient Consent Level function 840, which presents a recommended therapy to the patient and obtains a consent of the patient to the therapy as recommended or to some variation of it; the patient may also reject the recommended therapy entirely. Function 840 is described below in conjunction with FIG. 17. If function 840 returns the result that the patient accepts the recommended therapy (perhaps at some modified level), process 770 passes control to terminal node 898, which returns control to the calling process. If function 840 returns the result that the patient rejects the recommended therapy entirely, process 770 passes control to test 900. Test 900 consults the current Sensitivity Factor Set to see whether process 770 should try the next best therapy or should refer the patient to a human physician. If test 900 determines that other therapies may be tried, process 770 passes control to node 902, which sets the DMO record to indicate that the patient rejected the recommended therapy. Then, process 770 passes control to terminal node 904, which returns control to the calling process. If test 900 determines that the patient should consult a physician, process 770 passes control to node 906, which sets the DMO record to refer the patient to a human physician. Then, process 770 passes control to terminal node 904 which returns control to the calling process.

If test 896 determines that the TAPL does not allow the recommended therapy, process 770 passes control to step 908, which sets the DMO record to refer the patient to a human physician. Then, process 770 passes control to terminal node 904 which returns control to the calling process.

Patient Consent Level

Figure 17:
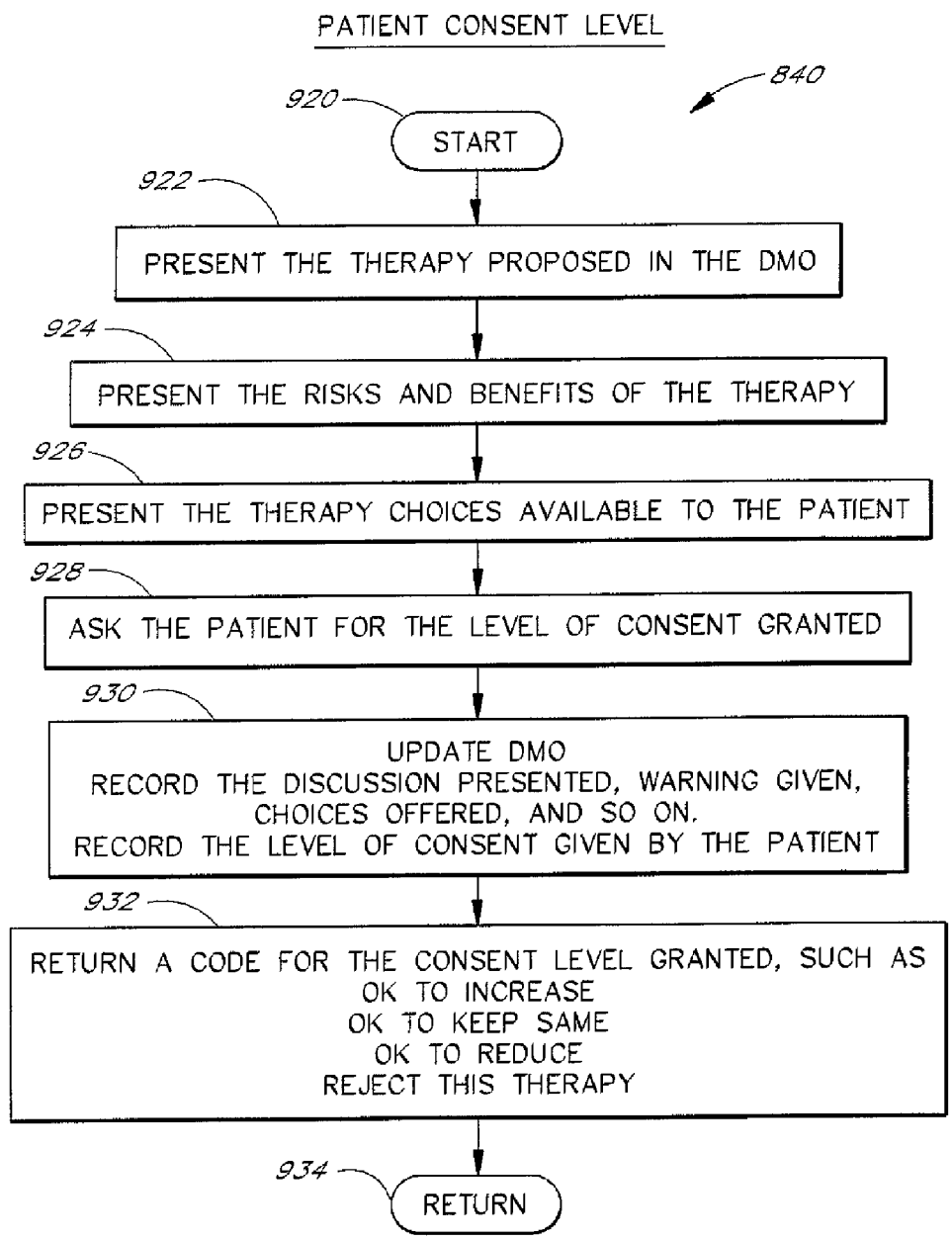
FIG. 17 is a flowchart of the Patient Consent Level function shown in FIGS. 15 and 16.

Referring to FIG. 17, the Patient Consent Level function 840 will be described. Function 840 presents a recommended therapy to the patient and obtains the consent of the patient to the therapy, either exactly as recommended by the DMM, or as adjusted to some variation of it, based on the patient's responses. The patient may also reject the recommended therapy entirely. Function 840 receives control at starting node 920. Then process 840 passes control to step 922, which outputs the therapy as recommended in the DMO to the patient. Next, process 840 passes control to step 924, which presents the risks and benefits to the patient. Next, process 840 passes control to step 926, which presents other therapy choices to the patient. Next, process 840 passes control to step 928, which asks the patient to agree to the recommended therapy, or to some version of the therapy. Next, process 840 passes control to step 930, which updates the DMO to record the choices offered, warnings given, and consent level received, with suitable date and time stamps. Next, process 840 passes control to step 932, which computes a function result to be returned to the calling process. The consent level granted by the patient may have several values. The four values used in the flowcharts assume a drug therapy, and are: (1) ok to increase dosage; (2) ok to keep dosage at same level; (3) ok to reduce dosage; and (4) reject this therapy. Next, process 840 passes control to terminal node 934, which returns control to the calling process.

Close Session

Figure 18:
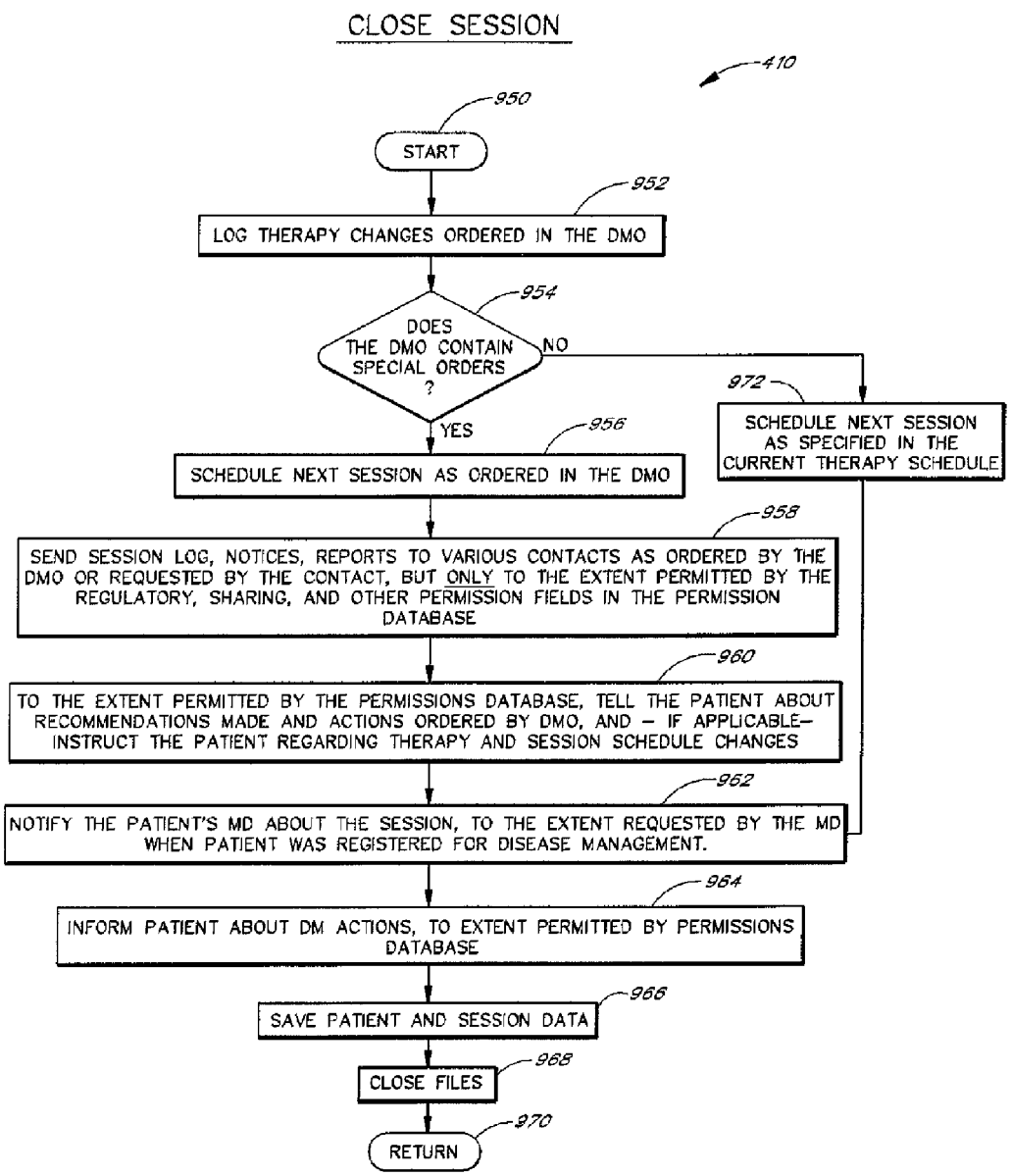
FIG. 18 is a flowchart of the Close Session process shown in FIG. 5.

Referring to FIG. 18, the Close Session process 410 will be described. Process 410 is the last process executed for every DM session. It is specifically responsible for processing the Disease Management Order (DMO), which contains the complete set of tests made and reasons therefore, the next therapy step recommended, consent given by the patient, and various associated orders, such as to fax a prescription to the patient's pharmacy, to order a test from a laboratory, to prepare a report for the patient's physician, to send printed instructions to the patient, and so on. Aside from implementing the DMO details, process 410 is also generally responsible for logging all events that occurred during the DM session, storing all relevant data, closing all applicable files, scheduling the next DM session, and finally bidding the patient farewell to indicate that the current DM session is terminated.

Process 410 receives control at start node 950. Next, process 410 passes control to test 952, which logs the therapy ordered by the DMO in the patient's medical history. Then process 410 passes control to test 954, which determines whether the DMO contains special orders to be processed. If test 954 determines that the DMO has no special therapy orders, process 410 passes control to step 972, which schedules the next DM session as specified in the current therapy schedule of the patient. Then, process 410 passes control to node 962. Processing from node 962 is described below for process 410. If test 954 determines that the DMO has special orders, process 410 passes control to step 956, which schedules the next DM session as ordered by the DMO. Next, process 410 passes control to step 958, which prepares and sends various notices and reports to various contacts. These notifications and the contacts that receive them are controlled by the Regulatory, Sharing, and other authorization fields that are maintained in the Permissions database. Next, process 410 passes control to step 960, which informs the patient about the next therapy step and gives the patient instructions as ordered by the DMO and as permitted by the Permissions database. Next, process 410 passes control to step 962.

Step 962 informs the patient's physician about the DM session and about the therapy ordered by the DMM. While the patient's physician is always entitled to all information generated for the patient, the physician may specify the notices sent and the detail reported. The physician's current requirements and limitations for notification are stored in the permissions database, and may be modified by the physician using processes outside of the DMM. Next, process 410 passes control to step 964, which informs the patient about the actions taken by the DMM software, to the extent permitted in the Permissions database. This step allows the system to tell the patient what it is doing and why, which can gain the patient's confidence and help the patient to make better decisions in future sessions. This feedback is an important element of the long-term therapy optimization that is one of the hallmarks of this invention. Step 964 also reviews all special flags set to discuss new symptoms with the patient. Next, process 410 passes control to step 966, which saves all relevant data in various suitable main and backup storage locations. Next, process 410 passes control to step 968, which closes all applicable data files and releases all temporary computing system resources allocated to the DM session. Next, process 410 passes control to terminal node 970, which returns control to the calling process.

Question Versions

The Question Versions feature of the DMM allows several different versions of the same question to be written into a script, and defers the decision which version to use until run-time. The feature uses a global data item called the Question Version Index (QVI) to select the desired version of the question from the script at run time.

The Question Version feature can be visualized as a "Question Roller": a multi-faceted cylinder with one different version of the question written on each face. To ask a question, the cylinder is rolled to display the face that contains the desired question text. If each question of a set is written on a separate cylinder, and all cylinders are rolled in unison to display the same face, as specified by a global control element, the entire question set of the script can be adjusted or "rolled" as one unit, so that the script as a whole can be adjusted or fine-tuned to ask different versions of the question at different levels.

One use of the Question Versions feature is to be able to globally adjust the sensitivity and selectivity of the language used by the entire DMM, using a DMM-global QVI that controls the linguistic sensitivity. Thus, when the sensitivity or selectivity of questions needs to be altered, the Question Roller is turned or ratcheted one way to increase the sensitivity and the opposite way to increase the selectivity. For this use, each question version differs only slightly in wording and sensitivity. In some cases, the only difference is a comma (a pause) or an intonation of the voice, such as:

Is this absolutely the worst headache that you can imagine anyone having?

Is this the worst headache that you can imagine anyone having?

Is this the worst headache you have ever had?

Is this one of your worst headaches?

Another use of the Question Version feature is to write script questions aimed at different levels of patient education, intelligence, disease understanding, or medical expertise. For example, the DMM can ask the same question in various forms written for a 3rd grader, for a high school student, for a college graduate, or for a health care provider. Thus, the DMM can adapt output to the patient's communication needs, which may involve a range of decisions based on what is currently known about the patient, such as what natural language to use, what the level of understanding is, what grammar to use (e.g., are we addressing the patient, the patient's relative, or the patient's doctor?), and what medical details to disclose. The DMM can consult the patient's medical history to determine the level of the language, education, and intelligence that the patient can understand. If no indicator is present, a mini language IQ test can be given as part of the Initial Health Assessment task to establish the QVI to use with the patient.

Yet another use of the Question Version feature is to allow the DMM to adjust the question level dynamically, based on the patient responses or requests. Thus, a patient who is getting confused or lost may ask the DMM to give more detailed instructions on how to respond to questions. The DMM can react by altering the QVI to select more appropriate question versions. On the other hand, as the patient learns during a session, s/he may later request fewer instructions and a faster communications mode. Again, the DMM can respond by adjusting the QVI. In this manner, the DMM learns about the patient's current and past use of the DMM and can modify itself to adapt to the patient's natural language, education, medical knowledge, and medical sensitivity required.

The Question Version feature is implemented in software by allowing script authors to collect different versions of a question into a "version group," in which each version of the question is associated with a different QVI. At run-time, the DMM uses the Sensitivity Factor Set to establish a global QVI to specify the current question version to be used with the current patient by all scripts. When a DMM process (such as the script engine) needs to output a question, it uses the global QVI to find and retrieve the desired question from the script's question group. Questions that do not require different versions are written as a version group with only one question, which acts as the default question. This default question is also used when there is no question in the version group for the current global QVI.

This Question Version design allows questions versions to be written for a wide range of QVIs, without having to write a version for each QVI. A simple script can just have one question version; as the script improves, additional question versions are added. For example, the first script might be written in English, and later upgraded to add Spanish versions of each question.

Figures 19A, 19B:
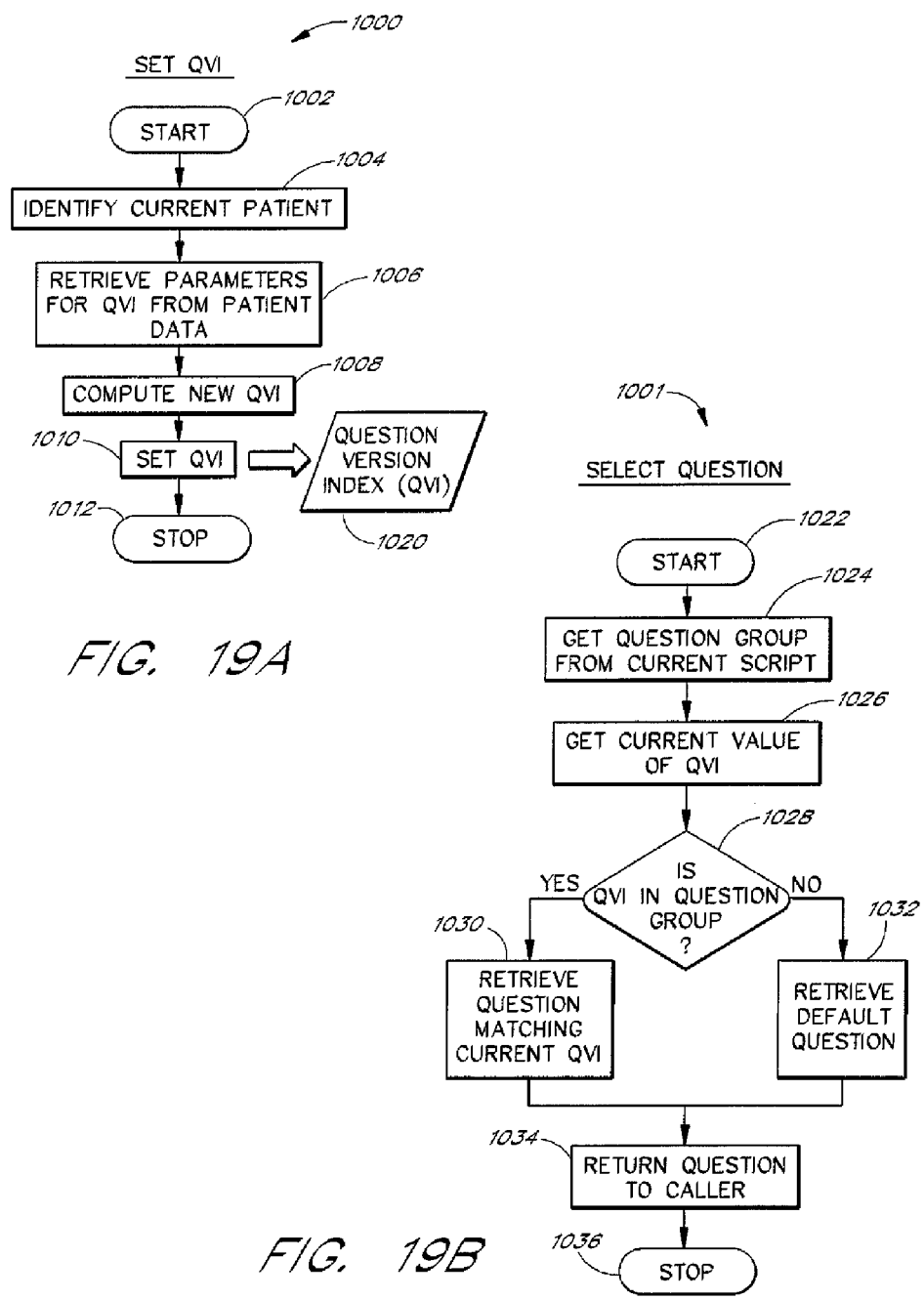
FIGS. 19a and 19b are flowcharts of the Question Versions feature utilized by the Disease Management Module process shown in FIGS. 1 and 5.

The Question Version feature is implemented in the form of a Question Version Index and two separate functions Set QVI and Select Question. In FIGS. 19a and 19b, these elements are shown as follows:

Global Version Index (QVI) is data item 1020;

Set QVI is process 1000;

Select Question process is shown as process 1001.

The current setting of the Global Version Index 1020 determines which one of several different question versions is selected and output to the patient. Data element 1020 is stored as a control field in the permissions database 256 (FIG. 3), and is changed by process 1000 and used by process 1001.

Process 1000 is a DMM-global system service routine that sets and updates data element 1020 periodically. Process 1000 receives control at starting node 1002. Then process 1000 passes control to step 1004, which identifies the patient whose data element 1020 is to be set. Then process 1000 passes control to step 1006, which retrieves the current value of the patient's data element 1020. Then process 1000 passes control to step 1008, which computes the new value of the data element 1020. Step obtains the level of sensitivity desired from the current Sensitivity Factor Set, and obtains other parameters from the patient medical history, such as the level of patient's education, the level of language understood, and the QVI settings used in past DM sessions. After step 1008 computes a new QVI value, process 1000 passes control to step 1010, which stores the new value in the patient's data element 1020. This completes the action of updating the patient's data element 1020. Then process 1000 passes control to terminal node 1012, which returns control to the calling process.

Process 1001 is a DMM-global routine that uses the Global Version Index 1020 to select one question from a set of questions. Process 1001 receives control at starting node 1022. Then process 1001 passes control to step 1024, which loads the applicable question set from the current script's data area. Then process 1001 passes control to step 1026, which obtains the current value of the Question Version Index 1020 from the patient's permission file. Then process 1001 passes control to test 1028. Test 1028 determines whether the question version selected by the QVI is in the question set obtained in step 1024. If test 1028 determines that the desired version is in the question set, process 1001 passes control to step 1030, which retrieves the question with the desired question level from the set. Then process 1001 passes control to step 1034, which returns the question selected from the set as a function result to the caller. Then process 1001 passes control to terminal node 1036, which returns control to the calling process. If test 1028 determines that the desired version is not in the question set, process 1001 passes control to step 1032, which retrieves the default question from the set. Then process 1001 passes control to step 1034, which returns the question selected from the set as a function result to the caller. Then process 1001 passes control to terminal node 1036, which returns control to the calling process.

Preview Mode

Preview Mode is a DMM script run-time mode that allows the patient to "look ahead," that is to examine the consequences of a response before "officially" giving the response. In effect, the patient can say—at any point in a script—"let me see what this answer would do". One use of Preview Mode is to let the patient suspend an ongoing dialog to see what a pending question means. Knowing the consequences of a response is helpful in clarifying the impact or focus of a question. Thus, in a printed flowchart or procedure, one good way to find the best path is to look ahead to see what the consequences (or recommendations) would be of answering a question a certain way. Another uses of Preview Mode is to let the script explicitly warn the patient that a particular question involves serious consequences, and to use Preview Mode so that the patient can consider the effect of each response. For example, one response may begin action to contact the patient's physician, or to transfer the patient to an emergency facility. If the script can warn the patient about this consequence, the patient can preview these responses without activating them, and can alter the direction of the script dialog.

Figure 20:
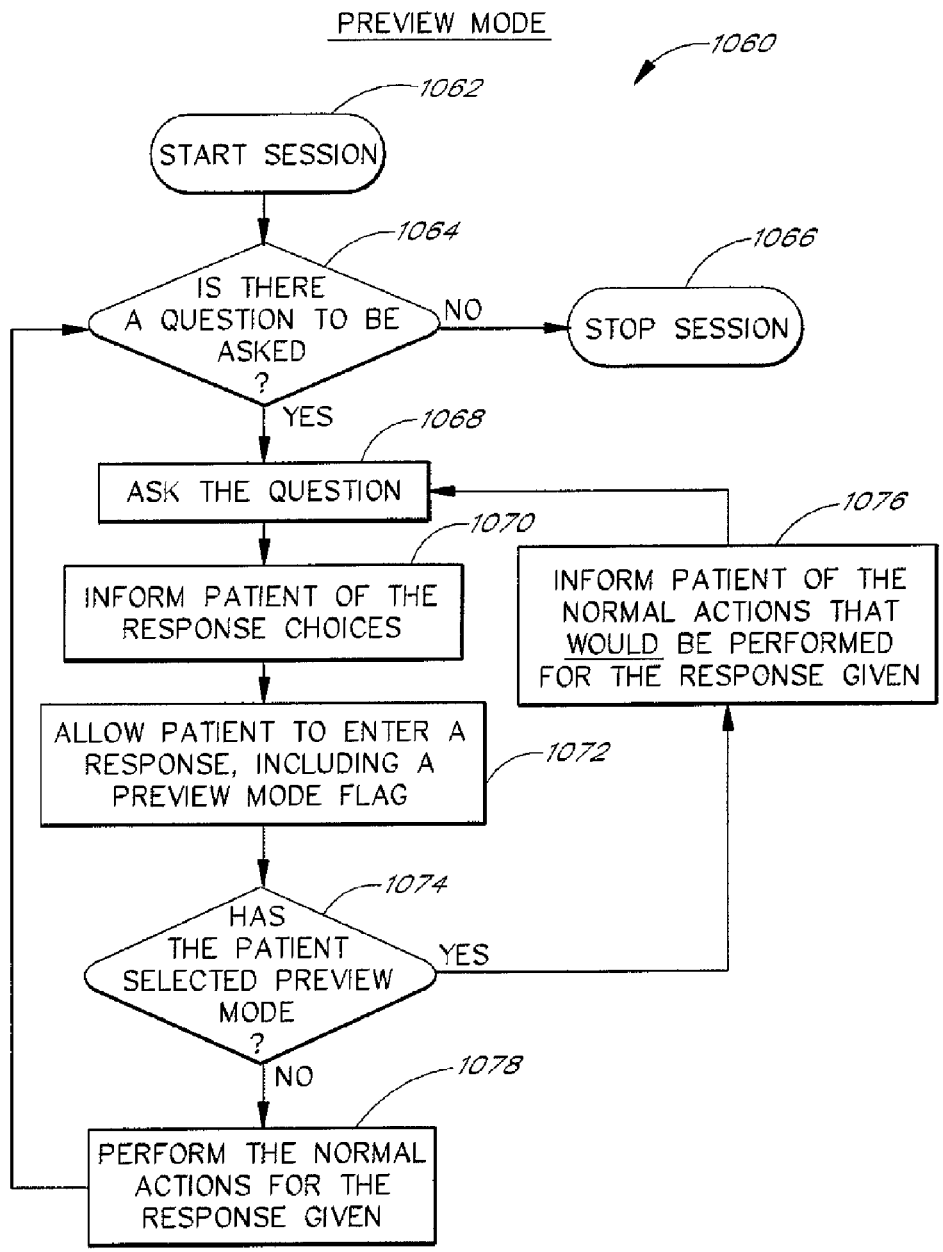
FIG. 20 is a flowchart of the Preview Mode feature utilized by the Disease Management Module process shown in FIGS. 1 and 5.

Referring to FIG. 20, the process 1060 will be described. This process shows only those steps of a DM session that handle the Preview Mode feature, which is involved in the steps that ask the patient a question and process the response.

Other steps of a DM session that are not concerned with the Preview Mode are omitted for clarity. Process 1060 receives control at start node 1062. Then process 1060 passes control to test 1064. If test 1064 determines that there are no further questions to be asked, process 1060 passes control to terminal node 1066, which terminates the Preview Mode. If test 1064 determines that is a question to be asked, process 1060 passes control to step 1068, which outputs the question to the patient. Then process 1060 passes control to step 1070, which outputs the set of responses to the patient. Then process 1060 passes control to step 1072, which inputs a response from the patient, together with an indicator that the patient does or does not want to preview the script's actions for this response. Then process 1060 passes control to test 1074. If test 1074 determines that the patient has responded with the preview indicator set, process 1060 passes control to step 1076. Step 1076 retrieves the preview information that is coded into the script (as part of the normal question and response texts) and outputs it to the patient, so that the patient sees or hears a description of what the selected response would do in "real" mode. For example, a preview text might tell the patient that "A YES response will increase your daily medication dose for the next 2 weeks". After the preview text is output to the patient, process 1060 passes control to step 1068, which asks the same question again, as described above for step 1068. But if test 1074 determines that the patient has responded without the preview indicator, process 1060 passes control to step 1078. Step 1078 performs the actions normally scripted for the response given. Then process 1060 passes control to test 1064, which determines whether there is a next question to be asked, as described above for test 1064.

No-Response Feature

Every DMM dialog with a patient is controlled by a script. During a normal session, the script selects a question and outputs it to the patient, and the patient inputs a response. The script analyzes the response, selects another question, and outputs it to the patient. This question-response-question-response dialog continues until the session is terminated normally. However, when a patient unexpectedly fails to respond in the middle of the dialog, all scripts are designed to invoke the No-Response (NR) feature, which is responsible for taking appropriate continuation action for the script. The NR feature is a DMM software mechanism that is triggered when a timeout condition is signaled by the operating system. The NR mechanism can take any number of actions that have been pre-arranged by the script and can be changed as the script runs. The NR actions can range from a silent entry in the DM sessions log all the way to using health data from the patient medical history and medication and symptom data from the disease database to contact a responsible neighbor of the patient, or a nearby emergency response facility.

One use of the NR feature is to perform a medical disease- and patient-specific evaluation of the failure of the patient to respond. Obviously, in certain patients with certain diseases (e.g. heart problems, head injury, diabetes) the patient's sudden failure to respond in the middle of a normal dialog may indicate any number of possibilities. The NR feature is of special value in the context of the DMM, which has detailed medical information about a patient from previous sessions, and in the context of the First Opinion Support System, which has extensive relevant databases indexed by geographic location around the world (e.g., emergency rooms, 911 agencies, paramedics). Because of what the system knows about a patient, the NR feature can take very situation-specific actions. A very simple example would be a 60-year old man consulting for chest pain: sudden failure to respond to a question would suggest a cardiac arrest and could initiate emergency actions, including calling the patient's local 911 agency.

Figure 21:
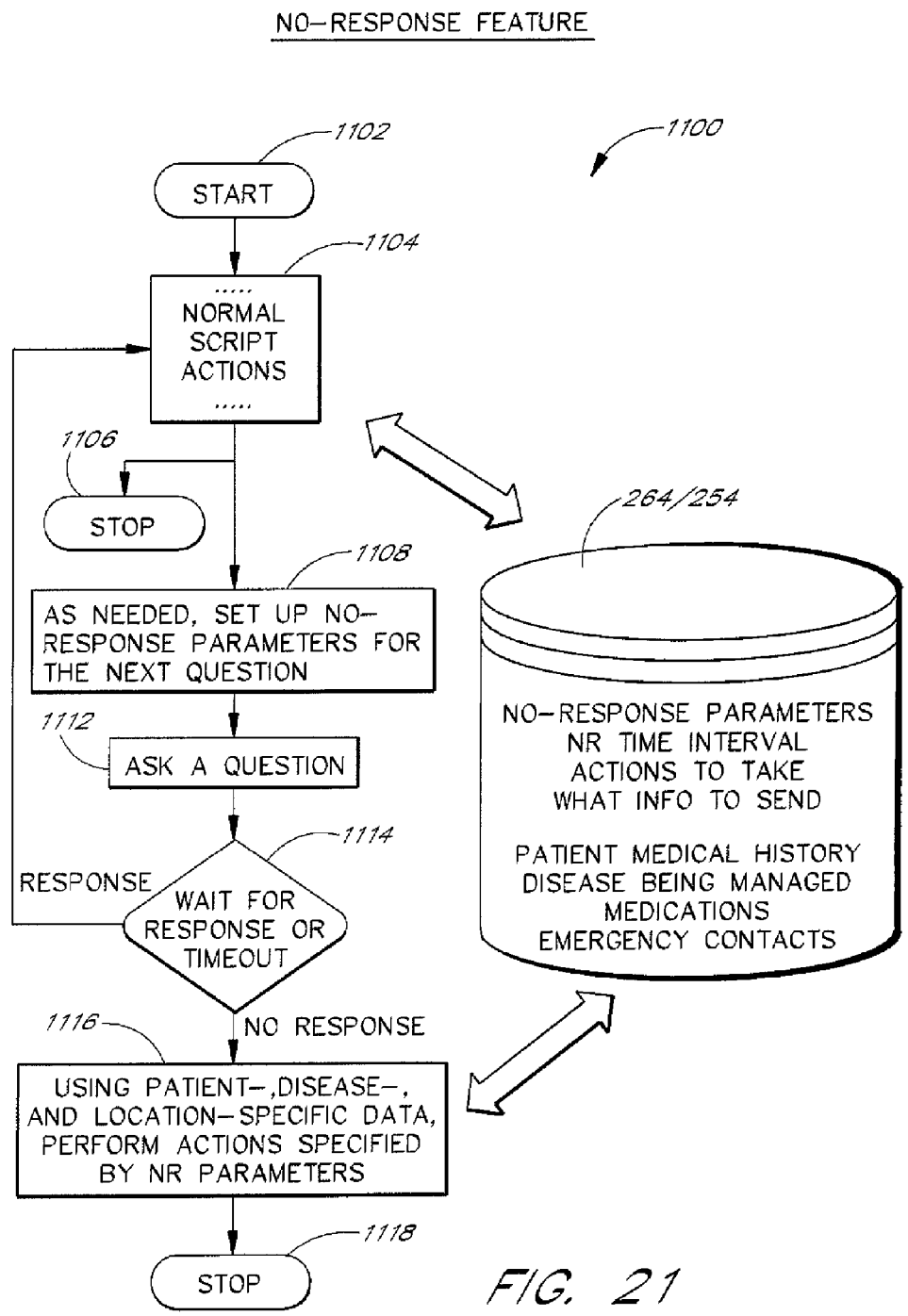
FIG. 21 is a flowchart of the No-Response feature utilized by the Disease Management Module process shown in FIGS. 1 and 5.

Referring to FIG. 21, the process 1100 is described. Note that process 1100 shows only those portions of a script's steps that are relevant to the No-Response Feature. Other steps of the scripts are omitted for clarity. Process 1100 receives control at start node 1102, which represents the generic start node of any script. Then process 1100 passes control to step group 1104. Step group 1104 represents all of the script's actions that do not involve the NR Feature. If the script terminates as part of one of these steps, process 1100 passes control to terminating node 1106, which terminates the script. When one of the steps in step group 1104 wants to ask a question of the patient, process 1100 passes control to step 1108. Step 1108 sets up the NR parameters needed later, if the patient should fail to respond. The source of these parameters is the patient's medical history 254, which contains the relevant information to be used if the patient fails to respond, such as the patient's disease, health state, medications being taken, physician, nearest emergency facility, and so on. Step 1108 stores the NR parameters as a data set 264. Then process 1100 passes control to step 1112, which outputs the actual question to the patient. Then process 1100 passes control to test 1114. Details of step 1114 vary with operating system and hardware platform, but the typical action is to set a timeout flag for a specified wait time, yield control to the operating system, and regain control when the operating system returns a response or the wait time has expired. If test 1114 receives a response, process 1100 passes control to step group 1104, where the normal script's actions continue. If test 1114 receives a timeout, process 1100 passes control to step 1116. Step 1116 retrieves the patient-, disease-, and location-specific NR data from the data sets 264 and 254 and performs the NR actions requested. When step 1116 has performed the NR actions, process 1100 passes control to terminal node 1116, which represents the generic termination of a script due to a timeout.

PQRST Array

Sir Thomas Lewis said that pain is "known to us by experience and described by illustration". The ability to encode the subjective experience of pain into a standard and repeatable format is an essential asset to any system of automated medicine. Many diagnostic sessions begin with a patient reporting some type of pain to a physician in the form of a chief complaint; a thorough description of pain can quickly suggest as well as eliminate many diagnoses, using a table lookup or database access mechanism.

The PQRST Array feature describes a set of software processes and data that work together to encode a patient's description of pain into a "pain code", which is a specially formatted array of integers. Encoding is done in a manner that preserves the subjective information, so that it is possible to decode a pain code by using the array integers to recover the original words used to describe the pain.

A pain code is composed of subcodes; each subcode identifies one well-defined detail aspect of the experience of pain such as location, sensation, frequency, etc. The pain subcodes are arranged into a specific sequence or format that is known to all software processes that manipulate the pain code. The sequence used to encode the aspects is itself prefixed as a number to the sequence, so that so that the first aspect of the array always identifies the coding scheme that is used for the array. This makes the PQRST Array flexible and extensible, since various encoding schemes can be used to meet various needs. Any software process that needs to decode a PQRST in the future simply examines the first aspect code and knows from its value which decoding scheme to use for the rest of the aspects.

The PQRST Array feature permits encoding of a patient's report of pain into digital form that is suitable for software processes. For example, a patient's complaint that "when I bend my right arm or rotate my wrist, even slightly, the elbow area hurts really bad, with a sort of gritty or grinding sound, but there is no bleeding" may be encoded by letting the patient select from standard descriptor words (e.g. gritty, tight, numb) and converting the selected words into an integer array something like (7,2,3,8,5,970612,2,13). This array represents the numeric value of various aspects of pain such as location, repeatability, quality, or a date such as 970612. For any given aspect, the number represents some degree or description of the pain. Thus, if the fourth aspect number represents Sounds-Associated-With-Movement, the subcode value 8 may represent "gritty/grinding noise associated with joint movement".

The "PQRST" label is adapted from the classic mnemonic used by medical students for the basic aspects of pain, which are: P=Provocative/Palliative (what brings it on, makes it worse, or makes it better); Q=Quality (sharp or dull); R=Region (head or chest, etc.); S=Severity (mild to agonizing); and T=Timing (when the pain started). These aspects represent a starting point for the PQRST Array, which is extensible to include other useful subjective descriptors of illness, with many additional aspects associated with the pain such as Cause (infection, trauma), Mass (mole, lump), Size (fingertip, golf ball), Sensation (tickling, pulsing) and objective associations (color, smell, discharge).

To encode a description of pain into a pain code, a process
  uses a set of pre-defined aspects (i.e. facets, elements, dimensions) of pain,
  uses a set of pre-defined aspect words defined for each aspect,
  obtains the applicable aspect word from the patient
  encodes all aspect words into subcodes
  formats the subcodes as a physical data item (the PQRST Array)
  stores the PQRST Array in memory or on disk
  uses the address of the storage location as a pointer
To manipulate a pain code as a whole, a program
  passes the pointer to the PQRST Array
  uses the pointer to access the PQRST Array, if necessary
To decode a pain code, a program reverses the encoding process:
  uses the pointer to locate the PQRST Array in memory or storage
  retrieves the PQRST ARRAY from memory or disk
  retrieves each subcode
  decodes each subcode into its subjective aspect word
  outputs the aspect words as the subjective description.

Figure 22A:
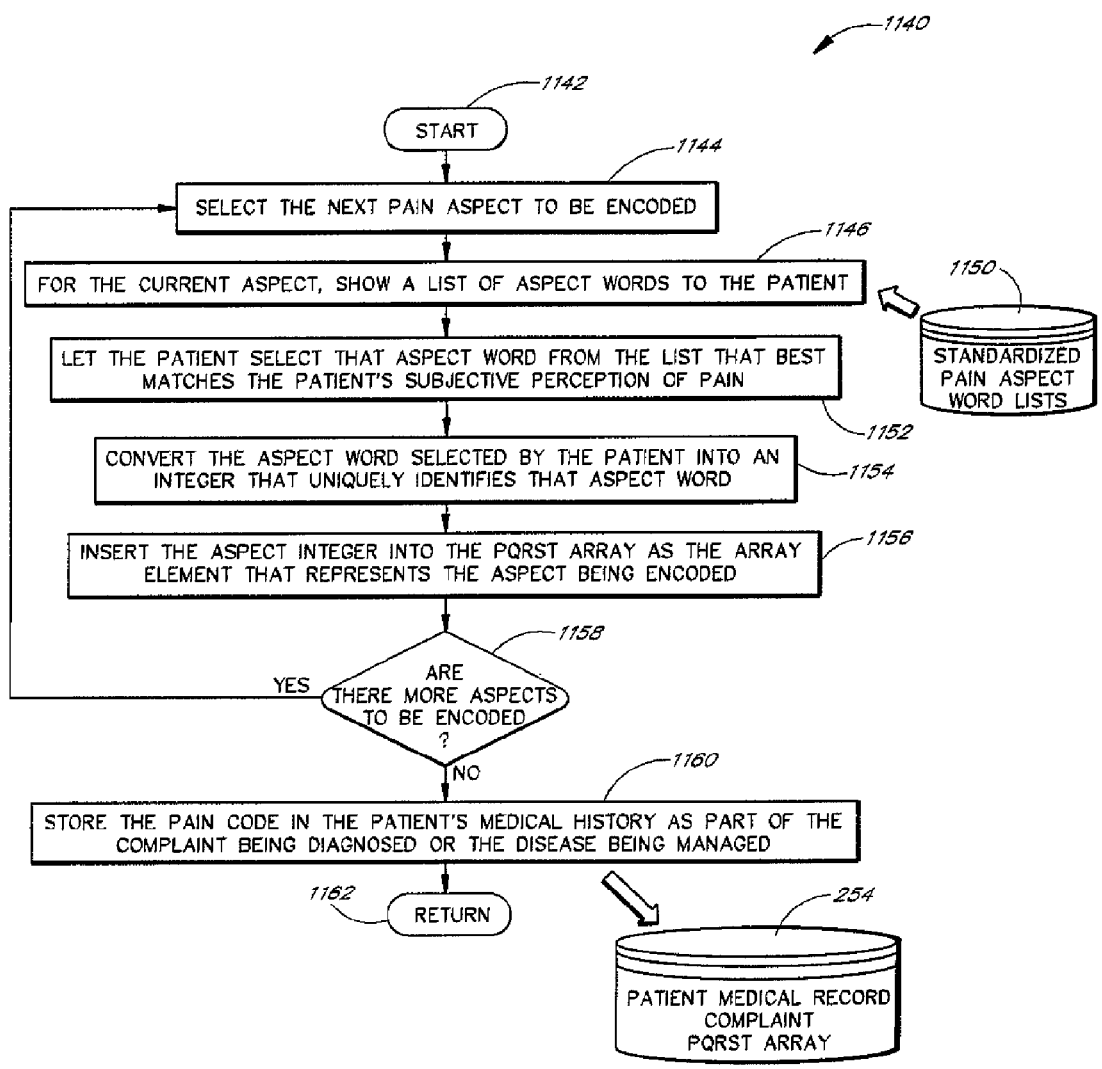
FIG. 22a is a flowchart of a function utilized by the Disease Management Module process shown in FIGS. 4d and 5 and/or the Diagnostic process shown in FIG. 4d in generating a PQRST (pain code) array entry for a patient.

Referring to FIG. 22a, the process 1140 will be described. Process 1140 comprises the steps required to create a PQRST Array that represents the digitized form of a patient's subjective description of pain. Process 1140 is described here assuming that the patient is on-line and can interactively enter subjective pain description details when prompted by process 1140. Process 1140 receives control from a calling process at start step 1142. Step 1142 is the beginning of a loop that encodes pain aspects entered by the patient into a matching set of pain subcodes. Step 1142 allocates space for a PQRST Array that will contain the subcodes. Next, process 1140 passes control to step 1144, which establishes the next pain aspect to be encoded. Next, process 1140 passes control to step 1146, which retrieve a list of standard aspect words from database 1150 and outputs them to the patient in a format of a pick list, i.e. a list that the patient can examine and from which the patient can pick one of the aspect words. Next, process 1140 passes control to step 1152, which asks the patient to select the aspect word from the pick list that best matches the patient's subjective description of the pain aspect being encoded. Next, process 1140 passes control to step 1154, which converts the aspect word selected by the patient into an integer that identifies that aspect word. This integer is the subcode for the current aspect. It can be simply the index position of the selected aspect word in the pick list. Next, process 1140 passes control to step 1156, which inserts the subcode integer into the PQRST Array, at the index position that represents the aspect being encoded. Next, process 1140 passes control to test 1158, which determines whether more aspects are to be encoded. If test 1158 finds that there are more aspects to be encoded, then process 1140 passes control to step 1144 to begin another iteration of the loop just described. If test 1158 finds that there are no more aspects to be encoded, then process 1140 passes control to step 1160, which stores or copies the PQRST Array into the appropriate data set, such as the patient's medical history 254. Next, process 1140 passes control to step 1162. Step 1162 returns control to the calling process.

Figure 22B:
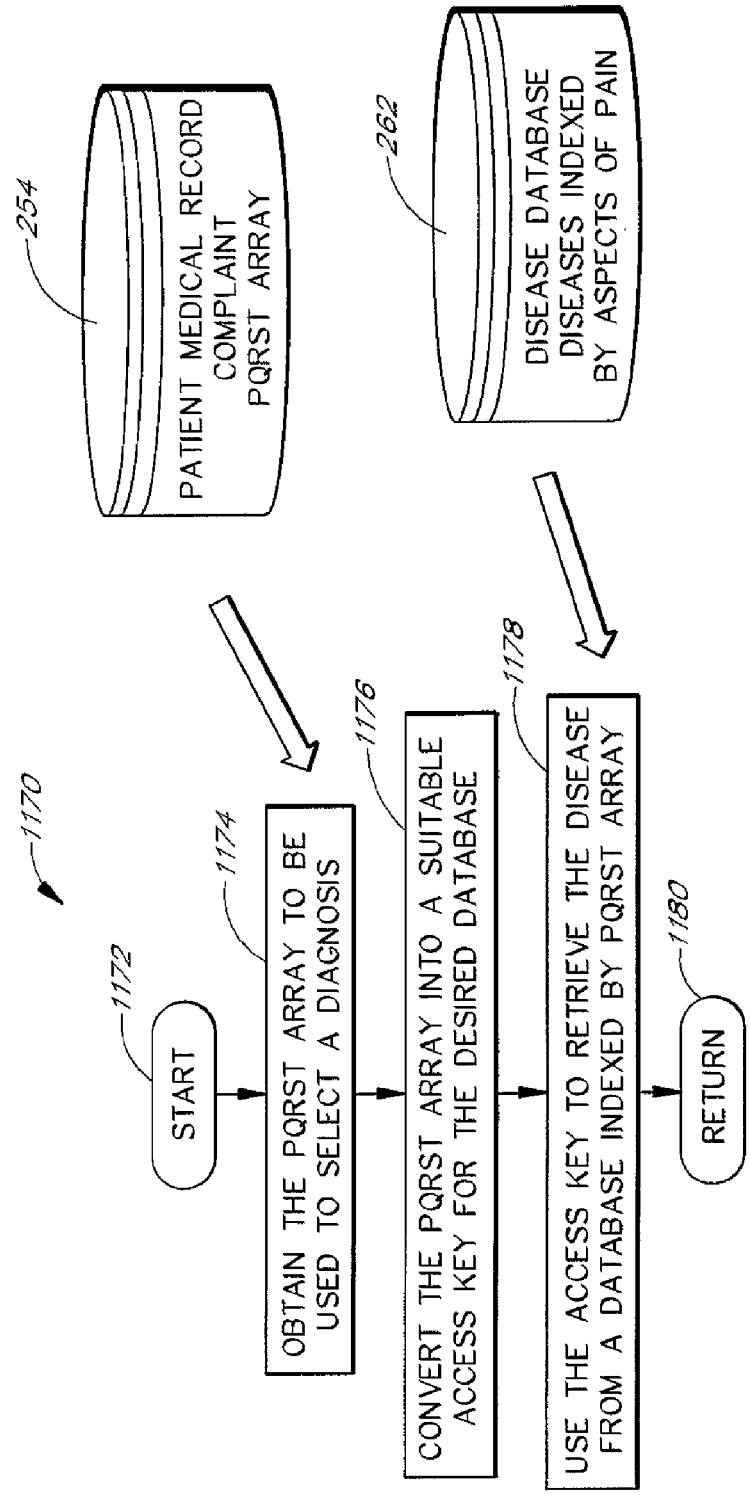

Referring to FIG. 22b, the process 1170 will be described. Process 1170 is an example of the steps required to use a PQRST Array as an index to retrieve a specific diagnosis from a table of diseases. This example assumes that a list of diseases (or disease sets, where there is more than one disease for a given pain code) has been indexed by pain code and stored into a database of diseases 262. This example also assumes that there is a software process for accessing the database that can retrieve elements of the database when given an access key. One obvious example of such a database access mechanism is a suitably formatted Structured Query Language (SQL) statement; another example is a simple array of disease names or pointer that is accessed using the index position of each element. Process 1170 receives control at start node 1172. Then process 1170 passes control to step 1174, which loads a copy of the PQRST Array to be used to select the diagnosis from database 262. Next, process 1170 passes control to step 1176, which converts the DMM pain code into an access key that is formatted as required by the process that accesses database 262. Next, process 1170 passes control to step 1178, which uses the access key to retrieve the record matching the pain code from database 262. Next, process 1170 passes control to terminal node 1180, which returns control to the calling process.

Disease Management Order (DMO)

The Disease Management Order is a data record that is attached to the patient at the beginning of a DM session, travels with the patient from process to process, and is used at the end of the session (by the Close Sessions process) to implement the decisions and orders issued by the various processes during the session. The DMO record contains numerous fields and is stored in the sessions area of the DM-specific databases 264 (FIG. 3). One key field of the DMO, named Code, typically contains the next processing to be performed for the patient.

One use for the DMO is to signal special processing required for a patient. For example, to flag a new patient for a one-time requirement to conduct an initial interview, the Open Session process sets the DMO Code field to "assess initial health" (FIG. 6, node 448). The DM session process then continues into Health Assessment, which examines the DMO Code and shunts the patient into the Initial Health Assessment process 488 (FIG. 7).

Another use for the DMO is to repeat processes as needed. For example, if the Correlation Assessment process requires additional health data for the interval between session, it can invoke Health Assessment again to obtain missing data (FIG. 12, node 660). When the process has enough data, it sets the DMO Code to "optimize therapy" and the patient is shunted out of the assessment cycle.

Another use of the DMO is to track various reasons for decisions made, which can be used by the Close Sessions process to issue detailed reports of what the DM processes learned about the patient. For example, the Therapy Adjustment processes can refer the patient to a physician for different reasons (FIG. 14, nodes 778 and 784; FIG. 15, nodes 832,854). In each case, the DMO code is set to "refer to MD", but the DMO Reason field is set to indicate a different reason.

Finally, the key use of the DMO is to represent "doctor's orders", i.e. to accumulate all of the orders issued during the session, so that they can be implemented when the session is terminated (FIG. 18, node 956).

Permission Database

The Permissions Database 256 (FIG. 3) is a collection of all of the software elements that control access to DMM data and actions taken by DMM processes. This database supports the DMM safety, security, reliability, control, and management features in the form of passwords, access rights, need-to-know and right-to-know clearances, disclosure authorizations, consents, constraints, limits, thresholds, and so on. The Permissions Database is the interface through which a human staff of medical and software experts can specify and control what automatic actions the DMM can and cannot perform. Since permissions govern the actions of all DMM processes, the Permissions Database can be used to dynamically configure the system to run in various modes, ranging from fully automatic to totally non-automatic, where the DMM has to ask permission for every detail step to be taken. The latter mode is especially useful for experimental, test, problem tracking, or system auditing uses.

Three tables of the Permissions Database are relevant to the operation of the DMM processes described above; they are described under their respective section headings below: Regulatory Permissions, Sharing Permissions, and Therapy Alteration Permission Level (TAPL).

Regulatory Permissions

Regulatory Permissions are data sets that insure compliance of the DMM with all applicable regulatory, licensing, and legal requirements and restrictions of the many jurisdictions in which it operates. The Regulatory Permission data sets are organized by jurisdiction, and specify for each jurisdiction which data fields can be disclosed to what agency. The Regulatory Permissions feature addresses a very complex issue that is typically ignored by other automated medical systems, namely that such systems may be deemed to be practicing medicine in and across controlling jurisdictions, even across international borders, and must therefore meet a large number of various medical practice constrains and licensing regulations. This feature allows the DMM to comply with the law in its actions and in its contacts with patients, physicians, health care management organizations, government agencies, and so on.

Regulatory Permissions are DMM-global, and can be used wherever they are applicable. One example is in the Close Session process (FIG. 18, nodes 958-964) which must consider the legal requirements and prohibitions regarding disclosure of confidential medical data before distributing notices, instructions, and reports about the DM session or the patient.

Sharing Permissions

Sharing Permissions are used to manage disclosure of individual medical data items. Every data field in the patient medical history is associated with an access control field that specifies whether or not the medical data item can be disclosed to the patient, to various agents or agencies, and to other software objects with specific access authorizations. Sharing Permissions are used by the DMM Close Session process (FIG. 18, nodes 958, 960) to decide what medical data items can be disclosed (i.e. "shared"). in its messages and reports to patients, patient agents, physicians, laboratories, pharmacies, health care management organizations, or government agencies.

Another use of Sharing Permissions is to prevent a diagnosis from being disclosed to the patient under circumstances when it would be inappropriate (FIG. 18, node 964).

Therapy Alteration Permission Level (TAPL)

The Therapy Alteration Permission Level (TAPL) is a data set that specifies the various levels of authority the DMM has to change patient therapy. The TAPL defines the degree of autonomy that the DMM has to manage a patient's disease without prior human approval. Whenever a patient medical history data item is requested by (say) a government agency or an insurance company, the DMM consults the access control field of that data item to see which sharing permission level is required for it. Then the DMM consults the Permissions database to verify that the requesting agency has access permission at the specified level.

At its most restrictive level, the TAPL requires DMM to notify a physician whenever the DMM determines that the patient could benefit from a change in therapy, and to obtain permission before adjusting therapy in any way. The least restrictive TAPL setting allows the DMM to automatically change a patient's treatment without human intervention. TAPL settings between these extremes require various degrees of prior notification and approval for different therapeutic interventions. The TAPL is used by all DMM functions that change patient therapy or give advice to that effect (FIG. 15, node 830; FIG. 16, node 896).

Meta Structures

Meta Data Array

For the purpose of discussing the medical management system meta functions, a system data structure used to record, track, analyze, and report medical problems can best be visualized as a two-dimensional grid or array called the Meta Data Array. This array lists the causes of disease (e.g., trauma, infection, allergy) along one dimension (the abscissa or x-axis) labeled as CAUSE and lists the anatomic systems or organs affected by disease (e.g., cardiovascular, respiratory, nervous) along a second dimension (the ordinate or y-axis) labeled as ANATOMY. A given disease can then be seen as the cell in the Meta Data Array that is at the intersection of the applicable Cause and Anatomy dimensions.

In implementation, both the Cause and Anatomy axes are, of course, extensively subdivided. Thus, for example, the infection cause is subdivided into bacterial and viral; bacterial is broken down into gram positive and gram negative; gram positive is further broken down into streptococcus, and so on, to the point where the system can identify ultimate causes such as "meningococcal gram negative bacterial infection." The Anatomy dimension can obviously also be subdivided into organ structures, organs, tissues, cells, and so forth.

Meta Data Cube

As the medical management system has more contacts with a given patient, the additional patient data extends the Meta Data Array along a time dimension to form a Meta Data Cube. The time axis is also referred to as the "Z" axis.

The Meta Data Cube is an internal data structure that supports various meta functions. The details vary, depending on which medical system module is performing which type of meta analysis, but all of the following examples apply:

Several episodes of the same complaint (Frequency Meta)
Several infections in different anatomic systems (Cause Meta)
Different complaints in the same anatomic system (Anatomy Meta)
Long-term patient history, e.g., smoking habits over 35 years (Volumetric Meta)
Chronic disease history, e.g., five years of Asthma or Malaria attacks
Short-term disease progress, e.g., three days of gastrointestinal pain, headaches, vomiting Meta Functions Meta Functions are medically-oriented software objects that operate at a global level of the entire medical management system and its various modules. They observe, record, track, and analyze patient interactions with the system to:

evaluate a patient's use of the system,
look for patterns or relationships that may signify a problem,
"step back" to look at the patient's overall interaction with the system,
analyze a patient's current session in the context of past sessions.

Meta Functions automate that aspect of the human physician that sees a patient as a total, complex bio-mechanism that is malfunctioning and requires corrective measures over a time span. They give the DMM the powerful ability to analyze patient health as a whole, to develop long-term medical diagnoses, therapies, advice, and management strategies.

The Frequency Meta Function uses the Sequential Summing Meta Function to analyze the frequency of consultations regarding the same disease. The Anatomic Meta Function analyzes patient complaints based on the anatomic organ system involved. The Cause-Effect Chaining Meta Function traces a disease back to its cause(s) and then forward to other disease(s). The Area Meta Function and the Volumetric Meta Function analyze changes in disease parameters over time. The Critical Curve Meta Function monitors patient health for significant deterioration by comparing it to a standard curve for the disease being managed. The Interval Meta evaluates the time intervals between consultations for the same disease. The Reliability Meta assesses the probability of data reliability and integrity.

The Meta Functions described for disease management use the same "Meta Data Cube" data structure described in Applicant's patent entitled "Computerized Medical Diagnostic and Treatment Advice System," U.S. Pat. No. 5,660,176. However, since DM has different objectives, it examines different data elements of the cube along different axes.

The word "meta" refers to the overall nature of these functions, which focus on manipulating health data not at a detailed level but at a level of long-term time trends, global patterns, statistical distributions, and other summary relationships. The word "function" here refers to the various computational and analytical techniques used, which employ classic and fuzzy logic, arithmetic, geometry, trigonometry, analytical geometry, calculus, statistics, probability, domain mappings, transforms (Laplace, Fourier), heuristics, recursion, and so on.

Meta functions are implemented and embodied in the form of suitable data and process structures such as databases, tables, arrays, modules, objects, scripts, lists, subroutines, procedures, functions, and so on.

A. Sequential Summing Meta

The Sequential Summing (SS) Meta function detects and integrates the effect of one patient accessing separate modules of the entire medical management system, such as the diagnostic module and the DMM, because separate sessions—when combined—may represent a significant change or deterioration in the patient. The SS Meta function analyzes the combined effect of the separate modules, and may make a recommendation based on this global analysis.

The SS Meta uses pre-set thresholds for different combinations of the system modules being summed. The thresholds are contained in an internal table that lists all of the module combinations such as medical diagnosis+disease management, medical diagnosis+medical audio/video/image library, medical diagnosis+treatment table consultation, and so on.

For example, if the Medical Diagnosis module was consulted for wheezing and diagnosed as Asthma, and the DM module was later used for Asthma management, and the Medical Audio/Video/Image library module was consulted several times for pre-recorded messages on Asthma, the SS Meta function would use the proper values from the table at medical diagnosis+disease management+medical audio/video/image library for Asthma to calculate a threshold to trigger special recommendations. Thus, even though threshold was not reached in any one module, when the consultations for asthma in the diagnostic, disease management and audio/video/image library consultations are combined and considered together, threshold is reached.

B. Frequency Meta

The Frequency Meta function reviews the number of times that a patient has consulted the system and makes recommendations based on that consultation frequency. The function calculates how many times the patient has interacted with the system for the same complaint or disease, medical audio text consultation or treatment table consultation, uses the Sequential Summing Meta function to analyze the combined effect of the consultations, and may make a recommendation based on this global analysis.

When a patient is admitted to the medical management system, for each disease being managed, a threshold is established for the number of consultations (inbound as well as outbound) per unit of time. The threshold is different for each disease and is modified by the sensitivity factor set. If this threshold is reached, the Frequency Meta function makes a recommendation. That is, the fact alone that the patient has had a certain number of symptom occurrences of a given type may trigger a recommendation from the Frequency Meta functions.

C. Internal Meta

The Interval Meta function analyzes the time intervals between each interaction for the same disease to detect trends that may signify a problem. For example, if the function were to discover that the patient's interactions with the system are occurring closer and closer together, the function could make a recommendation based on this fact alone.

The sequential summing series method is used. The interval between consultations is plotted and a meta recommendation is made if the intervals are getting shorter D. Cause Meta The Cause Meta function is a DM background task that looks for disease or cause patterns that may help to identify root causes. The function monitors and analyzes the patient's use of various system modules.

The Cause Meta function identifies a sequential summing series in decreasing intervals of time between medical diagnosis, disease management, medical audio text library, treatment table consultation and all their combinations. For example, assume that a patient has consulted the system on several occasions with complaints manifesting in different parts of the body, and that during each session, the medical diagnosis module has (properly) attributed each separate problem to being caused by infection. The Cause Meta function detects such a series of consultations, and—if they reach a preset threshold per unit time—alerts the system that the root cause may lie in the patient's immune system. If the system is caring for a patient with multiple episodes of trauma, the Cause Meta function will help the system to consider the possibility that the patient is abusing drugs or alcohol.

E. Anatomic Meta

The Anatomic Meta function analyzes patient contacts with the medical system from a viewpoint of a single organ or anatomic system of the body. The function looks for different diseases being managed that may impact the same anatomic system. The function automates the aspect of DM that—when different diseases all affect the same organ—it is often essential to monitor and frequently measure the functioning of that organ.

For example, if a patient consults the medical diagnostic module on three different occasions for abdominal pain, vomiting, and diarrhea, the Anatomic Meta function recognizes that these problems all involve the gastrointestinal tract, and may cause the system to adjust its recommendations based on that additional information.

For example, diabetes mellitus and hypertension both cause slow and progressive deterioration of kidney function. The Anatomic Meta function detects the need for such special monitoring. Based on some internal, preset thresholds, the Anatomic Meta analysis may cause disease management system to recommend an evaluation of the impacted organ functions. In the example above, for a patient being managed for diabetes and hypertension, the Anatomic Meta analysis could cause the medical management system to recommend a serum creatinine, a test of kidney function, at appropriate intervals.

F. Cause vs. Anatomic Meta

The Cause vs. Anatomic Meta function coordinates an interaction between the Cause Meta and Anatomic Meta functions. As the Cause Meta and Anatomy Meta functions interact more closely, their interaction is described here.

As the patient uses the medical management system over time, the Cause/Anatomy cells are stacked along the time or Z-axis, which tracks the moment in time when intersection of the cause and anatomic system, i.e., making the diagnosis actually occurred in the patient.

The Meta Data Cube represents a summation of the patient's interaction with the system over time. Although much of the patient's past history is stored using ICD-9-CM codes, as well as conventional text strings in the fields of the patient's medical record, this technique allows very useful analyses to be done.

It is important to note that the system may be able to assign a cause to a problem without knowing the anatomic system involved, and that the system may indicate what organ or organ system is involved without knowing the cause of the patient's problem. For example, a six-year-old child who complains of muscle aches, headache, runny nose, and joint aching most likely has a viral infection, but it is hard to ascribe a specific organ system in which it is being manifested.

Interestingly, while in the diagnostic module, and while finding multiple problems occurring in the same module, a different pattern is produced in disease management. For example, diabetes can be represented by or at the intersection of an endocrine and the vascular system. But another way to visualize the disease process in diabetes is to go one step further as follows. Whenever the medical management system realizes that another disease process (like diabetes) affects the vascular system, then "vascular" as a CAUSE of further disease is searched.

G. Causal Chaining Meta

The Chaining Meta function automates the analysis of the medical fact that certain diseases produce pathologic changes in other organs of the body, meaning that a disease can cause and be caused by other diseases. For example, the Chaining Meta function looks at a given disease as both cause and effect, and performs three analyses for a given disease D:

1. Find the root cause of D.
2. Find other diseases caused by D.
3. Repeat steps 1 and 2 recursively to find other root causes and other diseases caused by D.

Thus, the Chaining Meta analysis traces the total impact of disease on the body. It uses the Cause Meta function (which is used to detect the immediate, single cause of a complaint or disease) to recursively find remote causes and diseases. Given a starting disease, the Chaining Meta analysis uses the Meta Data Cube to detect patterns that let the analysis go backward in the cause chain to detect other possible problems in a patient. In this way, it does the analysis needed to detect related problems that have so far been masked or have not yet surfaced.

An internal Cause-Effect table used by the Cause-Effect Meta function contains fundamental medical knowledge of anatomic systems, their relationships, their diseases, and disease causality chains. This table identifies patterns that need to be explored for root causes and secondary disease. A second table, used in controlling the processing of the causality chains, contains other data such as probability of occurrence, seriousness of the secondary diseases, and possible therapeutic windows.

The result of the Chaining Meta computation is a list of diseases to check for and monitor in the current patient. These results are useful in:

insuring that side effects of disease are not missed,
not overlooking disease management therapy needed to stabilize a patient,
confirming a cause by verifying other effects (headache is consistent with Appendicitis),
negating a cause by not finding required effects (lack of Plasmodia in blood denies Malaria).

Area Meta

An example of area meta can be described as plotting pain or discomfort against time and then integrating the area under the curve to look at the total amount of suffering or discomfort. This is important because many patients, particularly with incurable illness, such as terminal cancer patients, are in continuous pain but they are isolated, do not see their doctor regularly, or their physician does not appreciate how much the patient is suffering. They tend to "chase the pain," and never catch up. Here, once a threshold of suffering as been met, the patient could get narcotic analgesics or have their dose increased.

Volumetric Meta

The Volumetric Meta function performs analysis based on the (3-dimensional) product of Disease×Anatomy×Time and makes recommendations based on pre-set thresholds. The word "volumetric" refers to the Meta Data Cube analysis method used, in which a smoking history appears as the volume enclosed by the three axes P (Poison), R (Respiratory System), and Z (Time). For example, a patient who has smoked two packs of cigarettes daily for 30 years is deemed to have a history of 60 pack-years impacting the respiratory system.

Volumetric analysis is significant in many disease processes. Thus, the patient with a smoking volume of 60 pack-years has accumulated significant damage to the respiratory system. The longer this has been going on, the larger the volume, the more poison has impacted the functioning of the respiratory system, and the more likely certain diagnoses or therapies will be.

Another example of volumetric analysis is the long-term damage that diabetes causes in the microvascular circulation.

The software implementation of the Volumetric Meta function involves various internal disease management tables that list volumetric products for various diseases as well as their threshold parameters. These thresholds (as modified dynamically by the sensitivity factor set) control special actions and analyses of the system. When an applicable threshold is reached, the system performs special analyses and then issues internal alerts to look for possible evidence of damage being done to the applicable organ system(s) and to make special recommendations for the patient.

Reliability Meta

The Reliability Meta function looks at the reliability of all of a patient's data items to see if the patient's care is inadequate. The function can recommend the re-evaluation of a patient if it finds that the (separate or combined) probabilities of a diagnosis are below a reliability threshold (modified by the sensitivity factor set).

The function uses internal Reliability Indicators, associated with every data item, that track the probability that the data item reflects the actual health of the patient at the time for which it was recorded. These Reliability Indicators are established for every data item in the medical management system when it is first established, and remain associated with it throughout its life in the system.

For example, if a patient tells the system that he has a history of migraine headaches, the system may ask the patient:

Who made the diagnosis of migraine (patient, friend, nurse, physician, or neurologist)?

What tests were run, by whom, on what tissue, with what results?

Who confirmed the tests, how, in what context?

The idea, of course, is that if a headache specialist made the diagnosis after a full and complete workup including imaging (MRI) of the brain, lumbar puncture, EEG, etc., the probability that the diagnosis is correct is very high. This will be recorded in the Reliability Indicators and associated with the diagnosis data item. If the reliability is too low, the patient will be scheduled for re-evaluation at a higher level or standard of care, which will invoke more precise and more thorough questioning.

Benefits of Disease Management

The benefits of the medical management system and the Disease Management Module are as follows:

Benefits to Patients
- faster, easier, cheaper medical services
- medical service accessible at off hours, from home, when needed
- medical service accessible in remote locations, poor communities
- the latest, best, tested, updated medical services
- patients can take their time, can repeat sessions, can browse
- patients have a complete medical history on file Benefits to Health Care Providers
- reduces trivial, inappropriate, useless contacts with patients
- hones doctor's diagnostic skills/experience
- doctor can compare own opinion to others
- repeat patients offer better, continuous medical records
- providers can access more medical data resources
- computer supports access to statistics, databases, decision-making, scheduling
- history of sessions and diseases is available
- providers can justify advice/actions based on logged responses
- can compare patients across/along populations
- have large database of cases Benefits to Health Care Managers
- saves costs of trivial contacts
- tracks contacts
- statistical information and projections
- profiles doctor/hospital practices
- session logs reduce legal liability and exposure
- ensures compliance with policies
- standardizes advice and treatment Benefits to Health Care Regulators
- actions of HMOs, Physicians can be reviewed and assessed
- medical records are available for critiques
- can verify compliance with regulations Benefits to Health Care Teachers
- medical practice can be simulated on large patient populations
- aids study of medicine
- case studies can be compared
- case handling can be repeated, with changes While the above detailed description has shown, described, and pointed out the fundamental novel features of the invention as applied to various embodiments, it will be understood that various omissions and substitutions and changes in the form and details of the system illustrated may be made by those skilled in the art, without departing from the spirit of the invention.

What is claimed is:

1. An automated system, having a computing device configured to allow a patient to self-encode a subjective description of a pain experienced by the patient, via direct interactive dialogue between the patient and the computing device, the system comprising:

a software function executing on the computing device configured to allow a patient to self-encode a subjective description of said pain to represent a degree or description of pain; and a set of aspect words stored in a data storage operatively coupled to the computing device, wherein the set of aspect words comprises encoded numeric values representing a plurality of different aspects of subjective patient descriptions of pain;

a pain code array generated by the software function comprising the numeric values representative of the patient's self-encoded aspect words.

2. The system of claim 1, wherein numeric values of the pain code array are represented in digital form.

3. The system of claim 1, wherein the pain code array comprises a plurality of subcodes for identifying defined details of the subjective description of the patient's pain for identifying a disease or adjusting a treatment.

4. The system of claim 3, wherein the subcodes comprise a location, sensation, or frequency of a pain.

5. The system of claim 3, wherein the subcodes comprise provocative, quality, region, severity, or timing of a pain.

6. The system of claim 3, further comprising a prefix subcode for identifying a coding scheme of the pain code array.

7. A computerized method for digitally representing a self-description of a pain experienced by a patient into a pain code array, the method comprising:
    encoding the self-description of the pain experienced by the patient including:
    storing a set of aspect words in a data storage, wherein the aspect words correspond to an aspect of pain, the aspect words are mapped to subcodes, the data storage being operatively coupled with a computing device;
    receiving, via direct interactive dialogue between the patient and the computing device, one or more aspect words from the patient that self-describes the pain experienced by the patient;
    encoding the received aspect words into the subcodes; and
    combining the subcodes into the pain code array.

8. The method of claim 7, wherein the set of aspect words comprise sharp and dull pain.

9. The method of claim 7, further comprising providing a pointer to a memory location, wherein the memory location stores the pain code array.

10. The method of claim 7, wherein the patient is a human being in need of wellness care.

11. The method of claim 7, wherein the set of aspect words provide subjective descriptors of an illness with an associated pain.

12. The method of claim 11, wherein the subjective descriptors comprise one or more of cause, mass, size, or sensation.

13. The method of claim 12, wherein the cause descriptor comprises an infection or trauma.

14. The method of claim 7, further comprising:
    decoding a description of pain from the pain code array, comprising:
    retrieving the pain code array containing one or more subcodes from a storage location of the pain code array; and
    decoding the subcodes of the pain code array into subjective aspect words.

15. The method of claim 14, further comprising outputting the subjective aspect words for each subcode to provide a subjective description of a patient's pain.

16. The method of claim 15, wherein the outputted aspect words recover an original set of words selected by a patient or an agent of the patient to describe a pain.

17. The method of claim 7, further comprising diagnosing a disease, the method comprising:
    encoding a patient's subjective perception of pain into a pain code; and
    indexing a database of diseases with the pain code thereby diagnosing a disease.

18. The method of claim 17, wherein the pain code comprises subcodes representative of provocative, quality, region, severity and timing of the pain.

19. A non-transitory computer readable medium having computer readable program code embodied therein configured to allow a patient to self-encode a subjective experience of a pain experienced by the patient in a digitized form, the computer readable code comprising instructions for:
    storing, in a data storage accessible to the program code, a listing of aspect words describing a pain, including a degree or description of the pain;
    receiving, via direct interactive dialogue between the patient and the program code, a patient self-selection of an aspect word from the listing of aspect words, the self-selection describing a pain experienced by the patient; and
    converting the received aspect word into an integer subcode that represents the received aspect word.

20. The computer readable medium of claim 19, further comprising inserting the integer subcode into a pain code array.

21. The computer readable medium of claim 19, further comprising performing another iteration of the computer instructions by providing the patient with another listing of aspect words to encode another selected aspect word in the pain code array.

22. The computer readable medium of claim 19, further comprising using the pain code array to access one or more associated diseases from a database comprising a list of pain codes and diseases, wherein the list of pain codes and diseases is indexed by pain code allowing multiple diseases to be associated to a pain code.

23. The computer readable medium of claim 19, wherein the pain code array suggests or eliminates at least one diagnosis of the pain.

24. The computer readable usable medium of claim 19, wherein the aspect word is selected by a healthcare provider, healthcare provider's agent, patient, or patient's agent.

* * * * *